United States Patent
Lafontaine et al.

(10) Patent No.: US 6,864,268 B2
(45) Date of Patent: Mar. 8, 2005

(54) β₃ ADRENERGIC RECEPTOR AGONISTS

(75) Inventors: Jennifer A. Lafontaine, San Diego, CA (US); Bradley P. Morgan, Moraga, CA (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 10/373,119

(22) Filed: Feb. 24, 2003

(65) Prior Publication Data
US 2003/0212063 A1 Nov. 13, 2003

Related U.S. Application Data

(60) Provisional application No. 60/360,251, filed on Feb. 27, 2002, and provisional application No. 60/432,074, filed on Dec. 9, 2002.

(51) Int. Cl.⁷ .................. A61K 31/4439; C07D 413/12
(52) U.S. Cl. ..................................... 514/340; 546/271.4
(58) Field of Search ........................ 514/340; 546/271.4

(56) References Cited

U.S. PATENT DOCUMENTS

| | | | |
|---|---|---|---|
| 4,358,455 A | 11/1982 | Atkinson et al. | 424/263 |
| 4,478,849 A | 10/1984 | Ainsworth et al. | 424/285 |
| 4,918,091 A | 4/1990 | Cantello et al. | 514/369 |
| 5,019,578 A | 5/1991 | Fisher et al. | 514/275 |
| 5,030,640 A | 7/1991 | Fisher et al. | 514/339 |
| 5,051,423 A | 9/1991 | Lis et al. | 514/252 |
| 5,135,932 A | 8/1992 | Hauel et al. | 514/253 |
| 5,153,210 A | 10/1992 | Ainsworth et al. | 514/369 |
| 5,393,779 A | 2/1995 | Holloway et al. | 514/539 |
| 5,541,197 A | 7/1996 | Fisher et al. | 514/311 |
| 5,684,022 A | 11/1997 | Shuto et al. | 514/335 |
| 5,767,133 A | 6/1998 | Dow et al. | 514/339 |
| 5,776,983 A | 7/1998 | Washburn et al. | 514/605 |
| 5,840,738 A | 11/1998 | Bell et al. | 514/359 |
| 5,843,972 A | 12/1998 | Dow et al. | 514/367 |
| 5,859,044 A | 1/1999 | Dow et al. | 514/419 |
| 5,977,124 A | 11/1999 | Dow | 514/272 |
| 6,001,856 A | 12/1999 | Dow | 514/330 |
| 6,008,361 A | 12/1999 | Wright | 546/307 |
| 6,090,942 A | 7/2000 | DeVries et al. | 546/14 |
| 6,187,809 B1 | 2/2001 | Miyoshi et al. | 514/443 |
| 6,251,925 B1 | 6/2001 | Donaldson et al. | 514/354 |
| 6,265,581 B1 | 7/2001 | Bell et al. | 546/277.4 |
| 6,291,489 B1 | 9/2001 | DeVries et al. | 514/352 |
| 6,291,491 B1 | 9/2001 | Weber et al. | 514/357 |
| 6,441,181 B1 | 8/2002 | Scott | 546/276.4 |
| 6,451,587 B1 | 9/2002 | Burns et al. | 435/280 |
| 6,465,501 B2 | 10/2002 | Malamas et al. | 514/376 |
| 6,566,377 B2 * | 5/2003 | Day et al. | 514/340 |

FOREIGN PATENT DOCUMENTS

| | | |
|---|---|---|
| EP | 0236624 | 8/1993 |
| EP | 0543662 | 9/1996 |
| EP | 0764632 | 3/1997 |
| EP | 0882707 | 12/1998 |
| EP | 1236723 | 9/2002 |
| WO | WO 9000548 | 1/1990 |
| WO | WO 9804526 | 2/1998 |
| WO | WO 9821184 | 5/1998 |
| WO | WO 9942455 | 8/1999 |
| WO | WO 9945006 | 9/1999 |
| WO | WO 0040560 | 7/2000 |
| WO | WO 0232897 | 4/2002 |
| WO | WO 0248134 | 6/2002 |

* cited by examiner

Primary Examiner—Patricia L. Morris
(74) Attorney, Agent, or Firm—Peter C. Richardson; Gregg C. Benson; Arlene K. Musser

(57) ABSTRACT

The present invention provides β₃-adrenergic receptor agonists of structural Formula (I) as well as pharmaceutical formulations thereof and methods for treating β₃-adrenergic receptor-mediated diseases, conditions, or disorders using such compounds.

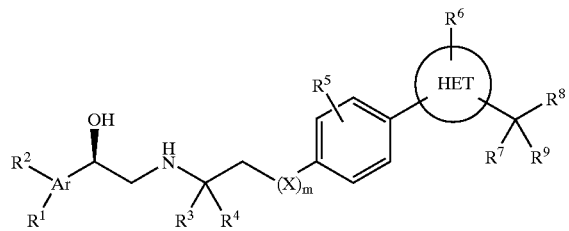

(I)

27 Claims, No Drawings

$\beta_3$ ADRENERGIC RECEPTOR AGONISTS

This application claims the benefit of U.S. Provisional Application Nos. 60/360,251, filed on Feb. 27, 2002, and 60/432,074, filed on Dec. 9, 2002, and incorporated herein by reference in their entirety.

FIELD OF THE INVENTION

The present invention relates to $\beta_3$ adrenergic receptor agonists and uses thereof to treat diseases, conditions and/or disorders modulated by $\beta_3$ adrenergic receptor agonists.

BACKGROUND OF THE INVENTION

The disease diabetes mellitus is characterized by metabolic defects in the production and utilization of carbohydrates that result in the failure to maintain appropriate blood sugar levels. The results of these defects include, inter alia, elevated blood glucose or hyperglycemia. Research in the treatment of diabetes has centered on attempts to normalize fasting and postprandial blood glucose levels. Current treatments include administration of exogenous insulin, oral administration of drugs and dietary therapies.

Two major forms of diabetes mellitus are recognized. Type 1 diabetes, or insulin-dependent diabetes mellitus (IDDM), is the result of an absolute deficiency of insulin, the hormone that regulates carbohydrate utilization. Type 2 diabetes, or non-insulin-dependent diabetes mellitus (NIDDM), often occurs with normal, or even elevated, levels of insulin and appears to be the result of the inability of tissues to respond appropriately to insulin. Most Type 2 diabetic patients are also obese.

The compounds of the invention effectively lower blood glucose levels when administered orally to mammals with hyperglycemia or diabetes.

Obesity constitutes a major health risk that leads to mortality and incidence of Type 2 diabetes mellitus, hypertension, and dyslipidemia. In the United States, more than 50% of the adult population is overweight, and almost 25% of the population is considered to be obese. The incidence of obesity is increasing in the United States at a three-percent cumulative annual growth rate. While the vast majority of obesity occurs in the United States and Europe, the prevalence of obesity is also increasing in Japan. Furthermore, obesity is a devastating disease which can also wreak havoc on an individual's mental health and self-esteem, which can ultimately affect a person's ability to interact socially with others. Unfortunately, the precise etiology of obesity is complex and poorly understood, and societal stereotypes and presumptions regarding obesity only tend to exacerbate the psychological effects of the disease. Because of the impact of obesity on society in general, much effort has been expended in efforts to treat obesity, however, success in the long-term treatment and/or prevention thereof remains elusive.

The compounds, pharmaceutical compositions, and combinations of the present invention also reduce body weight, or decrease weight gain, when administered to a mammal, including a human subject. The ability of the compounds to affect weight gain is due to activation of $\beta_3$ adrenergic receptors that stimulate the metabolism of adipose tissue.

$\beta$-Adrenergic agents have been generally classified into $\beta_1$, $\beta_2$, and $\beta_3$ receptor-specific subtypes. Agonists of $\beta$-receptors promote the activation of adenyl cyclase. Activation of $\beta_1$ receptors invokes an increase in heart rate while activation of $\beta_2$ receptors induces smooth muscle tissue relaxation that produces a drop in blood pressure and the onset of skeletal muscle tremors. Activation of $\beta_3$ receptors is known to stimulate lipolysis (e.g., the breakdown of adipose tissue triglycerides into glycerol and fatty acids) and metabolic rate (energy expenditure), thereby promoting the loss of fat mass. Accordingly, compounds that stimulate $\beta_3$ receptors are therefore useful as anti-obesity agents, and can be further used to increase the content of lean meat in edible animals. In addition, compounds that are $\beta_3$ receptor agonists have hypoglycemic activity, however, the precise mechanism of this effect is presently unknown.

Until recently, $\beta_3$ adrenergic receptors were believed to be located predominantly in adipose tissue, however, such $\beta_3$ receptors are now known to be present in such diverse tissues as the intestine, (*J. Clin. Invest.*, 91, 344 (1993)) and the brain (*Eur. J. Pharm.*, 219, 193 (1992)). Stimulation of $\beta_3$ receptors has also been demonstrated to induce relaxation of smooth muscle in the colon, trachea, and bronchi. See, for example, *Life Sciences*, 44, 1411 (1989), *Br. J. Pharm.*, 112, 55 (1994), and *Br. J. Pharmacol.*, 110, 1311 (1993). Furthermore, stimulation of $\beta_3$ receptors has also been found to induce relaxation of histamine-contracted guinea pig ileum. See, for example, *J. Pharm. Exp. Ther.*, 260, 1, 192 (1992).

The $\beta_3$ receptor is also expressed in the human prostate (*J. Clin. Invest.*, 91, 344 (1993)). Because stimulation of the $\beta_3$ receptor causes relaxation of smooth muscles that have been shown to express the $\beta_3$ receptor, i.e. intestinal smooth muscle, one of ordinary skill in the art would also predict relaxation of prostate smooth muscle. Therefore, $\beta_3$ agonists are useful in the treatment or prevention of prostate disease.

U.S. Pat. No. 5,977,124 discloses certain $\beta_3$ adrenergic receptor agonists that may be used in the treatment of, inter alia, hypoglycemia and obesity.

U.S. Pat. No. 5,776,983 discloses certain catecholamines as $\beta_3$-agonists.

U.S. Pat. No. 5,030,640 discloses certain α-heterocyclic ethanol amino alkyl indoles that may be used as growth promoters, bronchodilators, anti-depressants, and anti-obesity agents.

U.S. Pat. No. 5,019,578 discloses certain α-heterocyclic ethanolamines that may be used as growth promoters.

U.S. Pat. No. 4,478,849 discloses pharmaceutical compositions comprising certain ethanolamine derivatives and methods of using such compositions in the treatment of obesity and/or hyperglycaemia.

U.S. Pat. No. 4,358,455 discloses certain heterocyclic compounds that may be used for treating glaucoma and cardiovascular disease.

U.S. Pat. No. 5,393,779 (EP 516 349 B1) discloses certain 2-hydroxyphenethyl amines that may be used as anti-obesity and hypoglycemic agents, as well as, other related utilities.

U.S. Pat. No. 5,153,210 discloses certain heterocyclic compounds that may be used as anti-obesity and anti-hyperglycaemic agents.

U.S. Pat. No. 6,251,925 discloses biaryl compounds that may be used for the treatment of diseases susceptible to amelioration by administration of an atypical beta-adrenoceptor agonist.

U.S. Publication No. 2002-0052392A1 (PCT Publication No. WO 02/32897) discloses certain heterocyclic $\beta_3$-adrenergic receptor agonists that may be used in the treatment of intestinal motility disorders, depression, prostate disease, dyslipidemia, and airway inflammatory disorders, and in increasing the content of lean meat in edible animals.

SUMMARY OF THE INVENTION

The present invention provides β$_3$-adrenergic receptor agonists of structural Formula (I)

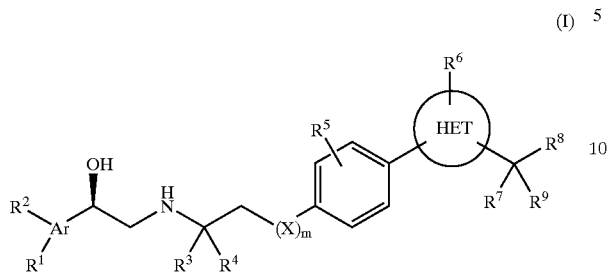

(I)

wherein

Ar is phenyl, a 5- or 6-membered aromatic or non-aromatic heterocyclic ring having 1 to 4 heteroatoms selected from O, S, or N, a benzene ring fused to a ($C_3$–$C_8$)cycloalkyl, a benzene ring fused to a 5- or 6-membered aromatic or non-aromatic heterocyclic ring having 1 to 3 heteroatoms selected from O, S, or N, or a 5- or 6-membered aromatic or non-aromatic heterocyclic ring having 1 to 3 heteroatoms selected from O, S, or N fused to a 5- or 6-membered aromatic or non-aromatic heterocyclic ring having 1 to 3 heteroatoms selected from O, S, or N (preferably, Ar is phenyl or pyridyl, more preferably pyridyl);

$R^1$ and $R^2$ are each independently hydrogen, hydroxy, halogen, cyano, nitro, —NR$^{1a}$R$^{2a}$, —NR$^{1a}$SO$_2$R$^{2a}$, —OR$^{1a}$, —SO$_2$R$^{2a}$, —CF$_3$, ($C_3$–$C_8$)cycloalkyl, phenyl, —NR$^{1a}$COR$^{2a}$, —COR$^{2a}$, or ($C_1$–$C_6$)alkyl optionally substituted with one or more substituents selected from the group consisting of hydroxy, nitro, halogen, and cyano, where R$^{1a}$ and R$^{2a}$ are each independently hydrogen, ($C_3$–$C_8$)cycloalkyl, phenyl optionally substituted with 1 to 3 substituents selected from the group consisting of halo, ($C_1$–$C_6$)alkyl, and ($C_1$–$C_6$)alkoxy, or ($C_1$–$C_6$)alkyl optionally substituted with 1 to 3 substituents selected from the group consisting of hydroxy, fluoro, —CO$_2$H, phenyl, and —NR$^{1b}$R$^{2b}$, where R$^{1b}$ and R$^{2b}$ are each independently hydrogen, amino, amino($C_1$–$C_6$)alkyl, aminoaryl, ($C_1$–$C_6$)alkyl optionally substituted with one or more substituents selected from the group consisting of hydroxy, ($C_1$–$C_6$)alkoxy, fluoro, amino, ($C_1$–$C_6$) alkylamino, and acyl, ($C_3$–$C_8$)cycloalkyl optionally substituted with one or more substituents selected from the group consisting of fluoro, alkyl, ($C_1$–$C_6$)alkoxy, hydroxy, amino, aminoalkyl-, acyl, and amido, a 3- to 8-membered aromatic or non-aromatic heterocyclic ring optionally substituted with one or more substituents selected from the group consisting of halogen, ($C_1$–$C_6$)alkyl, ($C_1$–$C_6$)alkoxy, hydroxy, amino, aminoalkyl-, acyl, and amido; or R$^{1b}$ and R$^{2b}$ taken together with the nitrogen to which they are attached form a 3-to 8-membered aromatic or non-aromatic heterocyclic ring optionally containing 1 to 2 additional heteroatoms selected from O, S, or N;

$R^3$ and $R^4$ are each, independently, hydrogen, or ($C_1$–$C_6$) alkyl optionally substituted with 1 to 3 substituents selected from the group consisting of hydroxy, ($C_1$–$C_6$) alkoxy, and fluoro;

$R^5$ is hydrogen, ($C_1$–$C_6$)alkyl optionally substituted with 1 to 3 substituents selected from the group consisting of hydroxy, ($C_1$–$C_6$)alkoxy, and fluoro;

$R^6$ and $R^7$ are each independently hydrogen, halogen, or ($C_1$–$C_6$)alkyl optionally substituted with one or more substituents selected from the group consisting of hydroxy, ($C_1$–$C_6$)alkoxy, and fluoro;

$R^8$ is —CONR$^{1b}$R$^{2b}$, —SOR$^{1b}$, —SO$_2$R$^{1b}$, —SO$_2$NR$^{1b}$R$^{2b}$, —NR$^{1b}$SO$_2$R$^{2b}$, or —CO$_2$R$^{1b}$ (preferably, R$^8$ is is —CONR$^{1b}$R$^{2b}$);

$R^9$ is hydrogen, ($C_1$–$C_6$)alkoxy, or ($C_1$–$C_6$)alkyl optionally substituted with one or more substituents selected from the group consisting of fluoro, hydroxy, and ($C_1$–$C_6$)alkoxy;

X is —O—, —NH—, —NR$^{1a}$—, —CH$_2$—, —CH$_2$CH$_2$— or —CH$_2$O— (preferably, X is —O—);

m is 0 or 1; and

HET is an aromatic heterocyclic ring selected from the group consisting of imidazole, oxazole, pyrazole, and thiazole (preferably, HET is oxazole or pyrazole, more preferably oxazole);

a pharmaceutically acceptable salt thereof, a prodrug of the compound or the salt, or a solvate or hydrate of the compound, the salt or the prodrug.

In a preferred embodiment, compounds of Formula (IA) are provided.

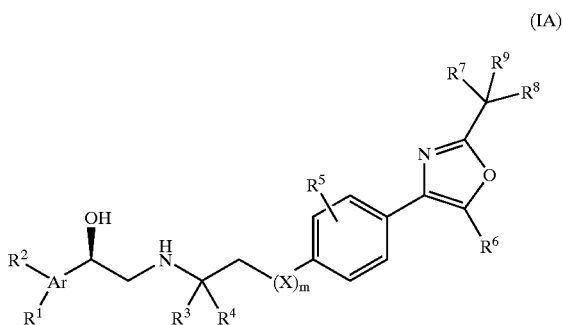

(IA)

where $R^1$, $R^2$, $R^3$, $R^4$, $R^5$, $R^6$, $R^7$, $R^8$, $R^9$, X and m are as defined above; a pharmaceutically acceptable salt thereof, a prodrug of the compound or the salt, or a solvate or hydrate of the compound, the salt or the prodrug. In preferred embodiments of the compound of Formula (IA), Ar is pyridyl (more preferably, 3-pyridyl); R$^3$, R$^4$, R$^5$, and R$^6$ are hydrogen; R$^7$ and R$^9$ are each independently hydrogen, fluoro, or ($C_1$–$C_6$) alkyl; R$^8$ is —CONR$^{1b}$R$^{2b}$ (where R$^{1b}$ and R$^{2b}$ are are each independently selected from hydrogen, ($C_3$–$C_6$) cycloalkyl, or ($C_1$–$C_6$)alkyl optionally substituted one or more fluoro, or R$^{1b}$ and R$^{2b}$ taken together with the nitrogen to which they are attached form a 4- to 6-membered non-aromatic heterocyclic ring optionally containing one additional heteroatom selected from O and N, more preferably R$^{1b}$ and R$^{2b}$ are are each independently selected from hydrogen or ($C_1$–$C_6$)alkyl, most preferably R$^{1b}$ and R$^{2b}$ are are each independently selected from hydrogen or methyl); X is —O— and m is 1; a pharmaceutically acceptable salt thereof, a prodrug of the compound or the salt, or a solvate or hydrate of the compound, the salt or the prodrug.

Preferred compounds of Formula (IA) include: 2-[4-(4-{2-[2(R)-hydroxy-2-(6-methyl-pyridin-3-yl)-ethylamino]-ethoxy}-phenyl)-oxazol-2-yl]-N,N-dimethyl-acetamide; 2-(4-{4-[2-(2(R)-hydroxy-2-pyridin-3-yl-ethylamino)-ethoxy]-phenyl}-oxazol-2-yl)-N,N-dimethyl-acetamide; N,N-diethyl-2-(4-{4-[2-(2(R)-hydroxy-2-pyridin-3-ylethylamino)-ethoxy]-phenyl}-oxazol-2-yl)-acetamide; 2-[4-(4-{2-[2-(6-chloro-pyridin-3-yl)-2(R)-hydroxy-ethylamino]-ethoxy}-phenyl)-oxazol-2-yl]-N-ethyl-N-(2,2,2-trifluoro-ethyl)-acetamide; 2-[4-(4-{2-[2-(6-chloro-pyridin-3-yl)-2(R)-hydroxy-ethylamino]-ethoxy}-phenyl)-oxazol-2-yl]-N,N-diisopropyl-acetamide; 2-[4-(4-{2-[2-(6-chloro-pyridin-3-yl)-2(R)-hydroxy-ethylamino]-ethoxy}-phenyl)-oxazol-2-yl]-N,N-dimethyl-isobutyramide; 2-(4-{4-[2-(2(R)-hydroxy-2-pyridin-3-yl-ethylamino)-ethoxy]-phenyl}-oxazol-2-yl)-N,N-dimethyl-isobutyramide; 2-(4-{4-[2-(2(R)-hydroxy-2-pyridin-3-yl-ethylamino)-ethoxy]-phenyl}-oxazol-2-yl)-N,N-dimethyl-butyramide; 2-[4-(4-{2-[2(R)-hydroxy-2-(6-methyl-pyridin-3-yl)-ethylamino]-ethoxy}-phenyl)-oxazol-2-yl]-N,N-dimethyl-propionamide; 2-[4-(4-{2-[2(R)-hydroxy-2-(6-methyl-pyridin-3-yl)-ethylamino]-ethoxy}-phenyl)-oxazol-2-yl]-N,N-dimethyl-butyramide; and 2-[4-(4-{2-[2(R)-hydroxy-2-(6-methyl-pyridin-3-yl)-ethylamino]-ethoxy}-phenyl)-oxazol-2-yl]-N,N-dimethyl-isobutyramide; a pharmaceutically acceptable salt thereof, a prodrug of the compound or the salt, or a solvate or hydrate of the compound, the salt or the prodrug.

More preferred compounds of Formula (IA) include: 2-[4-(4-{2-[2(R)-hydroxy-2-(6-methyl-pyridin-3-yl)-ethylamino]-ethoxy}-phenyl)-oxazol-2-yl]-N,N-dimethyl-acetamide; 2-(4-{4-[2-(2(R)-hydroxy-2-pyridin-3-yl-ethylamino)-ethoxy]-phenyl}-oxazol-2-yl)-N,N-dimethyl-acetamide; N,N-diethyl-2-(4-{4-[2-(2(R)-hydroxy-2-pyridin-3-yl-ethylamino)-ethoxy]-phenyl}-oxazol-2-yl)-acetamide; 2-[4-(4-{2-[2(R)-hydroxy-2-(6-methyl-pyridin-3-yl)-ethylamino]-ethoxy}-phenyl)-oxazol-2-yl]-N,N-dimethyl-propionamide; 2-[4-(4-{2-[2(R)-hydroxy-2-(6-methyl-pyridin-3-yl)-ethylamino]-ethoxy}-phenyl)-oxazol-2-yl]-N,N-dimethyl-butyramide; and 2-[4-(4-{2-[2(R)-hydroxy-2-(6-methyl-pyridin-3-yl)-ethylamino]-ethoxy}-phenyl)-oxazol-2-yl]-N,N-dimethyl-isobutyramide; a pharmaceutically acceptable salt thereof, a prodrug of the compound or the salt, or a solvate or hydrate of the compound, the salt or the prodrug.

In another preferred embodiment, compounds of Formula (IA-1) are provided.

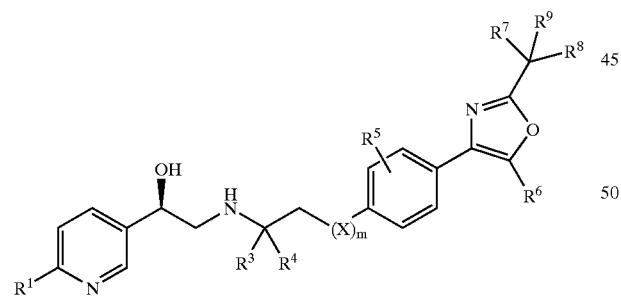

(IA-1)

wherein $R^1$ is hydrogen, hydroxy, halogen, $(C_1-C_6)$alkyl, or $(C_1-C_6)$alkoxy (preferably, $R^1$ is hydrogen, halogen or $(C_1-C_6)$alkyl); $R^3$ and $R^4$ are hydrogen; $R^5$, $R^6$, $R^7$ and $R^9$ are each independently hydrogen or $(C_1-C_6)$ alkyl optionally substituted with one or more fluoro substituents (preferably, $R^5$, $R^6$, $R^7$ and $R^9$ are all hydrogen); $R^8$ is —$CONR^{1b}R^{2b}$, where $R^{1b}$ and $R^{2b}$ are each independently selected from hydrogen, $(C_3-C_6)$ cycloalkyl or $(C_1-C_6)$alkyl optionally substituted one or more fluoro, or $R^{1a}$ and $R^{1b}$ taken together with the nitrogen to which they are attached form a 4- to 6-membered non-aromatic heterocyclic ring optionally containing one additional heteroatom selected from O or N (preferably, $R^{1a}$ and $R^{1b}$ are each independently hydrogen or $(C_1-C_6)$alkyl, more preferably $R^{1a}$ and $R^{1b}$ are each independently hydrogen or methyl); X is —O—; and m is 1; a pharmaceutically acceptable salt thereof, a prodrug of the compound or the salt, or a solvate or hydrate of the compound, the salt or the prodrug.

Preferred compounds include 2-[4-(4-{2-[2(R)-hydroxy-2-(6-methyl-pyridin-3-yl)-ethylamino]-ethoxy}-phenyl)-oxazol-2-yl]-N,N-dimethyl-acetamide; and 2-[4-(4-{2-[2(R)-hydroxy-2-(6-methyl-pyridin-3-yl)-ethylamino]-ethoxy}-phenyl)-oxazol-2-yl]-N-methyl-acetamide; or a pharmaceutically acceptable salt thereof, a solvate or hydrate of the compound or the salt.

In yet another preferred embodiment, compounds of Formula (IB) are provided.

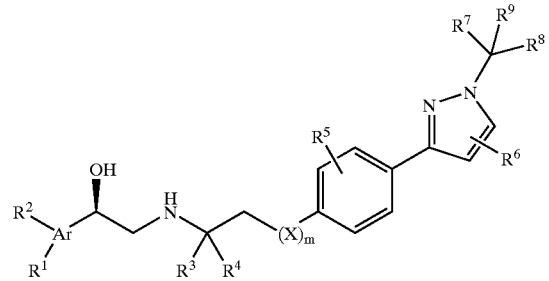

(IB)

where $R^1$, $R^2$, $R^3$, $R^4$, $R^5$, $R^7$, $R^8$, $R^9$, X and m are as defined above; a pharmaceutically acceptable salt thereof, a prodrug of the compound or the salt, or a solvate or hydrate of the compound, the salt or the prodrug. In preferred embodiments of the compound of Formula (IB), Ar is pyridyl (more preferably, 3-pyridyl); $R^3$, $R^4$, $R^5$, and $R^6$ are hydrogen; $R^7$ and $R^9$ are each independently hydrogen, fluoro, or $(C_1-C_6)$ alkyl; $R^8$ is —$CONR^{1b}R^{2b}$ (where $R^{1b}$ and $R^{2b}$ are are each independently selected from hydrogen, $(C_3-C_6)$ cycloalkyl, or $(C_1-C_6)$alkyl optionally substituted one or more fluoro, or $R^{1b}$ and $R^{2b}$ taken together with the nitrogen to which they are attached form a 4- to 6-membered non-aromatic heterocyclic ring optionally containing one additional heteroatom selected from O and N, more preferably $R^{1b}$ and $R^{2b}$ are are each independently selected from hydrogen or $(C_1-C_6)$alkyl, most preferably $R^{1b}$ and $R^{2b}$ are are each independently selected from hydrogen or methyl); X is —O— and m is 1; a pharmaceutically acceptable salt thereof, a prodrug of the compound or the salt, or a solvate or hydrate of the compound, the salt or the prodrug.

Preferred compounds of Formula (IB) include: 2-(3-{4-[2-(2(R)-hydroxy-2-pyridin-3-yl-ethylamino)-ethoxy]-phenyl}-pyrazol-1-yl)-N,N-dimethyl-acetamide; N-ethyl-2-(3-{4-[2-(2(R)-hydroxy-2-pyridin-3-yl-ethylamino)-ethoxy]-phenyl}-pyrazol-1-yl)-N-methyl-acetamide; 2-(3-{4-[2-(2(R)-hydroxy-2-pyridin-3-yl-ethylamino)-ethoxy]-phenyl}-pyrazol-1-yl)-1-morpholin-4-yl-ethanone; 2-(3-{4-[2-(2(R)-hydroxy-2-pyridin-3-yl-ethylamino)-ethoxy]-phenyl}-pyrazol-1-yl)-1-pyrrolidin-1-yl-ethanone; and N-cyclopentyl-2-(3-{4-[2-(2(R)-hydroxy-2-pyridin-3-yl-ethylamino)-ethoxy]-phenyl}-pyrazol-1-yl)-acetamide; a pharmaceutically acceptable salt thereof, a prodrug of the compound or the salt, or a solvate or hydrate of the compound, the salt or the prodrug.

In another aspect of the present invention, a pharmaceutical composition is provided which comprises (1) a compound of the present invention, and (2) a pharmaceutically acceptable excipient, diluent, or carrier. The pharmaceutical composition may further comprise an additional pharmaceutical agent. A preferred pharmaceutical agent is an anti-obesity agent selected from the group consisting of an apolipoprotein-B secretion/microsomal triglyceride transfer protein (apo-B/MTP) inhibitor, a MCR-4 agonist, a cholecystokinin-A (CCK-A) agonist, a monoamine reuptake inhibitor (e.g., sibutramine), a sympathomimetic agent, a cannabinoid receptor antagonist (e.g., rimonabant (SR-141, 716A)), a dopamine agonist (e.g., bromocriptine), a melanocyte-stimulating hormone receptor analog, a 5HT2c agonist, a melanin concentrating hormone antagonist, leptin (the OB protein), a leptin analog, a leptin receptor agonist, a galanin antagonist, a lipase inhibitor (e.g., tetrahydrolipstatin, i.e. orlistat), an anorectic agent (e.g., a bombesin agonist), a Neuropeptide-Y antagonist, a thyromimetic agent, a dehydroepiandrosterone or an analog thereof, a glucocorticoid receptor agonist or antagonist, an orexin receptor antagonist, a glucagon-like peptide-1 receptor agonist, a ciliary neurotrophic factor (e.g., Axokine™), a human agouti-related protein (AGRP), a ghrelin receptor antagonist, a histamine 3 receptor antagonist or inverse agonist, and a neuromedin U receptor agonist.

In yet another embodiment of the present invention, a method for treating a disease, condition or disorder modulated by a $\beta_3$ adrenergic receptor agonist in animals that includes the step of administering to an animal in need of such treatment a therapeutically effective amount of a compound of the present invention (or a pharmaceutical composition thereof). Diseases, conditions, and/or disorders modulated by $\beta_3$ adrenergic agonists include weight loss (e.g., increased energy expenditure), obesity, diabetes, irritable bowel syndrome, inflammatory bowel disease, esophagitis, duodenitis, Crohn's disease, proctitis, asthma, intestinal motility disorder, ulcer, gastritis, hypercholesterolemia, cardiovascular disease, urinary incontinence, depression, prostate disease, dyslipidemia, fatty liver, and airway inflammatory disorder. Accordingly, the compounds of the present invention may be used in the manufacture of a medicament for treating a disease, condition or disorder which is modulated by a $\beta_3$ adrenergic receptor antagonist.

Compounds of the present invention may be administered in combination with at least one additional pharmaceutical agent described hereinbelow. Preferred pharmaceutical agents include anti-obesity agents (described above).

The combination therapy may be administered as (a) a single pharmaceutical composition which comprises a compound of the present invention, at least one additional pharmaceutical agent described above and a pharmaceutically acceptable excipient, diluent, or carrier; or (b) two separate pharmaceutical compositions comprising (i) a first composition comprising a compound of the present invention and a pharmaceutically acceptable excipient, diluent, or carrier, and (ii) a second composition comprising at least one additional pharmaceutical agent described above and a pharmaceutically acceptable excipient, diluent, or carrier. The pharmaceutical compositions may be administered simultaneously or sequentially and in any order.

In yet another aspect of the present invention, a pharmaceutical kit is provided for use by a consumer to treat diseases, conditions and/or disorders modulated by $\beta_3$ adrenergic receptor agonists in an animal. The kit comprises a) a suitable dosage form comprising a compound of the present invention; and b) instructions describing a method of using the dosage form to treat diseases linked to the modulation of the $\beta_3$ adrenergic receptor.

In yet another embodiment of the present invention is a pharmaceutical kit comprising: a) a first dosage form comprising (i) a compound of the present invention and (ii) a pharmaceutically acceptable carrier, excipient or diluent; b) a second dosage form comprising (i) an additional pharmaceutical agent described above, and (ii) a pharmaceutically acceptable carrier, excipient or diluent; and c) a container.

In yet another aspect of the present invention, an intermediate compound having the Formula (I-a) is provided.

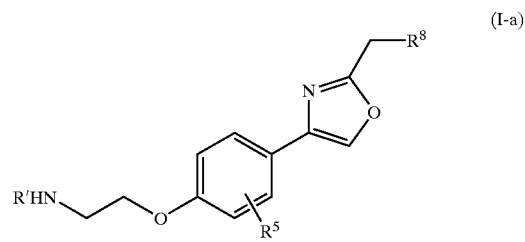

(I-a)

wherein

R' is hydrogen or an amino-protecting group;

$R^5$ is hydrogen, $(C_1–C_6)$alkyl optionally substituted with 1 to 3 substituents selected from the group consisting of hydroxy, $(C_1–C_6)$alkoxy, and fluoro; and $R^8$ is —$CONR^{1b}R^{2b}$, —$SOR^{1b}$, —$SO_2R^{1b}$, —$SO_2NR^{1b}R^{2b}$, —$NR^{1b}SO_2R^{2b}$, or —$CO_2R^{1b}$, where $R^{1b}$ and $R^{2b}$ are each independently hydrogen, amino, amino$(C_1–C_6)$alkyl, aminoaryl, $(C_1–C_6)$alkyl optionally substituted with one or more substituents selected from the group consisting of hydroxy, $(C_1–C_6)$alkoxy, fluoro, amino, $(C_1–C_6)$alkylamino, and acyl, $(C_3–C_8)$ cycloalkyl optionally substituted with one or more substituents selected from the group consisting of fluoro, alkyl, $(C_1–C_6)$alkoxy, hydroxy, amino, aminoalkyl-, acyl, and amido, a 3- to 8-membered aromatic or non-aromatic heterocyclic ring optionally substituted with one or more substituents selected from the group consisting of halogen, $(C_1–C_6)$alkyl, $(C_1–C_6)$ alkoxy, hydroxy, amino, aminoalkyl-, acyl, and amido; or $R^{1b}$ and $R^{2b}$ taken together with the nitrogen to which they are attached form a 3-to 8-membered aromatic or non-aromatic 3-to 8-membered heterocyclic ring optionally containing 1 to 2 additional heteroatoms selected from O, S, or N.

Definitions

As used herein, the term "alkyl" refers to a hydrocarbon radical of the general formula $C_nH_{2n+1}$. The alkane radical may be straight or branched. For example, the term "$(C_1–C_6)$alkyl" refers to a monovalent, straight, or branched aliphatic group containing 1 to 6 carbon atoms (e.g., methyl, ethyl, n-propyl, i-propyl, n-butyl, i-butyl, s-butyl, t-butyl, n-pentyl, 1-methylbutyl, 2-methylbutyl, 3-methylbutyl, neopentyl, 3,3-dimethylpropyl, hexyl, 2-methylpentyl, and the like). Unless specified otherwise, the alkane radical may be unsubstituted or substituted with one or more substituents (generally, one to three substituents except in the case of halogen substituents such as perchloro or perfluoroalkyls) selected from the group of substituents listed below in the definition for "substituted." For example, "halo-substituted alkyl" refers to an alkyl group substituted with one or more halogen atoms (e.g., fluoromethyl, difluoromethyl, trifluoromethyl, perfluoroethyl, and the like). Similarly, the alkyl portion of an alkoxy, alkylamino, dialkylamino, and alkylthio group has the same definition as above.

The term "cycloalkyl" refers to nonaromatic rings that are fully hydrogenated and may exist as a single ring, bicyclic ring or a spiro-fused ring. For example, cycloalkyl includes groups such as cyclopropyl, cyclobutyl, cyclopentyl, cyclohexyl, norbornyl (bicyclo[2.2.1]heptyl), bicyclo[2.2.2] octyl, and the like. Generally, the cycloalkyl ring is a 3 to 8 membered ring. Unless specified otherwise, the cycloalkyl may be optionally substituted with one of more substituents (typically, one to three substituents) selected from the group of substituents listed below in the definition for "substituted." The cycloalkyl group may be attached to the chemical entity or moiety by any one of the carbon atoms within the carbocyclic ring system. A cycloalkyl fused to a benzene ring refers to groups such as indanyl.

The term "non-aromatic heterocyclic ring" (also referred to as "heterocycle") refers to nonaromatic rings that are either partially or fully hydrogenated and may exist as a single ring, bicyclic ring or a spiro-fused ring. Partially saturated or fully saturated heterocyclic rings include groups such as epoxy, aziridinyl, tetrahydrofuranyl, dihydrofuranyl, dihydropyridinyl, pyrrolidinyl, N-methylpyrrolidinyl, imidazolidinyl, imidazolinyl, piperidinyl, piperazinyl, pyrazolidinyl, 2H-pyranyl, 4H-pyranyl, 2H-chromenyl, oxazinyl, morpholino, thiomorpholino, tetrahydrothienyl, tetrahydrothienyl 1,1-dioxide, and the like. Generally, the heterocycle is 3 to 8 membered ring containing 1 to 3 heteroatoms selected from oxygen, sulfur and nitrogen. Unless specified otherwise, the non-aromatic heterocyclic groups may be optionally substituted with one of more substituents (typically, one to three substituents) selected from the group of substituents listed below in the definition for "substituted." A heterocyclic ring that is fused to an aryl group includes groups such as 2,3-dihydrobenzofuranyl, 2,3-dihydroindolyl, 2,3-dihydrobenzothiophenyl, 2,3-dihydrobenzothiazolyl, etc. The heterocyclic group may be attached to the chemical entity or moiety by any one of the atoms within the heterocyclic ring system.

The term "aryl" refers to aromatic moieties having single (e.g., phenyl) or fused ring system (e.g., naphthalene, anthracene, phenanthrene, etc.). Unless indicated otherwise, the aryl groups may be unsubstituted or substituted with one or more substituents (preferably no more than three substituents) selected from the group of substituents listed below in the definition for "substituted." Substituted aryl groups include a chain of aromatic moieties (e.g., biphenyl, terphenyl, phenyinaphthalyl, etc.) The aryl group may be attached to the chemical entity or moiety by any one of the carbon atoms within the aromatic ring system. Preferred aryl substituents are halogens (F, Cl, Br or I, preferably F or Cl), ($C_1$–$C_4$)alkoxy, ($C_1$–$C_4$)alkyl, halo-substituted($C_1$–$C_4$)alkyl (e.g., $CH_2F$, $CHF_2$ and $CF_3$) and cyano. An aryl group fused to a cycloalkyl group includes groups such as indanyl. Similarly, the aryl portion (i.e., aromatic moiety) of an aroyl or aroyloxy (i.e., (aryl)-C(O)—O—) has the same definition as above.

The term "aromatic heterocyclic ring" or "heteroaryl" refers to aromatic moieties containing at least one heteratom (e.g., oxygen, sulfur, nitrogen or combinations thereof) within the aromatic ring system (e.g., pyrrolyl, pyridyl, pyrazolyl, indolyl, indazolyl, thienyl, furanyl, benzofuranyl, oxazolyl, oxadiazolyl, imidazolyl, tetrazolyl, triazinyl, pyrimidyl, pyrazinyl, thiazolyl, purinyl, benzimidazolyl, quinolinyl, isoquinolinyl, benzothiophenyl, benzoxazolyl, etc.). The heteroaromatic moiety may consist of a single or fused ring system. A typical single heteroaryl ring is a 5- to 6-membered ring containing one to three heteroatoms selected from oxygen, sulfur and nitrogen and a typical fused heteroaryl ring system is a 9- to 10-membered ring system containing one to four heteroatoms selected from oxygen, sulfur and nitrogen. Unless specified otherwise, the heteroaryl groups may be unsubstituted or substituted with one or more substituents (preferably no more than three substituents) selected from the group of substituents listed below in the definition for "substituted." The heteroaryl group may be attached to the chemical entity or moiety by any one of the atoms within the aromatic ring system (e.g., imidazol-1-yl, imidazol-2-yl, imidazol-4-yl, imidazol-5-yl, pyrid-2-yl, pyrid-3-yl, pyrid-4-yl, pyrid-5-yl, or pyrid-6-yl). Similarly, the heteroaryl portion (i.e., heteroaromatic moiety) of a heteroaroyl (i.e., (heteroaryl)-C(O)—O—) has the same definition as above.

The term "acyl" refers to alkyl, partially saturated or fully saturated cycloalkyl, partially saturated or fully saturated heterocycle, aryl, and heteroaryl substituted carbonyl groups. For example, acyl includes groups such as ($C_1$–$C_6$) alkanoyl (e.g., formyl, acetyl, propionyl, butyryl, valeryl, caproyl, t-butylacetyl, etc.), ($C_3$–$C_6$)cycloalkylcarbonyl (e.g., cyclopropylcarbonyl, cyclobutylcarbonyl, cyclopentylcarbonyl, cyclohexylcarbonyl, etc.), heterocyclic carbonyl (e.g., pyrrolidinylcarbonyl, pyrrolid-2-one-5-carbonyl, piperidinylcarbonyl, piperazinylcarbonyl, tetrahydrofuranylcarbonyl, etc.), aroyl (e.g., benzoyl) and heteroaroyl (e.g., thiophenyl-2-carbonyl, thiophenyl-3-carbonyl, furanyl-2-carbonyl, furanyl-3-carbonyl, 1H-pyrroyl-2-carbonyl, 1H-pyrroyl-3-carbonyl, benzo[b] thiophenyl-2-carbonyl, etc.). In addition, the alkyl, cycloalkyl, heterocycle, aryl and heteroaryl portion of the acyl group may be any one of the groups described in the respective definitions above. Unless indicated otherwise, the acyl group may be unsubstituted or optionally substituted with one of more substituents (typically, one to three substituents) selected from the group of substituents listed below in the definition for "substituted."

The term "substituted" specifically envisions and allows for one or more substitutions that are common in the art. However, it is generally understood by those skilled in the art that the substituents should be selected so as to not adversely affect the pharmacological characteristics of the compound or adversely interfere with the use of the medicament. Those skilled in the art will also appreciate that certain substitutions may be inherently unstable and therefore do not form a part of this invention. Suitable substituents for any of the groups defined above include ($C_1$–$C_6$) alkyl, partially or fully saturated ($C_3$–$C_7$)cycloalkyl, ($C_2$–$C_6$)alkenyl, aryl, heteroaryl, partially or fully saturated 3- to 6-membered heterocycle, halo (e.g., chloro, bromo, iodo and fluoro), cyano, hydroxy, ($C_1$–$C_6$)alkoxy, aryloxy, sulfhydryl (mercapto), ($C_1$–$C_6$)alkylthio, arylthio, amino, mono- or di-($C_1$–$C_6$)alkyl amino, quaternary ammonium salts, amino($C_1$–$C_6$)alkoxy, aminocarboxylate (i.e., —NH—C(O)—O—($C_1$–$C_6$)alkyl), N—($C_1$–$C_6$) alkylaminocarboxylate, hydroxy($C_1$–$C_6$)alkylamino, amino ($C_1$–$C_6$)alkylthio, cyanoamino, formamido, acylamino (e.g., acetamido and benzamido), N—($C_1$–$C_6$)alkyl-acylamino (e.g., N-methylacetamido), nitro, ($C_1$–$C_6$)carbamyl, keto (oxy), acyl, ($C_1$–$C_6$)alkoxycarbonyl, aryloxycarbonyl, ($C_1$–$C_6$)carboxy, glycolyl, glycyl, hydrazino, guanyl, sulfamyl, sulfonyl, sulfinyl, thio($C_1$–$C_6$)carbonyl, thio ($C_1$–$C_6$)carboxy, and combinations thereof. In the case of substituted combinations, such as "substituted aryl($C_1$–$C_6$) alkyl", either the aryl or the alkyl group may be substituted, or both the aryl and the alkyl groups may be substituted with one or more substituents (typically, one to three substituents except in the case of perhalo substitutions). An aryl substituted carbocyclic or heterocyclic group may be a fused ring (e.g., indanyl, dihydrobenzofuranyl, dihydroindolyl, etc.). A cycloalkyl substituted carbocyclic or heterocyclic group may be a spiro-fused ring.

The term "solvate" refers to a molecular complex of a compound of the present invention with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The term "protecting group" or "Pg" refers to a substituent that is commonly employed to block or protect a particular functionality while reacting other functional groups on the compound. For example, an "amino-protecting group" is a substituent attached to an amino group that blocks or protects the amino functionality in the compound. Suitable amino-protecting groups include acetyl, trifluoroacetyl, t-butoxycarbonyl (BOC), benzyloxycarbonyl (CBz) and 9-fluorenylmethylenoxycarbonyl (Fmoc). Similarly, a "hydroxy-protecting group" refers to a substituent of a hydroxy group that blocks or protects the hydroxy functionality. Suitable protecting groups include acetyl and silyl. A "carboxy-protecting group" refers to a substituent of the carboxy group that blocks or protects the carboxy functionality. Common carboxy-protecting groups include —$CH_2CH_2SO_2Ph$, cyanoethyl, 2-(trimethylsilyl)ethyl, 2-(trimethylsilyl)ethoxy-methyl, 2-(p-toluenesulfonyl)ethyl, 2-(p-nitrophenylsulfenyl)ethyl, 2-(diphenylphosphino)-ethyl, nitroethyl and the like. For a general description of protecting groups and their use, see T. W. Greene, *Protective Groups in Organic Synthesis*, John Wiley & Sons, New York, 1991.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The term "animal" refers to humans (male and female), companion animals (e.g., dogs, cats and horses), food-source animals, zoo animals, marine animals, birds and other similar animal species. "Edible animals" refers to food-source animals such as cows, pigs, sheep and poultry.

The phrase "pharmaceutically acceptable" indicates that the substance or composition is compatible chemically and/or toxicologically with the other ingredients comprising a formulation and/or the animal being treated therewith.

The phrase "modulated by a $β_3$ adrenergic receptor" or "modulation of a $β_3$ adrenergic receptor" refers to the activation or deactivation of $β_3$ adrenergic receptors. For example, a $β_3$ adrenergic receptor ligand may act as an agonist, partial agonist, inverse agonist, antagonist, partial antagonist, and the like.

The term "agonist" refers to both full and partial agonists.

The terms "treating", "treat", or "treatment" embrace both preventative, i.e., prophylactic, and palliative treatment.

The term "compounds of the present invention" (unless specifically identified otherwise) refer to compounds of Formula (I), (IA), (IA-1), and (IB) prodrugs thereof, pharmaceutically acceptable salts of the compounds, and/or prodrugs, and hydrates or solvates of the compounds, salts, and/or prodrugs, as well as, all stereoisomers (including diastereoisomers and enantiomers), tautomers and isotopically labeled compounds.

DETAILED DESCRIPTION

The present invention provides compounds and pharmaceutical formulations thereof that are useful in the treatment of diseases, conditions and/or disorders modulated by $β3$ adrenergic receptor agonists.

Compounds of the present invention may be synthesized by synthetic routes that include processes analogous to those well-known in the chemical arts, particularly in light of the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v. 1–19, Wiley, N.Y. (1967–1999 ed.), or *Beilsteins Handbuch der organischen Chemie*, 4, Aufl. ed. Springer-Verlag, Berlin, including supplements (also available via the *Beilstein* online database)).

For illustrative purposes, the reaction schemes depicted below provide potential routes for synthesizing the compounds of the present invention as well as key intermediates. For a more detailed description of the individual reaction steps, see the Examples section below. Those skilled in the art will appreciate that other synthetic routes may be used to synthesize the inventive compounds. Although specific starting materials and reagents are depicted in the schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

In the preparation of compounds of the present invention, protection of remote functionality (e.g., primary or secondary amine) of intermediates may be necessary. The need for such protection will vary depending on the nature of the remote functionality and the conditions of the preparation methods. Suitable amino-protecting groups (NH-Pg) include acetyl, trifluoroacetyl, t-butoxycarbonyl (BOC), benzyloxycarbonyl (CBz) and 9-fluorenylmethyleneoxycarbonyl (Fmoc). The need for such protection is readily determined by one skilled in the art. For a general description of protecting groups and their use, see T. W. Greene, *Protective Groups in Organic Synthesis*, John Wiley & Sons, New York, 1991. Scheme 1 illustrates one means for preparing a compound of the present invention where HET is an oxazole.

Scheme 1

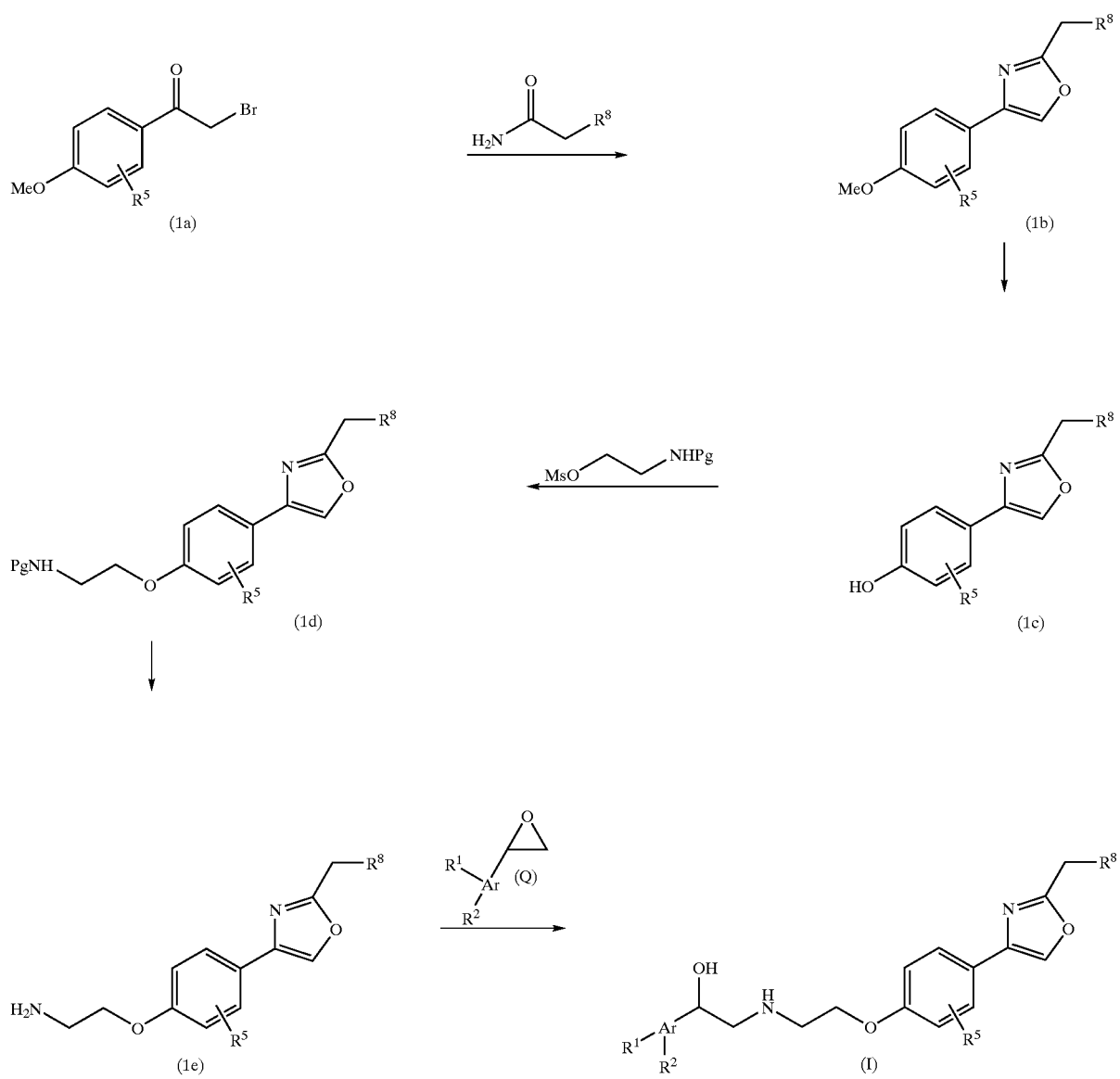

In Scheme 1 above, an α-bromoketone (1a) is cyclocondensed with an appropriately substituted amide to provide oxazole (1b). The cyclocondensation is typically conducted at elevated temperature in a polar protic or aprotic solvent (e.g., dimethylformamide or N-methylpyrrolidine). The α-bromoketone (1a) starting material may be prepared by conventional methods, for example, according to those methods disclosed in Scheme 2 below for the conversion of a protected acetophenone derivative (2b) to α-bromoketone (2c). The intermediate oxazole (1b) is then demethylated, preferably with methanesulfonic acid/methionine under standard conditions to provide phenol (1c), which is then functionalized with methanesulfonic acid 2-phenoxycarbonylamino-ethyl ester in the presence of a weak base (e.g., potassium carbonate) in an aprotic solvent (e.g., dimethylsulfoxide) to afford the protected amine (1d). The protected amine (1d) is then deprotected, preferably by catalytic hydrogenation in a polar protic solvent to provide amine (1e). Coupling of amine (1e) with a substituted oxirane derivative (Q) affords an oxazole derivative (a compound of the present invention where HET is oxazole). The oxirane intermediates may be prepared according to methods well-known to those skilled in the art, such as those described in U.S. Pat. Nos. 5,541,197; 5,561,142; 5,705,515; and 6,037,362, all of which are incorporated herein by reference. Certain oxirane derivatives are also commercially available.

Alternatively, compounds of the present invention where HET is oxazole may be prepared according to the procedures outlined in Scheme 2 below.

Scheme 2

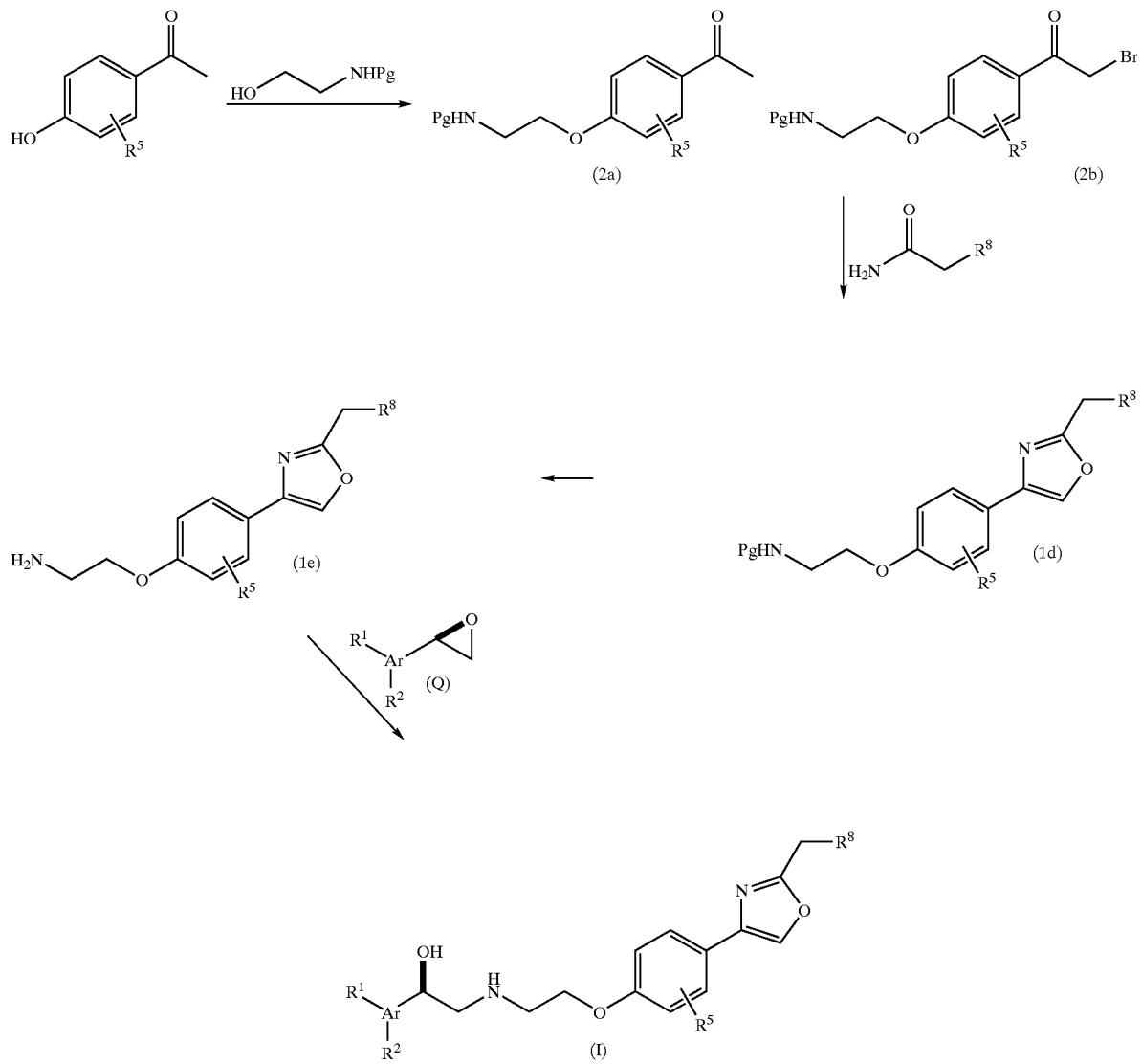

As outlined in Scheme 2 above, 4-hydroxyacetophenone is condensed with a protected N-(2-hydroxyethyl)-carbamate to form the protected acetophenone derivative (2a). The condensation may be accomplished according to methodologies that are well-known to those skilled in the art. Preferably, the condensation is effected via a Mitsunobu reaction. This reaction is typically performed with stirring at room temperature (or at elevated temperature if required) in the presence of a dehydrating reagent (e.g., a stoichiometric amount of a diazocarboxyl compound, e.g., 1,1'-(azodicarbonyl)-dipiperidine (ADDP), and a phosphine, e.g., triphenylphosphine). The condensation reaction may be carried out in any reaction-inert solvent (e.g., tetrahydrofuran, dimethylformamide, a hydrocarbon, or halogenated hydrocarbon solvent). The protected acetophenone derivative (2a) is then (α-brominated to provide α-bromoketone (2b). The bromination is performed according to conventional methods, preferably by the reaction of (2a) with tetrabutylammonium tribromide (TBA Br$_3$). Compound (2b) is cyclocondensed with an appropriately substituted amide to afford the protected oxazole (1d) which is then deprotected to afford the amine (1e). Such deprotection may be accomplished using conventional deprotection methods. For example, when Pg is a benzyl group, then the benzyl group may be removed by treating with methanesulfonic acid, or various other deprotecting agents using standard conditions well-known to those skilled in the art. Preferably, the deprotection is performed by hydrogenolysis in the presence of a suitable metal catalyst (e.g., palladium on carbon) in an inert solvent. Amine (1e) is then coupled with an appropriately substituted oxirane derivative (Q) to provide compounds of the present invention where HET is an oxazole.

Compounds of the present invention where HET is a pyrazole moiety may be prepared by the synthetic routes outlined below in Schemes 3 and 4.

Scheme 3

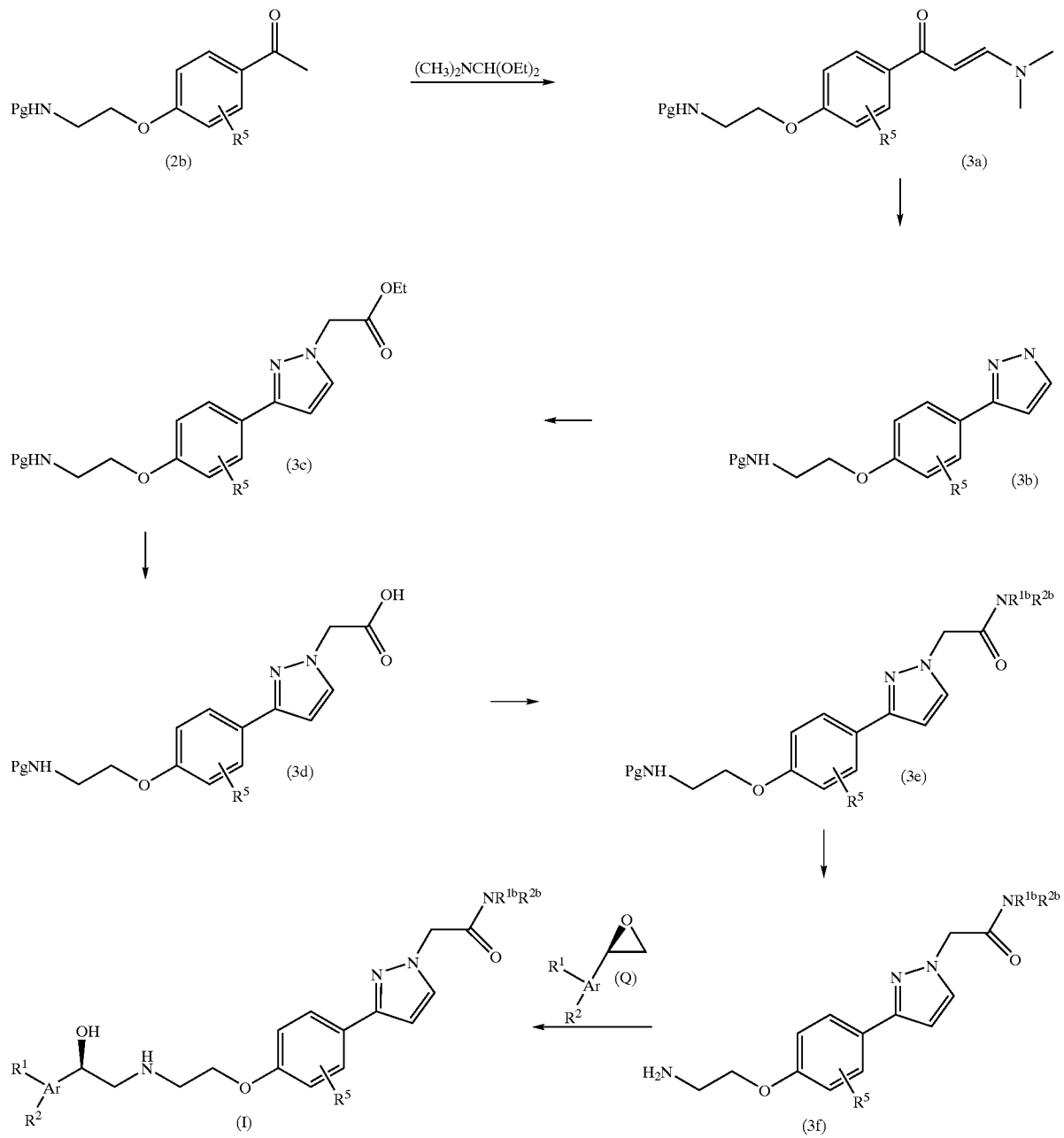

In Scheme 3 above, the protected amine (2b) is heated with N,N-dimethylformamide diethyl acetal to afford the protected amine (3a). Preferably, the reaction between the protected amine (2b) and N,N-dimethylformamide diethylacetal is achieved by simply combining both reactants together neat and heating the resulting mixture for an extended period of time, generally for about twenty-four to about forty-eight hours. The resulting product is then precipitated by the addition of a non-polar solvent (e.g., hexanes). The subsequent cyclocondensation of (3a) with hydrazine hydrate is preferably achieved by combining the reactants in a polar protic solvent (e.g., ethanol) and heating the mixture for about twelve to about twenty-four hours. The resulting pyrazole (3b) is then N-alkylated with ethyl bromoacetate, preferably in the presence of a base (e.g., sodium ethoxide) in a polar protic solvent (e.g., ethanol) to provide acetate (3c). Basic saponification of (3c), preferably with lithium hydroxide in tetrahydrofuran, affords acid (3d) which is then reacted with an appropriately substituted amine in the presence of 1-(3-dimethylaminopropyl)-3-ethylcarbodiimide hydrochloride (EDC) and 1-hydroxybenzotriazole (HOBT) to form amide (3e). Deprotection of (3e) as described in Scheme 2 above, followed by coupling with a substituted oxirane derivative (Q), affords a compound of the present invention where HET is a pyrazole.

Alternatively, compounds of the present invention where HET is pyrazole may be prepared according to the procedures outlined in Scheme 4 below.

Scheme 4

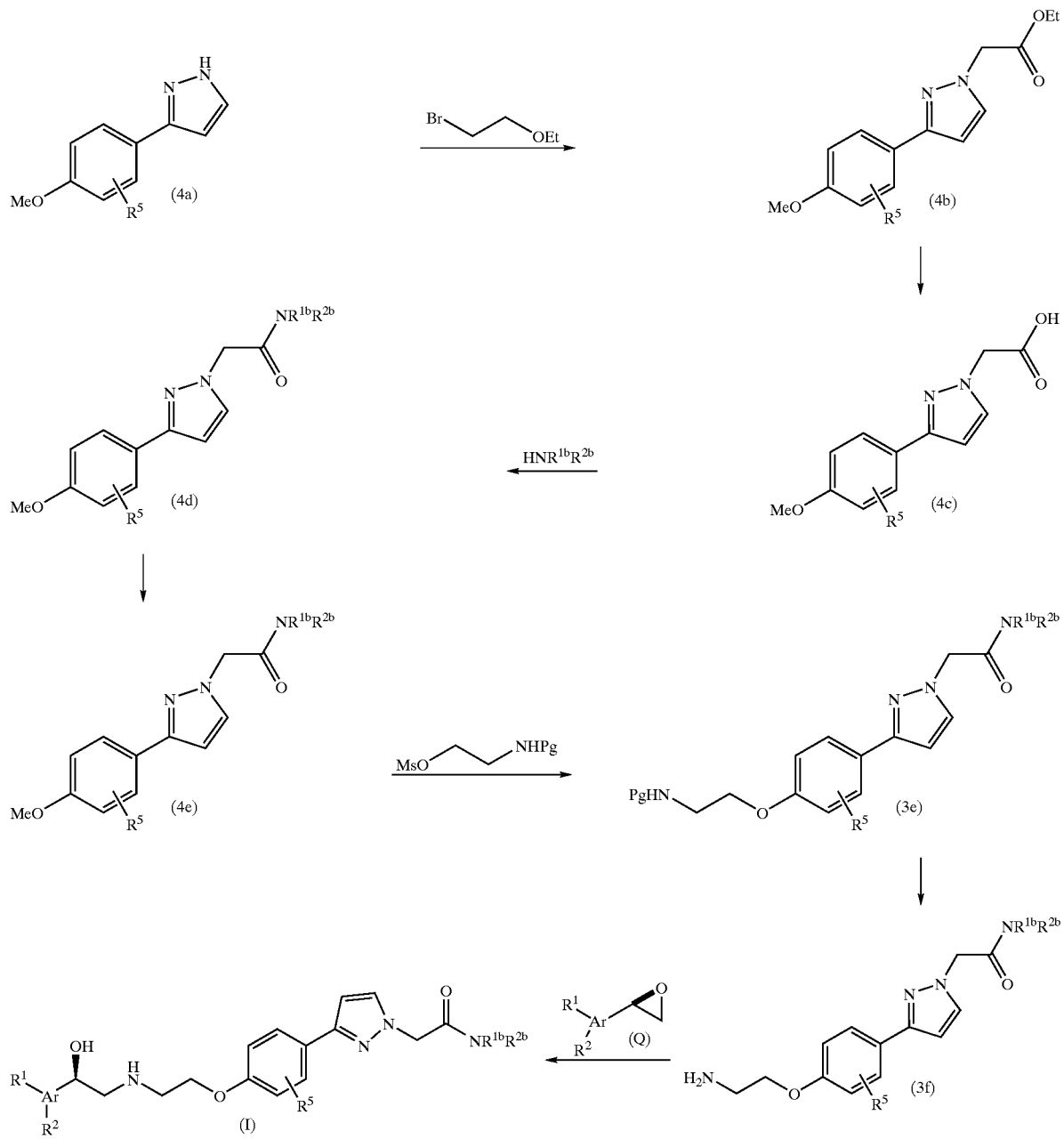

In Scheme 4 above, the commercially available pyrazolo-anisole derivative (4a) is N-alkylated with ethyl bromoacetate to provide acetate (4b), which is then saponified with base (e.g., sodium hydroxide) in an aqueous solvent system (e.g., aqueous tetrahydrofuran) to provide acid (4c). Amide (4d) is then prepared by reacting acid (4c) with an appropriately substituted amine, preferably in an inert solvent (e.g., 1,2-dichloroethane) in the presence of benzotriazole-1-yl-oxy-tris-pyrrolidino-phosphonium hexafluroide (PyBop). Demethyation of amide (4d), as described above in Scheme 1, affords phenol (4e) which is subsequently condensed with methanesulfonic acid 2-phenoxycarbonylamino-ethyl ester to provide the protected amine (3e). Catalytic deprotection of (3e), preferably with palladium on carbon in a protic solvent (e.g., methanol), affords amine (3f) which is subsequently coupled with an appropriately substituted epoxide (Q) to afford a compound of the present invention where HET is a pyrazole.

In the preceding reaction schematics, the oxazole and pyrazole residues disclosed contain substitutents that are limited to an $R^8$ moiety. Methods for preparing other heterocyclic congeners comprising $R^7$ and/or $R^9$ moieties is outlined in Scheme 5 below. One of ordinary skill in the art will appreciate that the methylene linking group interposed between the HET and $R^8$ groups of the intermediate compound (5a) depicted in Scheme 5 contains at least one acidic hydrogen atom which may be displaced and substituted with an $R^7$ and/or $R^9$ group(s). In compound (5a), Pg represents a conventional O-protecting group, (e.g., methyl, benzyl, tetrahydropyranyl, and the like) and HET is as defined above. Preferably HET denotes an oxazole, pyrazole, or thiazole heterocyclic moiety. In the instance where HET is an imidazole, the NH functional group of such residue should be appropriately protected using conventional protection schemes described earlier.

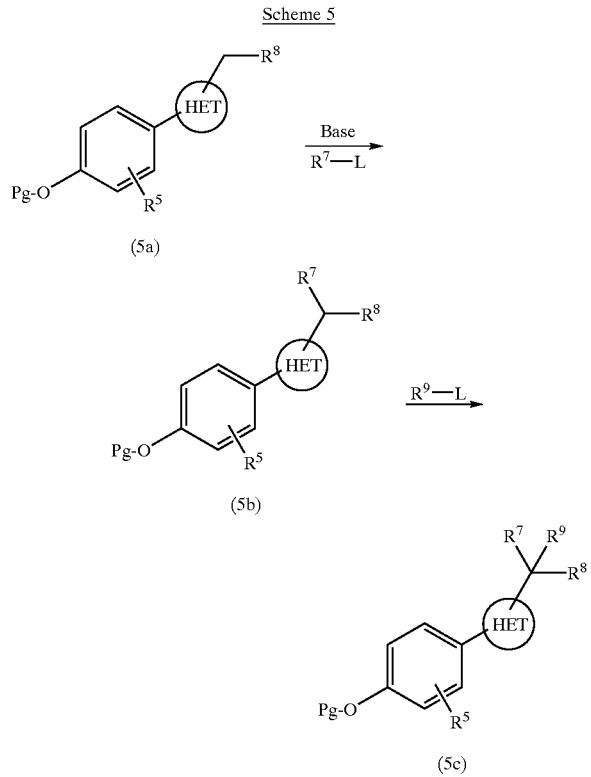

Scheme 5

(5a)

(5b)

(5c)

In Scheme 5 above, the active methylene group of compound (5a) is deprotonated with a suitable base and the resulting anion(s) treated with an appropriate reagent containing a leaving group (e.g., $R^7$-L and/or $R^9$-L, wherein $R^7$ and $R^9$ are as defined above, except that $R^7$ and $R^9$ are neither hydrogen nor halogen) to afford the functionalized, protected phenol derivative (5b). Suitable leaving groups include halogen (preferably bromo, or iodo), triflate, and the like. The deprotonation is normally accomplished with a strong base (e.g., lithium diisopropylamide, sodium hydride, lithium carbonate, lithium bis(trimethylsilyl)amide, and the like) in a reaction-inert solvent (e.g., tetrahydrofuran or ether). Preferably, the deprotonation is accomplished with lithium bis(trimethylsilyl)amide in tetrahydrofuran. The exact stoichiometric amounts of base and $R^7$-L and/or $R^9$-L employed will dictate whether compound (5b) is further functionalized to form compound (5c). Although the preparation of compound (5c) has been depicted in Scheme 5 as a separate reaction sequence involving a distinct intermediate (5b), it is generally preferred that, when $R^7$ and $R^9$ are identical, compound (5c) is generated in a one-pot process. For a more detailed description of the deprotonation and functionalization sequence depicted in Scheme 5 see the preparation of Intermediate 1-3a in the Examples section below.

The protected phenol derivative(s) (5b) and/or (5c) may then be deprotected according to conventional methods well-known to those skilled in the art, including those methods disclosed above. Functionalization, followed by coupling with a substituted oxirane derivative (Q) according to the methods disclosed above in Schemes 1 through 4 provides a compound of the present invention.

Exemplification of the coupling reaction between an oxirane derivative (Q) and an appropriately-substituted amine may be found in Example 1A-1 of the Examples section below. Alternatively, compounds of the present invention may be prepared by dehalogenation of a coupled compound of the present invention where Ar is a 2-chloro-substituted pyridine derivative, an example of which is exemplified in Example 1A-2 of the Examples section below.

Conventional methods and/or techniques of separation and purification known to one of ordinary skill in the art can be used to isolate the compounds of the present invention, as well as the various intermediates related thereto. Such techniques will be well-known to one of ordinary skill in the art and may include, for example, all types of chromatography (high pressure liquid chromatography (HPLC), column chromatography using common adsorbents such as silica gel, and thin-layer chromatography), recrystallization, and differential (i.e., liquid-liquid) extraction techniques.

The compounds of the present invention may be isolated and used per se or in the form of its pharmaceutically acceptable salt, solvate and/or hydrate. The term "salts" refers to inorganic and organic salts of a compound of the present invention. These salts can be prepared in situ during the final isolation and purification of a compound, or by separately reacting the compound, N-oxide, or prodrug with a suitable organic or inorganic acid and isolating the salt thus formed. Representative salts include the hydrobromide, hydrochloride, hydroiodide, sulfate, bisulfate, nitrate, acetate, trifluoroacetate, oxalate, besylate, palmitiate, pamoate, malonate, stearate, laurate, malate, borate, benzoate, lactate, phosphate, hexafluorophosphate, benzene sulfonate, tosylate, formate, citrate, maleate, fumarate, succinate, tartrate, naphthylate, mesylate, glucoheptonate, lactobionate, and laurylsulphonate salts, and the like. These may include cations based on the alkali and alkaline earth metals, such as sodium, lithium, potassium, calcium, magnesium, and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. See, e.g., Berge, et al., *J. Pharm. Sci.,* 66, 1–19 (1977).

The term "prodrug" means a compound that is transformed in vivo to yield a compound of Formula (I) or a pharmaceutically acceptable salt, hydrate or solvate of the compound. The transformation may occur by various mechanisms, such as through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of the present invention contains a carboxylic acid functional group, a prodrug can comprise an ester formed by the replacement of the hydrogen atom of the acid group with a group such as ($C_1$–$C_8$) alkyl, ($C_2$–$C_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino) ethyl having from 4 to 10 carbon atoms, 3-phthalidyl, 4-crotonolactonyl, gamma-butyrolacton-4-yl, di-N,N-($C_1$–$C_2$)alkylamino($C_2$–$C_3$)alkyl (such as β-dimethylaminoethyl), carbamoyl-($C_1$–$C_2$)alkyl, N,N-di ($C_1$–$C_2$)alkylcarbamoyl-($C_1$–$C_2$)alkyl and piperidino-, pyrrolidino- or morpholino($C_2$–$C_3$)alkyl.

Similarly, if a compound of the present invention contains an alcohol functional group, a prodrug can be formed by the replacement of the hydrogen atom of the alcohol group with a group such as ($C_1$–$C_6$)alkanoyloxymethyl, 1-(($C_1$–$C_6$)alkanoyloxy)ethyl, 1-methyl-1-(($C_1$–$C_6$)alkanoyloxy)ethyl, ($C_1$–$C_6$)alkoxycarbonyloxymethyl, N—($C_1$–$C_6$)alkoxycarbonylaminomethyl, succinoyl, ($C_1$–$C_6$)alkanoyl, α-amino($C_1$–$C_4$)alkanoyl, arylacyl and α-aminoacyl, or α-aminoacyl-α-aminoacyl, where each α-aminoacyl group is independently selected from the naturally occurring L-amino acids, P(O)(OH)$_2$, P(O)(O($C_1$–$C_6$)alkyl)$_2$ or glycosyl (the radical resulting from the removal of a hydroxyl group of the hemiacetal form of a carbohydrate).

If a compound of the present invention incorporates an amine functional group, a prodrug can be formed by the replacement of a hydrogen atom in the amine group with a group such as R-carbonyl, RO-carbonyl, NRR'-carbonyl where R and R' are each independently ($C_1$–$C_{10}$)alkyl, ($C_3$–$C_7$)cycloalkyl, benzyl, or R-carbonyl is a natural α-aminoacyl or natural α-aminoacyl-natural α-aminoacyl, —C(OH)C(O)OY' wherein Y' is H, ($C_1$–$C_6$)alkyl or benzyl, —C(OY$_0$)Y$_1$ wherein Y$_0$ is ($C_1$–$C_4$) alkyl and Y$_1$ is ($C_1$–$C_6$) alkyl, carboxy($C_1$–$C_6$)alkyl, amino($C_1$–$C_4$)alkyl or mono-N- or di-N,N—($C_1$–$C_6$)alkylaminoalkyl, —C(Y$_2$)Y$_3$ wherein Y$_2$ is H or methyl and Y$_3$ is mono-N- or di-N,N—($C_1$–$C_6$)alkylamino, morpholino, piperidin-1-yl or pyrrolidin-1-yl.

The compounds of the present invention may contain asymmetric or chiral centers, and, therefore, exist in different stereoisomeric forms. It is intended that all stereoisomeric forms of the compounds of the present invention as well as mixtures thereof, including racemic mixtures, form part of the present invention. In addition, the present invention embraces all geometric and positional isomers. For example, if a compound of the present invention incorporates a double bond or a fused ring, both the cis- and trans-forms, as well as mixtures, are embraced within the scope of the invention. Both the single positional isomers and mixture of positional isomers resulting from the N-oxidation of the pyrimidine and pyrazine rings are also within the scope of the present invention.

Diastereomeric mixtures can be separated into their individual diastereoisomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereoisomers and converting (e.g., hydrolyzing) the individual diastereoisomers to the corresponding pure enantiomers. Also, some of the compounds of the present invention may be atropisomers (e.g., substituted biaryls) and are considered as part of this invention. Enantiomers can also be separated by use of a chiral HPLC column.

The compounds of the present invention may exist in unsolvated as well as solvated forms with pharmaceutically acceptable solvents such as water, ethanol, and the like, and it is intended that the invention embrace both solvated and unsolvated forms.

It is also possible that the compounds of the present invention may exist in different tautomeric forms, and all such forms are embraced within the scope of the invention. For example, all of the tautomeric forms of the imidazole and pyrazole moieties are included in the invention. Also, for example, all keto-enol and imine-enamine forms of the compounds are included in the invention.

The present invention also embraces isotopically-labeled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine, iodine, and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, 123I, and $^{36}$Cl, respectively.

Certain isotopically-labeled compounds of the present invention (e.g., those labeled with $^3$H and $^{14}$C) are useful in compound and/or substrate tissue distribution assays. Tritiated (i.e., $^3$H) and carbon-14 (i.e., $^{14}$C) isotopes are particularly preferred for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Isotopically labeled compounds of the present invention can generally be prepared by following procedures analogous to those disclosed in the Schemes and/or in the Examples hereinbelow, by substituting an isotopically labeled reagent for a non-isotopically labeled reagent.

Compounds of the present invention are useful for treating diseases, conditions and/or disorders modulated by β$_3$ adrenergic receptor agonists; therefore, another embodiment of the present invention is a pharmaceutical composition comprising a therapeutically effective amount of a compound of the present invention and a pharmaceutically acceptable excipient, diluent or carrier.

A typical formulation is prepared by mixing a compound of the present invention and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water, and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG400, PEG300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., compound of the present invention or stabilized form of the compound (e.g., complex with a cyclodextrin derivative or other known complexation agent)) is dissolved in a suitable solvent in the presence of one or more of the excipients described above. The compound of the present invention is typically formulated into pharmaceutical dosage forms to provide an easily controllable dosage of the drug and to give the patient an elegant and easily handleable product.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

The present invention further provides a method of treating diseases, conditions and/or disorders modulated by $\beta_3$ adrenergic receptor agonists in an animal that includes administering to an animal in need of such treatment a therapeutically effective amount of a compound of the present invention or a pharmaceutical composition comprising an effective amount of a compound of the present invention and a pharmaceutically acceptable excipient, diluent, or carrier.

Investigations of $\beta_3$ adrenergic agonists have indicated that the following diseases, disorders and/or conditions are modulated by $\beta_3$ adrenergic agonists: weight loss (e.g., increased energy expenditure), obesity, diabetes, irritable bowel syndrome, inflammatory bowel disease, esophagitis, duodenitis, Crohn's disease, proctitis, asthma, intestinal motility disorder, ulcer, gastritis, hypercholesterolemia, cardiovascular disease, urinary incontinence, depression, prostate disease, dyslipidemia, fatty liver, and airway inflammatory disorder.

Accordingly, the compounds of the present invention described herein are useful in treating diseases, conditions, or disorders that are modulated by $\beta_3$ adrenergic receptor agonists. Consequently, the compounds of the present invention (including the compositions and processes used therein) may be used in the manufacture of a medicament for the therapeutic applications described herein.

The compounds of the present invention can be administered to a patient at dosage levels in the range of from about 0.7 mg to about 7,000 mg per day. For a normal adult human having a body weight of about 70 kg, a dosage in the range of from about 0.01 mg to about 100 mg per kilogram body weight is typically sufficient. However, some variability in the general dosage range may be required depending upon the age and weight of the subject being treated, the intended route of administration, the particular compound being administered and the like. The determination of dosage ranges and optimal dosages for a particular patient is well within the ability of one of ordinary skill in the art having the benefit of the instant disclosure. It is also noted that the compounds of the present invention can be used in sustained release, controlled release, and delayed release formulations, which forms are also well known to one of ordinary skill in the art.

The compounds of this invention may also be used in conjunction with other pharmaceutical agents for the treatment of the diseases, conditions and/or disorders described herein. Therefore, methods of treatment that include administering compounds of the present invention in combination with other pharmaceutical agents are also provided. Suitable pharmaceutical agents that may be used in combination with the compounds of the present invention include anti-obesity agents such as apolipoprotein-B secretion/microsomal triglyceride transfer protein (apo-B/MTP) inhibitors, MCR-4 agonists, cholecystokinin-A (CCK-A) agonists, monoamine reuptake inhibitors (e.g., sibutramine), sympathomimetic agents, cannabinoid receptor antagonists (e.g., rimonabant (SR-141,716A)), dopamine agonists (e.g., bromocriptine), melanocyte-stimulating hormone receptor analogs, 5HT2c agonists, melanin concentrating hormone antagonists, leptin (the OB protein), leptin analogs, leptin receptor agonists, galanin antagonists, lipase inhibitors (e.g., tetrahydrolipstatin, i.e. orlistat), anorectic agents (e.g., a bombesin agonist), Neuropeptide-Y antagonists, thyromimetic agents, dehydroepiandrosterone or an analog thereof, glucocorticoid receptor agonists or antagonists, orexin receptor antagonists, glucagon-like peptide-1 receptor agonists, ciliary neurotrophic factors (e.g., Axokine™ available from Regeneron Pharmaceuticals, Inc., Tarrytown, N.Y. and Procter & Gamble Company, Cincinnati, Ohio), human agouti-related proteins (AGRP), ghrelin receptor antagonists, histamine 3 receptor antagonists or inverse agonists, neuromedin U receptor agonists and the like. Other anti-obesity agents, including the preferred agents set forth hereinbelow, are well known, or will be readily apparent in light of the instant disclosure, to one of ordinary skill in the art.

Especially preferred are anti-obesity agents selected from the group consisting of orlistat, sibutramine, bromocriptine, ephedrine, leptin, and pseudoephedrine. Preferably, compounds of the present invention and combination therapies are administered in conjunction with exercise and a sensible diet.

Representative anti-obesity agents for use in the combinations, pharmaceutical compositions, and methods of the invention can be prepared using methods known to one of ordinary skill in the art, for example, sibutramine can be prepared as described in U.S. Pat. No. 4,929,629; bromocriptine can be prepared as described in U.S. Pat. Nos. 3,752,814 and 3,752,888; and orlistat can be prepared as described in U.S. Pat. Nos. 5,274,143; 5,420,305; 5,540,917; and 5,643,874. All of the above recited U.S. patents are incorporated herein by reference.

Other pharmaceutical agents that may be useful include antihypertensive agents; antidepressants; insulin and insulin analogs (e.g., LysPro insulin); GLP-1 (7–37) (insulinotropin) and GLP-1 (7–36)-NH$_2$; sulfonylureas and analogs thereof: chlorpropamide, glibenclamide, tolbutamide, tolazamide, acetohexamide, Glypizide®, glimepiride, repaglinide, meglitinide; biguanides: metformin, phenformin, buformin; α2-antagonists and imidazolines: midaglizole, isaglidole, deriglidole, idazoxan, efaroxan, fluparoxan; other insulin secretagogues: linogliride, A-4166; glitazones: ciglitazone, Actos® (pioglitazone), englitazone, troglitazone, darglitazone, Avandia® (BRL49653); fatty acid oxidation inhibitors: clomoxir, etomoxir; α-glucosidase inhibitors: acarbose, miglitol, emiglitate, voglibose, MDL-25,637, camiglibose, MDL-73,945; β-agonists: BRL 35135, BRL 37344, RO 16-8714, ICI D7114, CL 316,243; phosphodiesterase inhibitors: L-386,398; lipid-lowering agents: benfluorex: fenfluramine; vanadate and vanadium complexes (e.g., Naglivan®) and peroxovanadium complexes; amylin antagonists; glucagon antagonists; gluconeogenesis inhibitors; somatostatin analogs; antilipolytic agents: nicotinic acid, acipimox, WAG 994, pramlintide (Symlin™), AC 2993, nateglinide, aldose reductase inhibitors (e.g., zopolrestat), glycogen phosphorylase inhibitors, sorbitol dehydrogenase inhibitors, sodium-hydrogen exchanger type 1 (NHE-1) inhibitors and/or cholesterol biosynthesis inhibitors or cholesterol absorption inhibitors, especially a HMG-CoA reductase inhibitor, or a HMG-CoA synthase inhibitor, or a HMG-CoA reductase or synthase gene expression inhibitor, a CETP inhibitor, a bile acid sequesterant, a fibrate, an ACAT inhibitor, a squalene synthetase inhibitor, an anti-oxidant or niacin. The compounds of the present invention may also be administered in combination with a naturally occurring compound that acts to lower plasma cholesterol levels. Such naturally occurring compounds are commonly called nutraceuticals and include, for example, garlic extract, Hoodia plant extracts, and niacin.

The dosage of the additional pharmaceutical agent will also be generally dependent upon a number of factors including the health of the subject being treated, the extent of treatment desired, the nature and kind of concurrent therapy, if any, and the frequency of treatment and the nature of the effect desired. In general, the dosage range of an anti-obesity agent is in the range of from about 0.001 mg to about 100 mg per kilogram body weight of the individual per day, preferably from about 0.1 mg to about 10 mg per kilogram body weight of the individual per day. However, some variability in the general dosage range may also be required depending upon the age and weight of the subject being treated, the intended route of administration, the particular anti-obesity agent being administered and the like. The determination of dosage ranges and optimal dosages for a particular patient is also well within the ability of one of ordinary skill in the art having the benefit of the instant disclosure.

According to the methods of the invention, a compound of the present invention or a combination of a compound of the present invention and at least one additional pharmaceutical agent is administered to a subject in need of such treatment, preferably in the form of a pharmaceutical composition. In the combination aspect of the invention, the compound of the present invention and at least one other pharmaceutical agent may be administered either separately or in the pharmaceutical composition comprising both. It is generally preferred that such administration be oral. However, if the subject being treated is unable to swallow, or oral administration is otherwise impaired or undesirable, parenteral or transdermal administration may be appropriate. According to the methods of the invention, when a combination of a compound of the present invention and at least one other pharmaceutical agent are administered together, such administration can be sequential in time or simultaneous with the simultaneous method being generally preferred. For sequential administration, a compound of the present invention and the additional pharmaceutical agent can be administered in any order. It is generally preferred that such administration be oral. It is especially preferred that such administration be oral and simultaneous. When a compound of the present invention and the additional pharmaceutical agent are administered sequentially, the administration of each can be by the same or by different methods.

According to the methods of the invention, a compound of the present invention or a combination of a compound of the present invention and at least one additional pharmaceutical agent (referred to herein as a "combination") is preferably administered in the form of a pharmaceutical composition. Accordingly, a compound of the present invention or a combination can be administered to a patient separately or together in any conventional oral, rectal, transdermal, parenteral, (for example, intravenous, intramuscular, or subcutaneous) intracisternal, intravaginal, intraperitoneal, intravesical, local (for example, powder, ointment or drop), or buccal, or nasal, dosage form.

Compositions suitable for parenteral injection generally include pharmaceutically acceptable sterile aqueous or non-aqueous solutions, dispersions, suspensions, or emulsions, and sterile powders for reconstitution into sterile injectable solutions or dispersions. Examples of suitable aqueous and nonaqueous carriers, diluents, solvents, or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

These compositions may also contain adjuvants such as preserving, wetting, emulsifying, and dispersing agents. Prevention of microorganism contamination of the compositions can be accomplished with various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents capable of delaying absorption, for example, aluminum monostearate and gelatin.

Solid dosage forms for oral administration include capsules, tablets, powders, and granules. In such solid dosage forms, a compound of the present invention or a combination is admixed with at least one inert customary pharmaceutical excipient (or carrier) such as sodium citrate or dicalcium phosphate or (a) fillers or extenders (e.g., starches, lactose, sucrose, mannitol, silicic acid and the like); (b) binders (e.g., carboxymethylcellulose, alginates, gelatin, polyvinylpyrrolidone, sucrose, acacia and the like); (c) humectants (e.g., glycerol and the like); (d) disintegrating agents (e.g., agar-agar, calcium carbonate, potato or tapioca starch, alginic acid, certain complex silicates, sodium carbonate and the like); (e) solution retarders (e.g., paraffin and the like); (f) absorption accelerators (e.g., quaternary ammonium compounds and the like); (g) wetting agents (e.g., cetyl alcohol, glycerol monostearate and the like); (h) adsorbents (e.g., kaolin, bentonite and the like); and/or (i) lubricants (e.g., talc, calcium stearate, magnesium stearate, solid polyethylene glycols, sodium lauryl sulfate and the like). In the case of capsules and tablets, the dosage forms may also comprise buffering agents.

Solid compositions of a similar type may also be used as fillers in soft or hard filled gelatin capsules using such excipients as lactose or milk sugar, as well as high molecular weight polyethylene glycols, and the like.

Solid dosage forms such as tablets, dragees, capsules, and granules can be prepared with coatings and shells, such as enteric coatings and others well known in the art. They may also contain opacifying agents, and can also be of such composition that they release the compound of the present invention and/or the additional pharmaceutical agent in a delayed manner. Examples of embedding compositions that can be used are polymeric substances and waxes. The drug can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the compound of the present invention or the combination, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed oil, groundnut oil, corn germ oil, olive oil, castor oil, sesame seed oil and the like), glycerol, tetrahydrofurfuryl alcohol, polyethylene glycols and fatty acid esters of sorbitan, or mixtures of these substances, and the like.

Besides such inert diluents, the composition can also include adjuvants, such as wetting agents, emulsifying and suspending agents, sweetening, flavoring, and perfuming agents.

Suspensions, in addition to the compound of the present invention or the combination, may further comprise suspending agents, e.g., ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Compositions for rectal or vaginal administration preferably comprise suppositories, which can be prepared by mixing a compound of the present invention or a combination with suitable non-irritating excipients or carriers, such as cocoa butter, polyethylene glycol or a suppository wax which are solid at ordinary room temperature but liquid at body temperature and therefore melt in the rectum or vaginal cavity thereby releasing the active component(s).

Dosage forms for topical administration of the compounds of the present invention and combinations of the compounds of the present invention with anti-obesity agents may comprise ointments, powders, sprays and inhalants. The drugs are admixed under sterile condition with a pharmaceutically acceptable carrier, and any preservatives, buffers, or propellants that may be required. Ophthalmic formulations, eye ointments, powders, and solutions are also intended to be included within the scope of the present invention.

The following paragraphs describe exemplary formulations, dosages, etc. useful for non-human animals. The administration of the compounds of the present invention and combinations of the compounds of the present invention with anti-obesity agents can be effected orally or non-orally (e.g., by injection).

An amount of a compound of the present invention or combination of a compound of the present invention with an anti-obesity agent is administered such that an effective dose is received. Generally, a daily dose that is administered orally to an animal is between about 0.01 and about 1,000 mg/kg of body weight, preferably between about 0.01 and about 300 mg/kg of body weight.

Conveniently, a compound of the present invention (or combination) can be carried in the drinking water so that a therapeutic dosage of the compound is ingested with the daily water supply. The compound can be directly metered into drinking water, preferably in the form of a liquid, water-soluble concentrate (such as an aqueous solution of a water-soluble salt).

Conveniently, a compound of the present invention (or combination) can also be added directly to the feed, as such, or in the form of an animal feed supplement, also referred to as a premix or concentrate. A premix or concentrate of the compound in a carrier is more commonly employed for the inclusion of the agent in the feed. Suitable carriers are liquid or solid, as desired, such as water, various meals such as alfalfa meal, soybean meal, cottonseed oil meal, linseed oil meal, corncob meal and corn meal, molasses, urea, bone meal, and mineral mixes such as are commonly employed in poultry feeds. A particularly effective carrier is the respective animal feed itself; that is, a small portion of such feed. The carrier facilitates uniform distribution of the compound in the finished feed with which the premix is blended. Preferably, the compound is thoroughly blended into the premix and, subsequently, the feed. In this respect, the compound may be dispersed or dissolved in a suitable oily vehicle such as soybean oil, corn oil, cottonseed oil, and the like, or in a volatile organic solvent and then blended with the carrier. It will be appreciated that the proportions of compound in the concentrate are capable of wide variation since the amount of the compound in the finished feed may be adjusted by blending the appropriate proportion of premix with the feed to obtain a desired level of compound.

High potency concentrates may be blended by the feed manufacturer with proteinaceous carrier such as soybean oil meal and other meals, as described above, to produce concentrated supplements, which are suitable for direct feeding to animals. In such instances, the animals are permitted to consume the usual diet. Alternatively, such concentrated supplements may be added directly to the feed to produce a nutritionally balanced, finished feed containing a therapeutically effective level of a compound of the present invention. The mixtures are thoroughly blended by standard procedures, such as in a twin shell blender, to ensure homogeneity.

If the supplement is used as a top dressing for the feed, it likewise helps to ensure uniformity of distribution of the compound across the top of the dressed feed.

Drinking water and feed effective for increasing lean meat deposition and for improving lean meat to fat ratio are generally prepared by mixing a compound of the present invention with a sufficient amount of animal feed to provide from about $10^{-3}$ to about 500 ppm of the compound in the feed or water.

The preferred medicated swine, cattle, sheep and goat feed generally contain from about 1 to about 400 grams of a compound of the present invention (or combination) per ton of feed, the optimum amount for these animals usually being about 50 to about 300 grams per ton of feed.

The preferred poultry and domestic pet feeds usually contain about 1 to about 400 grams and preferably about 10 to about 400 grams of a compound of the present invention (or combination) per ton of feed.

For parenteral administration in animals, the compounds of the present invention (or combination) may be prepared in the form of a paste or a pellet and administered as an implant, usually under the skin of the head or ear of the animal in which increase in lean meat deposition and improvement in lean meat to fat ratio is sought.

In general, parenteral administration involves injection of a sufficient amount of a compound of the present invention (or combination) to provide the animal with about 0.01 to about 20 mg/kg/day of body weight of the drug. The preferred dosage for poultry, swine, cattle, sheep, goats and domestic pets is in the range of from about 0.05 to about 10 mg/kg/day of body weight of drug.

Paste formulations can be prepared by dispersing the drug in a pharmaceutically acceptable oil such as peanut oil, sesame oil, corn oil or the like.

Pellets containing an effective amount of a compound of the present invention, pharmaceutical composition, or combination can be prepared by admixing a compound of the present invention or combination with a diluent such as carbowax, carnuba wax, and the like, and a lubricant, such as magnesium or calcium stearate, can be added to improve the pelleting process.

It is, of course, recognized that more than one pellet may be administered to an animal to achieve the desired dose level which will provide the increase in lean meat deposition and improvement in lean meat to fat ratio desired. Moreover, implants may also be made periodically during the animal treatment period in order to maintain the proper drug level in the animal's body.

The present invention has several advantageous veterinary features. For the pet owner or veterinarian who wishes to increase leanness and/or trim unwanted fat from pet animals, the instant invention provides the means by which this may be accomplished. For poultry and swine breeders, utilization of the method of the present invention yields leaner animals that command higher sale prices from the meat industry.

Embodiments of the present invention are illustrated by the following Examples. It is to be understood, however, that the embodiments of the invention are not limited to the specific details of these Examples, as other variations thereof will be known, or apparent in light of the instant disclosure, to one of ordinary skill in the art.

EXAMPLES

Preparations of Key Intermediates

Preparation for Intermediate [4-(4-Methoxy-phenyl)-oxazol-2-yl]-acetic acid methyl ester (I-1a)

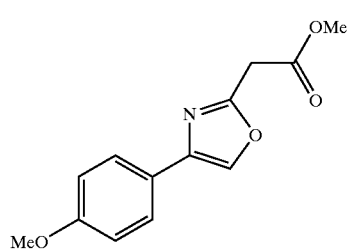

I-1a p-Methoxybromoacetophenone (3.0 g, 13 mmol) and methyl malonate monoamide (23 g, 196 mmol) were combined in a round-bottomed flask and heated to about 130° C. for 90 minutes. The reaction mixture was then allowed to cool to room temperature, and the resulting orange solid was partitioned between ethyl acetate and water, and extracted with ethyl acetate. The combined organic extracts were washed with brine, dried over magnesium sulfate, and concentrated in vacuo. The resulting crude solid was purified by column chromatography (5% ethyl acetate/hexanes to 10% ethyl acetate/hexanes) to afford 2.5 g (77% yield) of title compound (I-1a) as a white solid. LRMS ([M+H]$^+$): 248.3.

Preparation for Intermediate [4-Methoxy-phenyl)-oxazol-2-yl]-acetic acid (I-1b)

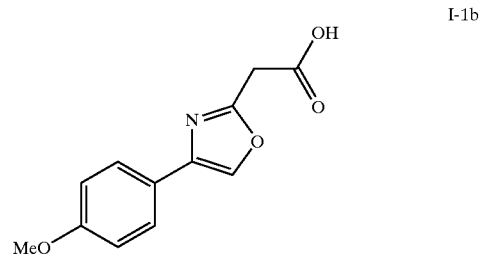

I-1b

To a round-bottomed flask containing [4-(4-methoxy-phenyl)-oxazol-2-yl]-acetic acid methyl ester I-1a (2.4 g, 9.7 mmol) was added 97 ml each of tetrahydrofuran, methanol, and 1 N NaOH, sequentially. The resulting solution was stirred at room temperature for about 3 hours, and was then concentrated to remove the volatiles in vacuo. The resulting mixture was partitioned between water and ethyl acetate, and the pH of the aqueous layer was adjusted to about 3 with concentrated HCl. The aqueous layer was then extracted with ethyl acetate, and the combined organic layers were washed with brine, dried over magnesium sulfate, filtered, and concentrated in vacuo. The crude material was recrystallized from ethyl acetate to afford the title product (I-1b) as a white solid (1.5 g, 66 % yield).

Preparation for 2-[4-(4-Methoxy-phenyl)-oxazol-2-yl]-1-pyrrolidin-1-yl-ethanone (I-1c)

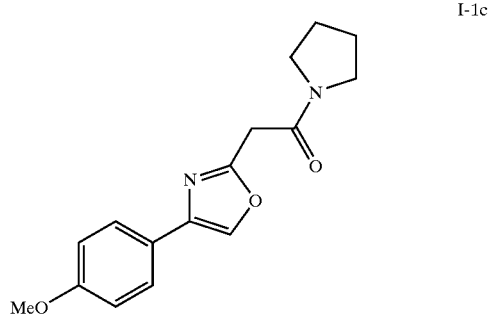

I-1c

In a round-bottomed flask, [4-(4-methoxy-phenyl)-oxazol-2-yl]-acetic acid I-1b (500 mg, 2.14 mmol) was combined with pyrrolidine (228 mg, 3.21 mmol), EDC (615 mg, 3.21 mmol), and hydroxybenzotriazole (433 mg, 3.21 mmol) in 21 ml of dichloromethane. The resulting mixture was stirred overnight, concentrated in vacuo to approximately one third of the reaction volume, and loaded directly onto a silica gel column for chromatography (50% EtOAc/hexanes). The product (I-1c) was obtained as a white solid (670 mg, 109% yield). LRMS ([M+H]$^+$): 287.2.

Preparation for Intermediate 2-[4-(Hydroxy-phenyl)-oxazol-2-yl]-1-pyrrolidin-1-yl-ethanone (I-1d)

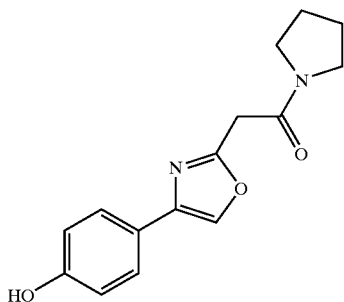

I-1d

2-[4-(4-Methoxy-phenyl)-oxazol-2-yl]-1-pyrrolidin-1-yl-ethanone I-1c (670 mg, 2.34 mmol) was combined with D,L-methionine (489 mg, 3.28 mmol) in methanesulfonic acid (10 ml) and the resulting mixture was heated to 60° C. for about 24 hours. The reaction was then cooled to room temperature, and then slowly added to stirring saturated aqueous sodium carbonate and ethyl acetate. The pH was adjusted to about 9, and the phases were separated. The aqueous phase was extracted with ethyl acetate, and the combined organic layers were washed with brine, dried over magnesium sulfate, filtered, and concentrated in vacuo. The resulting crystalline solids were suspended in a small volume of ethyl acetate, and collected by vacuum filtration to afford 480 mg (75% yield) of the desired title product (I-1d). LRMS ([M+H]+): 273.2.

Preparation for Intermediate (2-{4-[2-(2-Oxo-2-pyrrolidin-1-ylethyl)-oxazol-4-yl]-phenoxy}-ethyl)-carbamic acid benzyl ester (I-1e)

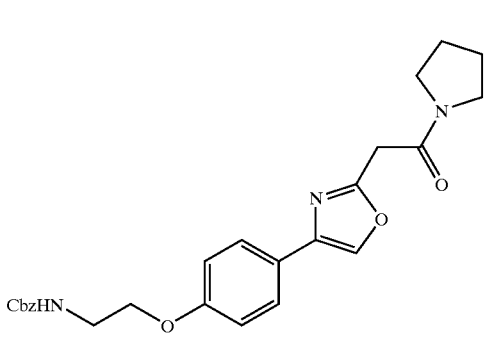

I-1e

In a round-bottomed flask, 2-[4-(4-hydroxy-phenyl)-oxazol-2-yl]-1-pyrrolidin-1-yl-ethanone I-1d (474 mg, 1.74 mmol) was dissolved in dimethylsulfoxide (6 ml), and potassium carbonate (powdered, 722 mg, 5.22 mmol) was added in a single portion. Methanesulfonic acid 2-benzyloxycarbonylamino-ethyl ester (952 mg, 3.48 mmol) was added to the mixture, and the resulting heterogeneous solution was heated to 70° C. for about 18 hours. The reaction was judged complete by thin-layer chromatography, and was then cooled to room temperature, and poured into 50 ml of water, and 50 ml of ethyl acetate. The phases were separated and the aqueous phase was extracted with ethyl acetate. The combined organic extracts were washed with brine, dried over magnesium sulfate, filtered, and concentrated in vacuo to afford a dark yellow oil. This crude material was purified by column chromatography (2% methanol/dichloromethane) to afford the desired title product I-1e (529 mg, 68% yield). LRMS ([M+H]+): 450.1.

Preparation for Intermediate 2-{4-[4-(2-Amino-ethoxy)-phenyl]-oxazol-2-yl}-1-pyrrolidin-1-yl-ethanone (I-1f)

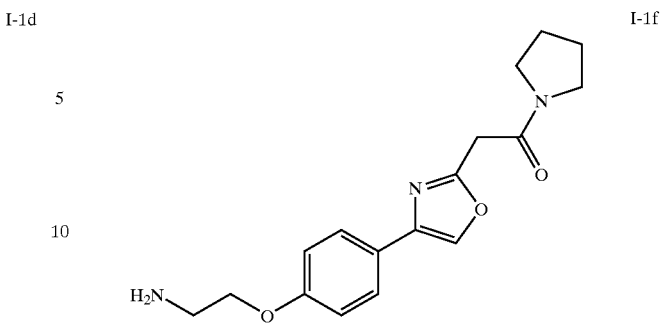

I-1f

In a hydrogenation bottle, (2-{4-[2-(2-oxo-2-pyrrolidin-1-yl-ethyl)-oxazol-4-yl]-phenoxy}-ethyl)-carbamic acid benzyl ester I-1e (529 mg, 1.18 mmol) was dissolved in methanol (30 ml), and 10% Pd/C (30 wt %, 160 mg) was added in one portion. The mixture was hydrogenated under 45 psi of hydrogen for about 2 hours until the reaction was judged complete by thin-layer chromatography. The mixture was then filtered through a pad of diatomaceous earth, and rinsed with methanol to remove the catalyst. The filtrate was then concentrated in vacuo to afford the desired product I-1f (370 mg, 100% yield) as a white solid. LRMS ([M+H]+): 316.2.

Preparation for Intermediate Benzyl-[2-(4-acetyl-phenoxy)-ethyl]-carbamate (I-2a)

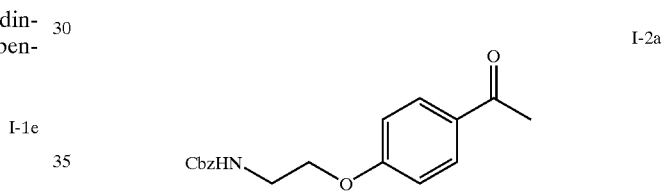

I-2a

In a round-bottomed flask equipped with a mechanical stirrer, 4-hydroxyacetophenone I-2a (5.00 g, 36.7 mmol) was dissolved in toluene (122 ml), and triphenylphosphine (14.4 g, 55.1 mmol) and benzyl N-(2-hydroxyethyl) carbamate (10.8 g, 55.1 mmol) were then added. The reaction mixture was cooled to about 0° C., and 1,1'-(azodicarbonyl)dipiperidine (13.9 g, 55.1 mmol) was added in one portion. The mixture was allowed to warm to room temperature, and after stirring for about 10 minutes, an additional 122 ml of toluene and 122 m of tetrahydrofuran were added to the thick orange solution. The mixture was stirred for about 24 hours, and then the solids were filtered off. The filtrate was concentrated in vacuo and the resulting solid was purified by column chromatography (hexanes to 2:1 hexanes/ethyl acetate) to afford 9.68 g (84% yield) of the desired product (I-2a) as a white solid. LRMS ([M-H]−): 312.2.

Preparation for Intermediate Benzyl-[2-(4-bromoacetylphenoxy)-ethyl]-carbamate (I-2b)

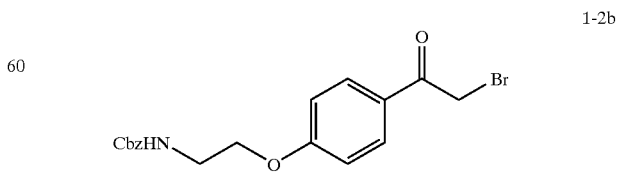

1-2b

Benzyl [2-(4-acetyl-phenoxy)-ethyl]-carbamate I-2a (10.2 g, 32.5 mmol) was dissolved in dichloromethane (100 ml) and methanol (50 ml), and tetrabutylammonium tribromide (15.7 g, 32.5 mmol) was added in one portion. The reaction mixture was stirred for about 16 hours, and was then quenched with water. The aqueous phase was extracted with ethyl acetate, and then washed with saturated aqueous sodium bicarbonate and saturated aqueous sodium bisulfite. The combined organic extracts were dried over magnesium sulfate, filtered, and concentrated in vacuo, and the resulting crude material was purified by column chromatography (hexanes to 2:1 hexanes/ethyl acetate) to afford a colorless oil which solidified on standing I-2b (11.5 g, 90% yield).

Preparation for Intermediate {4-[4-(2-Benzyloxycarbonylamino-ethoxy)-phenyl]-oxazol-2-yl}-acetic acid methyl ester (I-2c)

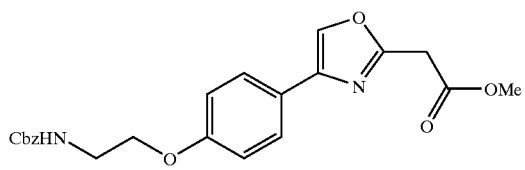

Methoxy malonamide (10.6 g, 90.6 mmol) and benzyl [2-(4-bromoacetyl-phenoxy)-ethyl]-carbamate I-2b (2.37 g, 6.04 mmol) were combined in a round-bottomed flask and heated to 130° C. for about 90 minutes. The reaction mixture was then allowed to cool to room temperature, and the resulting orange solid was partitioned between ethyl acetate and water and extracted with ethyl acetate. The combined organic extracts were washed with brine, dried over magnesium sulfate, filtered, and concentrated in vacuo. The resulting crude solid was purified by column chromatography (30% hexanes/ethyl acetate to 50% hexanes/ethyl acetate) to afford 1.29 g (50% yield) of the title product as a white solid (I-2c).

Preparation for Intermediate {4-[4-(2-Benzyoxycarbonylamino-ethoxy)-phenyl]-oxazol-2-yl}-acetic acid (I-2d)

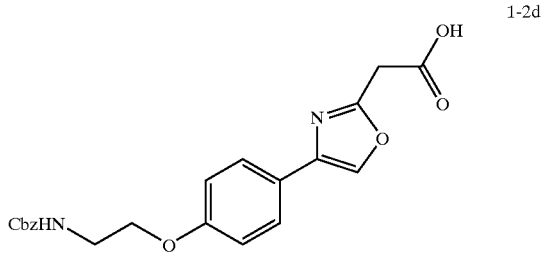

To a round-bottomed flask containing {4-[4-(2-benzyloxycarbonylamino-ethoxy)-phenyl]-oxazol-2-yl}-acetic acid methyl ester I-2c (1.29 g, 3.00 mmol) was added 10 ml each of tetrahydrofuran, methanol, and 1 N NaOH, sequentially. The resulting solution was stirred at room temperature for about 5 minutes, and then quenched with 1 N HCl, and extracted with ethyl acetate. The combined organic layers were washed with brine, dried over magnesium sulfate, filtered, and concentrated in vacuo. The resulting yellow solid (I-2d) was determined to be pure by $^1$H NMR and was used directly in the next reaction (1.20 g, 100% yield).

Preparation for Intermediate [2-(4-{2-[(Diisopropylcarbamoyl)-methyl]-oxazol-4-yl}-phenoxy)-ethyl]-carbamic acid benzyl ester (I-2e)

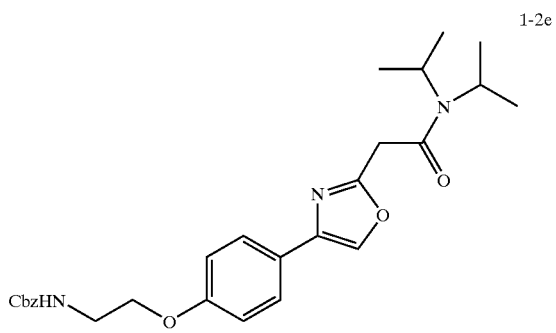

In a round-bottomed flask, {4-[4-(2-benzyloxycarbonylamino-ethoxy)-phenyl]-oxazol-2-yl}-acetic acid I-2d (350 mg, 0.883 mmol) was combined with diisopropylamine (160 µl, 1.15 mmol), benzotriazol-1-yl-oxytripyrrolidinophosphonium hexafluorophosphate (PyBop) (598 mg, 1.15 mmol), and diisopropylethyl amine (230 µl, 1.32 mmol) in 1,2-dichloroethane (4.4 ml). The resulting mixture was stirred overnight, concentrated in vacuo to approximately one third of the reaction volume, and loaded directly onto a silica gel column for chromatography (50% hexanes/ethyl acetate). The product was obtained as a white solid I-2e (219 mg, 52% yield). LRMS ([M+H]$^+$): 480.2.

Preparation for Intermediate 2-[4-(4-Methoxy-phenyl)-oxazol-2-yl]-hexanoic acid N,N-dimethylamide (I-3a)

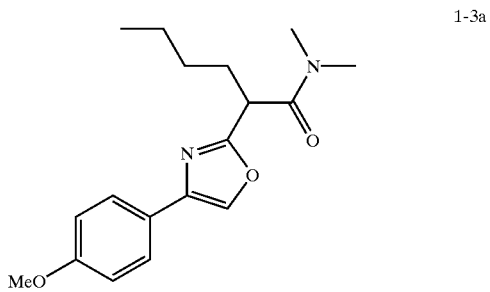

To a stirred solution of 300 mg (1.15 mmol) of 2-[4-(4-methoxy-phenyl)-oxazol-2-yl]-N,N-dimethyl-acetamide in 4 ml of tetrahydrofuran under nitrogen at 0° C. was added 1.15 ml of a 1.0 M tetrahydrofuran solution of lithium bis(trimethylsilyl)amide, and the resulting solution was stirred for 30 minutes. To this solution was added 0.13 µl (1.15 mmol) of 1-iodobutane, and the reaction mixture was allowed to warm to room temperature and stir overnight. After cooling to 0° C., water was added and the mixture was warmed to room temperature. The mixture was extracted with ethyl acetate and the combined organic layers were dried over sodium sulfate and concentrated in vacuo. The resulting material was purified by column chromatography using 2% acetone/dichloromethane to 5% acetone/dichloromethane as the gradient eluant to afford the desired title product I-3a (212 mg, 58% yield) as a solid. LRMS ([M+H]$^+$): 317.5.

Preparation for Intermediate {2-[4-(3-Dimethylamino-acryloyl)-phenoxy]-ethyl}-carbamic acid benzyl ester (I-4a)

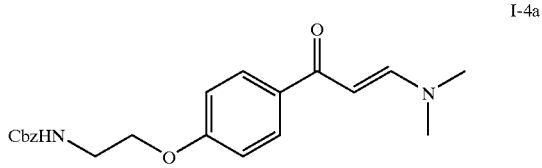

Benzyl [2-(4-acetyl-phenoxy)-ethyl]-carbamate (28.3 g, 90.3 mmol) and N,N-dimethylformamide diethyl acetal (62 ml, 361 mmol) were combined in a round-bottomed flask and heated to 70° C. for about 28 hours. The reaction was then cooled to room temperature, allowed to stand overnight, and then 25 ml of hexanes was added to the heterogeneous reaction mixture. The resulting slurry was filtered, and the solids were dried under vacuum to afford 30.11 g (81.7 mmol, 90% yield) of a mustard-yellow powder (I-4a). LRMS ([M+H]$^+$): 369.3.

Preparation for Intermediate {2-[4-(1H-Pyrazol-3-yl)-phenoxy]-ethyl}-carbamic acid benzyl ester (I-4b)

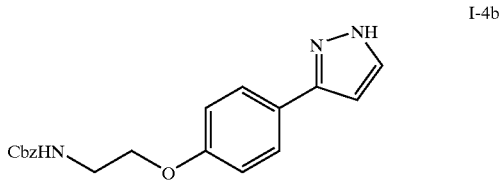

In a round-bottomed flask, {2-[4-(3-dimethylamino-acryloyl)-phenoxy]-ethyl}-carbamic acid benzyl ester I-4a (12.85 g, 34.87 mmol) was suspended in ethanol (70 ml), and hydrazine hydrate (3.38 ml, 69.76 mmol) was added dropwise via syringe. The reaction flask was fitted with a reflux condenser, and then heated to 80° C. for about 18 hours. The reaction was then allowed to cool to room temperature, and the resulting solids were suspended in a minimum amount of ethanol, and filtered under vacuum. The solids were dried in vacuo to yield a colorless solid I-4b (6.55 g), and the filtrate was concentrated and re-suspended in ethanol to afford a second crop of solids I-4b (2.27 g, for a combined yield of 75%). LRMS ([M+H]$^+$): 338.3.

Preparation for Intermediate {3-[4-(2-Benzyloxycarbonylamino-ethoxy)-phenyl]-pyrazol-1-yl}-acetic acid Ethyl Ester (I-4c)

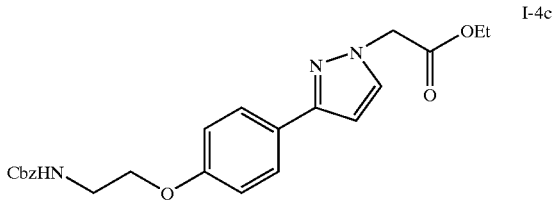

A 500 ml round-bottomed flask was charged with {2-[4-(1H-pyrazol-3-yl)-phenoxy]-ethyl}-carbamic acid benzyl ester I-4b (8.39 g, 24.87 mmol) and ethanol (80 ml). Sodium ethoxide (27.9 ml of a 21 wt % solution in ethanol, 74.6 mmol) was added dropwise via addition funnel over a period of about 5 minutes, followed by bromoacetic acid ethyl ester (5.51 ml, 49.73 mmol). The resulting mixture was stirred for about 15 hours, and was then quenched to neutral pH by the addition of concentrated HCl. The volatiles were removed in vacuo, and 500 ml of diethyl ether were added to form a slurry. The solids were removed by vacuum filtration to yield 10.6 g of brown-colored solid which was discarded. The ether filtrate was then concentrated to an oil (8.1 g) which was purified by column chromatography (40% hexanes/ethyl acetate) to afford 3.06 g of the desired title product I-4c (7.22 mmol, 29% yield). LRMS ([M+H]$^+$): 424.3.

Preparation for Intermediate {3-[4-(2-Benzyloxycarbonylamino-ethoxy)-phenyl]-pyrazol-1-yl}-acetic acid (I-4d)

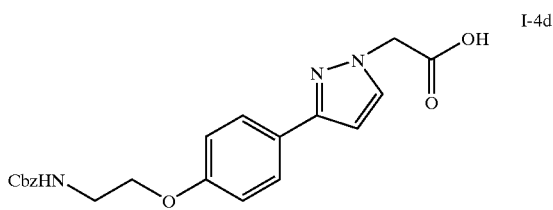

In a round-bottomed flask, {3-[4-(2-benzyloxycarbonylamino-ethoxy)-phenyl]-pyrazol-1-yl}-acetic acid ethyl ester I-4c (1.19 g, 2.81 mmol) was dissolved in tetrahydrofuran (9.0 ml). Methanol (9 ml) and 1 N LiOH (9 ml) were added sequentially, and the mixture was stirred for about 10 minutes. The reaction was brought to pH 3 with 3 N HCl, and was then diluted with water and dichloromethane. The aqueous phase was extracted with dichloromethane and the combined organics were dried over sodium sulfate, filtered, and concentrated in vacuo. The resulting crude material (1.17 g) was triturated with ether and decanted to afford 936 mg (84% yield) of the desired product (I-4d). LRMS ([M+H]$^+$): 396.3.

Preparation for Intermediate {2-[4-(1-Cyclopentylcarbamoylmethyl-1H-pyrazol-3-yl)-phenoxy]-ethyl}-carbamic acid benzyl ester (I-4e)

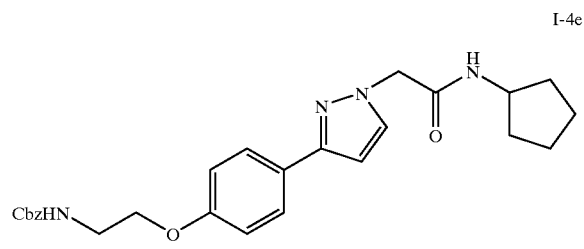

In a round-bottomed flask, {3-[4-(2-benzyloxycarbonylamino-ethoxy)-phenyl]-pyrazol-1-yl}-acetic acid I-4d (244 mg, 0.617 mmol) and diisopropylethyl amine (322 μl, 1.85 mmol) were dissolved in dichloromethane (6 ml). EDC.HCl (178 mg, 0.926 mmol) was added to the solution, followed by hydroxybenzotriazole hydrate (125 mg, 0.926 mmol) and cyclopentylamine (122 μl, 1.23 mmol). The reaction mixture was stirred for about 48 hours, and was then diluted with ethyl acetate and saturated aqueous sodium bicarbonate. The aqueous phase was extracted with ethyl acetate, and the combined organics were dried over magnesium sulfate, filtered, and concentrated in vacuo. The crude material was purified by column chromatography (1.5% methanol/dichloromethane) to afford 290 mg (102% yield) of the desired product (I-4e). LRMS ([M+H]$^+$): 463.4.

Preparation for Intermediate 2-{3-[4-(2-Amino-ethoxy)-phenyl]-pyrazol-1-yl}-N-cyclopentyl-acetamide (I-4f)

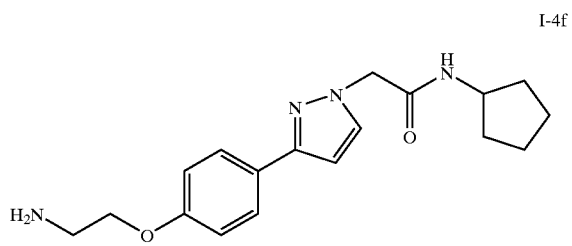

In a nitrogen-purged round-bottomed flask, {2-[4-(1-cyclopentylcarbamoylmethyl-1H-pyrazol-3-yl)-phenoxy]-ethyl}-carbamic acid benzyl ester I-4e (285 mg, 0.616 mmol) was dissolved in methanol (6.1 ml). To this solution, 10% Pd/C (100 mg, 30 wt %) and formic acid (2.46 ml, 95 mmol) were added, and the reaction was stirred overnight. The reaction mixture was then filtered through a pad of diatomaceous earth, and the filtrate was concentrated. The resulting material was then dissolved in water, the pH was adjusted to 12 with 5 N NaOH, and the aqueous phase was extracted with ethyl acetate. The combined organic layers were dried over sodium sulfate, filtered, and concentrated in vacuo. The resulting product I-4f (173 mg, 85% yield) was carried directly into the next reaction. LRMS ([M+H]$^+$): 329.4.

Preparation for Intermediate 3-Dimethylamino-1-(4-methoxy-phenyl)-prop-2-en-1-one (I-5a)

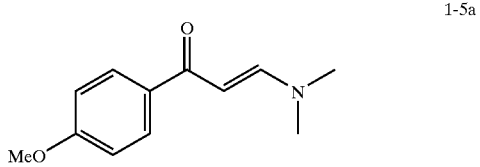

p-Methoxyacetophenone (4.50 g, 30.0 mmol) and N,N-dimethylformamide diethyl acetal (25.7 ml, 150 mmol) were combined in a round-bottomed flask and heated to 130° C. for about 18 hours. The reaction was then cooled to room temperature and concentrated in vacuo. Diethyl ether (30 ml) was added to the reaction mixture and the resulting solids (2.59 g) were collected by vacuum filtration. The filtrate was then concentrated to dryness and re-suspended in diethyl ether to yield a second crop of solids which was collected by filtration (1.38 g). The combined solids I-5a (3.97 g, 65% yield) were carried directly into the next step.

Preparation for Intermediate [5-(4-Methoxy-phenyl)-pyrazol-1-yl]-acetic acid ethyl ester (I-5b)

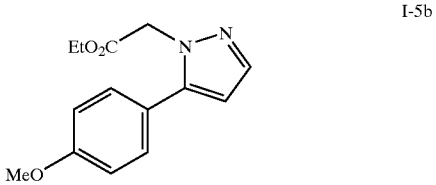

Ethyl hydrazinoacetate hydrochloride (1.91 g, 12.3 mmol) and 3-dimethylamino-1-(4-methoxy-phenyl)-prop-2-en-1-one I-5a (2.53 g, 12.3 mmol) were dissolved in ethanol (40 ml). Potassium carbonate (1.70 g, 12.3 mmol) was added to this solution, and the resulting mixture was heated to 80 ° C. for about 16 hours. The reaction was then cooled to room temperature and concentrated in vacuo. The crude paste was suspended in water (50 ml), and the pH was adjusted to 9. The aqueous mixture was extracted with ethyl acetate, and the combined organic extracts were washed with brine, dried over magnesium sulfate, filtered, and concentrated in vacuo. The material was then purified by column chromatography (hexanes to 35% ethyl acetate/hexanes) to afford 2.61 g (81% yield) of the desired product (I-5b). LRMS ([M+H]$^+$): 261.3.

Preparation for Intermediate [5-(4-Methoxy-phenyl)-pyrazol-1-yl]-acetic acid (I-5c)

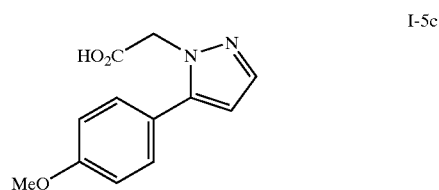

[5-(4-Methoxy-phenyl)-pyrazol-1-yl]-acetic acid ethyl ester I-5b (2.50 g, 9.60 mmol) was dissolved in tetrahydrofuran (30 ml) and methanol (30 ml). To this mixture, LiOH (902 mg, 38.4 mmol), and water (30 ml) were added. The mixture was stirred for about 15 minutes, and was then partitioned between ethyl acetate and water. The pH was adjusted to 3, and the aqueous phase was extracted with ethyl acetate. The combined organic extracts were dried over sodium sulfate, filtered, and concentrated in vacuo to afford the title compound (I-5c) as a colorless solid (2.08 g, 93% yield). LRMS ([M+H]$^+$): 233.3.

Preparation for Intermediate 2-[5-(4-Methoxy-phenyl)-pyrazol-1-yl]-1-pyrrolidin-1-yl-ethanone (I-5d)

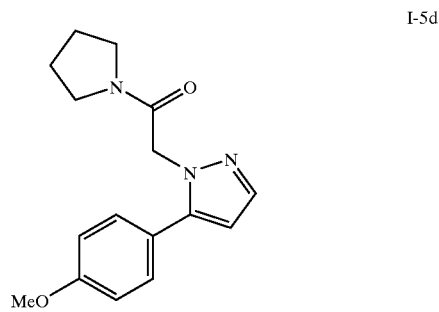

In a round-bottomed flask, [5-(4-methoxy-phenyl)-pyrazol-1-yl]-acetic acid I-5c was dissolved in dichloromethane (9.5 ml). To this solution, EDC.HCl (817 mg, 4.26 mmol), diisopropylethyl amine (1.48 ml, 8.52 mmol), hydroxybenzotriazole hydrate (576 mg, 4.26 mmol), and pyrrolidine (475 μL, 5.68 mmol) were added sequentially. The reaction was allowed to stir for about 2 days, and was then diluted with dichloromethane and quenched with saturated aqueous sodium bicarbonate. The aqueous phase was extracted with dichloromethane, and the combined organics were dried over magnesium sulfate, filtered, and concentrated in vacuo. The resulting crude material was purified by column chromatography (3% methanol/dichloromethane) to afford 475 mg (59% yield) of the desired product (I-5d). LRMS ([M+H]$^+$): 286.3.

Preparation for Intermediate 2-[5-(4-Hydroxy-phenyl)-pyrazol-1-yl]-1-pyrrolidin-1-yl-ethanone (I-5e)

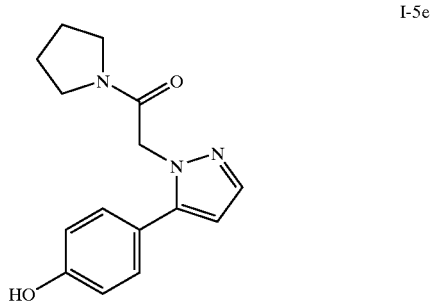

I-5e

In a round-bottomed flask, 2-[5-(4-methoxy-phenyl)-pyrazol-1-yl]-1-pyrrolidin-1-yl-ethanone I-5d (440 mg, 1.54 mmol) was combined with D,L-methionine (345 mg, 2.31 mmol) in methanesulfonic acid (6.2 ml) and the resulting mixture was heated to 70° C. for about 22 hours. The reaction was then cooled to room temperature, and then slowly added to stirring saturated aqueous sodium carbonate and ethyl acetate. The pH was adjusted to 9, and the phases were separated. The aqueous phase was extracted with ethyl acetate, and the combined organic layers were washed with brine, dried over magnesium sulfate, filtered, and concentrated in vacuo. The resulting crude material was purified by column chromatography (dichloromethane to 3% methanol/dichloromethane) to afford 280 mg (1.03 mmol, 67% yield) of the desired product (I-5e) as a colorless solid. LRMS ([M+H]$^+$): 272.2.

Preparation for Intermediate (2-{4-[2-(2-Oxo-2-pyrrolidin-1-yl-ethyl)-2H-pyrazol-3-yl]-phenoxy)-ethyl-carbamic Acid Benzyl Ester (I-5f)

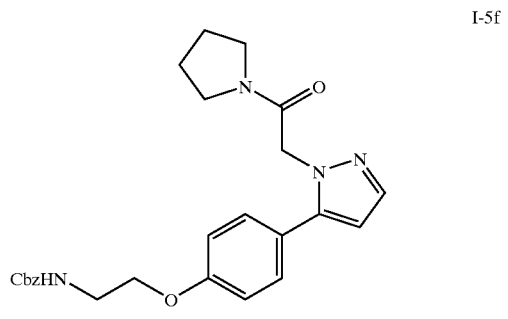

I-5f

In a round-bottomed flask, 2-[5-(4-hydroxy-phenyl)-pyrazol-1-yl]-1-pyrrolidin-1-yl-ethanone I-5e (273 mg, 1.00 mmol) was dissolved in dimethylsulfoxide (2 ml), and potassium carbonate (powdered, 415 mg, 3.00 mmol) was added in one portion. Methanesulfonic acid 2-benzyloxycarbonylamino-ethyl ester (547 mg, 2.00 mmol) was then added to the mixture, and the resulting heterogeneous solution was heated to 70° C. for about 18 hours. The reaction was judged complete by thin-layer chromatography, and was then cooled to room temperature, and poured into 20 ml of water. The aqueous phase was extracted 3× with dichloromethane, and the combined organic extracts were washed with brine, dried over magnesium sulfate, filtered, and concentrated in vacuo to afford a dark yellow oil. This crude material was purified by column chromatography (2% methanol/dichloromethane) to afford the desired product I-5f (390 mg, 87% yield). LRMS ([M+H]$^+$): 449.4.

Preparation for Intermediate 2-{5-[4-(2-Amino-ethoxy)-phenyl]-pyrazol-1-yl}-1-pyrrolidin-1-yl-ethanone (I-5g)

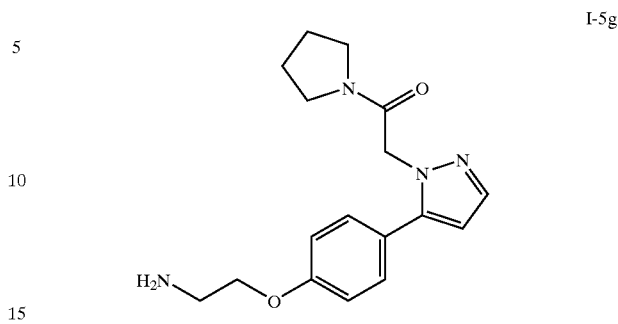

I-5g

In a nitrogen-purged, round-bottomed flask, (2-{4-[2-(2-oxo-2-pyrrolidin-1-yl-ethyl)-2H-pyrazol-3-yl]-phenoxy}-ethyl)-carbamic acid benzyl ester I-5f (390 mg, 0.870 mmol) was dissolved in methanol (8.70 ml). To this solution, 10% Pd/C (150 mg, 30 wt %), and formic acid (3.48 ml, 133 mmol) were added, and the reaction was stirred overnight. The reaction mixture was then filtered through a pad of diatomaceous earth, and the filtrate was concentrated. The resulting material was then dissolved in water and the pH was adjusted to 12 with 5 N NaOH, and the aqueous phase was extracted with ethyl acetate. The combined organics were dried over sodium sulfate, filtered, and concentrated in vacuo. The resulting product I-5g (225 mg, 72% yield) was carried directly into the next reaction. LRMS ([M+H]$^+$): 315.4.

Example 1 illustrates the preparation of compounds of the present invention where Ar is a pyridyl group.

Example 1

Preparation for 2-[4-(4-{2-[2-(6-Chloro-pyridin-3-yl)-2(R)-hydroxy-ethylamino]-ethoxy}-phenyl)-oxazol-2-yl]-1-pyrrolidin-1-yl-ethanone (1-1A)

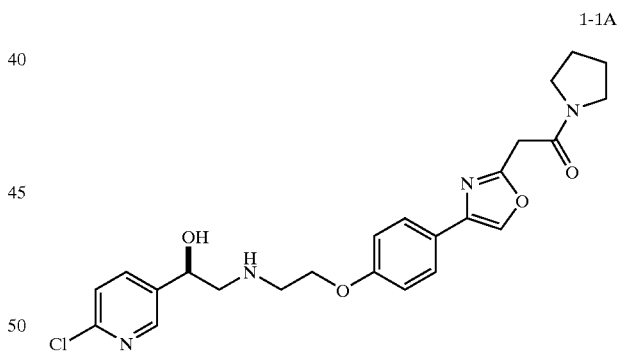

1-1A

In a round-bottomed flask, (R)-2-chloro-5-oxiranyl-pyridine (123 mg, 0.79 mmol) and 2-{4-[4-(2-amino-ethoxy)-phenyl]-oxazol-2-yl}-1-pyrrolidin-1-yl-ethanone I-1f (370 mg, 1.18 mmol) were dissolved in 20 ml of ethanol, and the mixture was heated to 80° C. for about 16 hours. The solution was then concentrated in vacuo to an oil, and the crude material was purified by column chromatography (dichloromethane to 10% methanol/dichloromethane) to afford 200 mg (54% yield) of the title product as a white solid. LRMS ([M+H]$^+$): 471.3.

$^1$H NMR: (400 MHz, CD$_3$OD): δ1.91 (m, 2H), 1.99 (m, 2H), 2.85 (m, 2H), 3.03 (m, 2H), 3.45 (m, 2H), 3.61 (m, 2H), 3.95 (s, 2H), 4.10 (m, 2H), 4.84 (m, 1H) 6.97 (d, 2H, J=8.8 Hz), 7.42 (d, 1H, J=8.0 Hz), 7.64 (d, 2H, J=8.4 Hz), (dd, 1H, J=2.8, 8.4 Hz), 8.10 (s, 1H), 8.37 (d, 1H, J=2.8 Hz).

Preparation for 2-(4-{4-[2-(2(R)-Hydroxy-2-pyridin-3-yl-ethylamino)-ethoxy]-phenyl}-oxazol-2-yl)-1-pyrrolidin-1-yl-ethanone (1-1B)

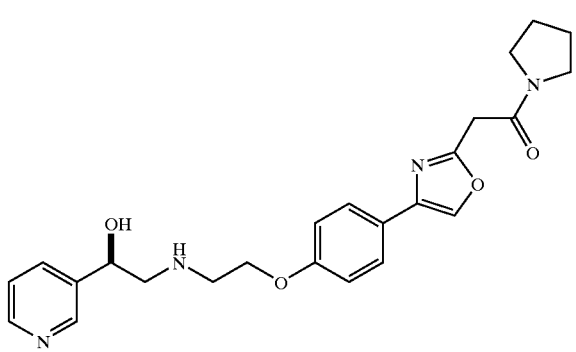

In a nitrogen-purged, round-bottomed flask, (R)-2-[4-(4-{2-[2-(6-chloro-pyridin-3-yl)-2-hydroxy-ethylamino]-ethoxy}-phenyl)-oxazol-2-yl]-1-pyrrolidin-1-yl-ethanone 1-1A (200 mg, 0.42 mmol) was dissolved in methanol (15 ml). 10% Pd/C (160 mg, 80 wt %), and ammonium formate (321 mg, 5.1 mmol) were then added sequentially. The reaction mixture was stirred overnight, and was then filtered through a pad of diatomaceous earth, and the filter cake rinsed with ethyl acetate. The filtrate was concentrated to a white solid, which was taken up in ethyl acetate and saturated aqueous sodium carbonate, and extracted. The organic extracts were washed with brine, dried over magnesium sulfate, filtered, and concentrated in vacuo to afford a crude solid. This material was suspended in diethylether and isolated by vacuum filtration to afford a crystalline solid 1-1B (110 mg, 59% yield). This material was then converted to the corresponding hydrochloride salt. Analytical data for the HCl salt: LRMS ([M+H]$^+$): 437.4. $^1$H NMR: (400 MHz, CD$_3$OD): δ1.91 (m, 2H), 2.02 (m, 2H), 3.37–3.29 (m, 2H), 3.45 (m, 2H), 3.54–3.63 (m, 5H), 3.97 (s, 2H), 4.37 (t, 2H, J=4.8 Hz), 5.38 (dd, 1H, J=3.2,10.4 Hz), 7.07 (dd, 2H, J=2.8, 9.6 Hz), 7.69 (dd, 2H, J=1.8, 6.4 Hz), 8.14 (m, 2H), 8.75 (m, 1H), 8.86 (d, 1H, J=6.0 Hz), 8.99 (m, 1H).

Preparation for 2-[4-(4-{2-[2-(R)-Hydroxy-2-(6-methyl-pyridin-3-yl)-ethylamino]-ethoxy}-phenyl)-oxazol-2-yl]-N,N-dimethyl-acetamide (1-1C)

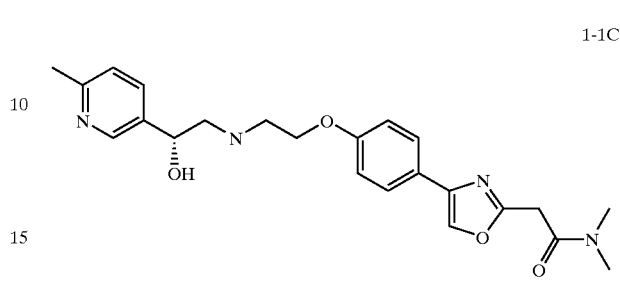

In a round-bottomed flask, (R)-2-methyl-5-oxiranyl-pyridine (4.4 g, 0.015 mol) and 2-{4-[4-(2-amino-ethoxy)-phenyl]-oxazol-2-yl}-N,N-dimethyl-acetamide (2.3 g, 0.017 mol) were dissolved in 16 ml of ethanol, and the mixture was heated to 60° C. for about 16 hours. A precipitate began forming after ca. 1 hour. The reaction mixture was then cooled to room temperature and diluted with ethyl acetate. The resulting mixture was stirred for 1 hour, and the solids were then removed by filtration and washed with ethyl acetate. These solids were then resuspended in ethyl acetate and heated to 70° C. to give a pale yellow solution. This solution was then cooled slowly and the resulting solids were isolated to afford 1.9 g (29%) of the title product as a pale pink solid. LRMS ([M+H]$^+$): 425.0. $^1$H NMR: (400 MHz, CD$_3$OD): δ8.42 (d, J=2.49, 1H), 8.12 (s, 1H), 7.76 (dd, 1H), 7.67 (dt, 2H), 7.29 (d, J=8.3, 1H), 6.99 (dt, 2H), 4.87 (t, J=6.23, 1H), 4.16 (m, 2H), 4.03(s, 2H), 3.16 (s, 3H), 3.12(m, 2H), 2.98 (s, 3H), 2.93(d, J=6.64, 2H), 2.52 (s, 3H)

Table I below lists compounds that were prepared using the general procedures described above for the preparation of compounds 1-1A, 1-1B and 1-1C with the appropriate starting materials.

TABLE 1

| Example No. | Compound Name | LRMS [M + H]$^+$ |
| --- | --- | --- |
| 1-ID | 2-(4-{4-[2-(2(R)-Hydroxy-2-pyridin-3-yl-ethylamino)-ethoxy]-phenyl}-oxazol-2-yl)-1-morpholin-4-yl-ethanone hydrochloride salt | 471.3 |
| 1-1E | 2-(4-{4-[2-(2(R)-Hydroxy-2-pyridin-3-yl-ethylamino)-ethoxyl-phenyl}-oxazol-2-yl)-N,N-dimethyl-acetamide hydrochloride salt | 437.4 |
| 1-1F | N-Cyclopentyl-2-(4-{4-[2-(2(R)-hydroxy-2-pyridin-3-yl-ethylamino)-ethoxy]-phenyl}-oxazol-2-yl)-acetamide hydrochloride salt | 425.0 |
| 1-1G | 2-(4-{4-[2-(2(R)-Hydroxy-2-pyridin-3-yl-ethylamino)-ethoxy]-phenyl}-oxazol-2-yl)-1-piperidin-1-yl-ethanone hydrochloride salt | 453.3 |
| 1-1H | N,N-Diethyl-2-(4-{4-[2-(2(R)-hydroxy-2-pyridin-3-yl-ethylamino)-ethoxy]-phenyl}-oxazol-2-yl)-acetamide hydrochloride salt | 411.2 |
| 1-1I | 2-[4-(4-{2-[2-(6-Chloro-pyridin-3-yl)-2(R)-hydroxy-ethylamino]-ethoxy}-phenyl)-oxazol-2-yl]-1-morpholin-4-yl-ethanone | 451.4 |
| 1-1J | 2-[4-(4-{2-[2-(6-Chloro-pyridin-3-yl)-2(R)-hydroxy-ethylamino]-ethoxy}-phenyl)-oxazol-2-yl]-N,N-diethyl-acetamide | 451.4 |
| 1-1K | 2-[4-(4-{2-[2-(6-Chloro-pyridin-3-yl)-2(R)-hydroxy-ethylamino]-ethoxy}-phenyl)-oxazol-2-yl]-1-piperidin-1-yl-ethanone | 439.4 |

TABLE 1-continued

| Example No. | Compound Name | LRMS [M + H]+ |
|---|---|---|
| 1-1L | 2-[4-(4-{2-[2-(6-Chloro-pyridin-3-yl )-2(R)-hydroxy-ethylamino]-ethoxy}-phenyl)-oxazol-2-yl]-N-cyclopentyl-acetamide | 487.3 |
| 1-1M | 2-(4-{4-[2-(2(R)-Hydroxy-2-pyridin-3-yl-ethylamino)-ethoxy]-phenyl}-oxazol-2-yl)-N-methyl-acetamide hydrochloride salt | 473.4 |
| 1-1N | N-Ethyl-2-(4-{4-[2-(2( R)-hydroxy-2-pyridin-3-yl-ethylamino)-ethoxy]-phenyl}-oxazol-2-yl)-N-methyl-acetamide hydrochloride salt | 485.4 |
| 1-1O | 2-[4-(4-{2-[2-(6-Chloro-pyridin-3-yl )-2(R)-hydroxy-ethylamino]-ethoxy}-phenyl)-oxazol-2-yl]-N-methyl-acetamide | 485.3 |
| 1-1P | 2-114-(4-{2-[2-(6-Chloro-pyridin-3-yl )-2(R)-hydroxy ethylamino]-ethoxy}-phenyl)-oxazol-2-yl]-N-ethyl-N-methyl-acetamide | 397.4 |
| 1-1Q | 1-Azetidin-1-yl-2-(4-{4-[2-(2( R)-hydroxy-2-pyridin-3-yl-ethylamino)-ethoxy]-phenyl}-oxazol-2-yl)-ethanone hydrochloride salt | 425.4 |
| 1-1R | N-Ethyl-2-(4-{4-[2-(2(R)-hydroxy-2-pyridin-3-yl-ethylamino)-ethoxy]-phenyl}-oxazol-2-yl)-N-isopropyl-acetamide hydrochloride salt | 431.4 |
| 1-1S | 2-(4-{4-[2-(2(R)-Hydroxy-2-pyridin-3-yl-ethylamino)-ethoxy]-phenyl}-oxazol-2-yl)-N-isopropyl-N-methyl-acetamide hydrochloride salt | 459.2 |
| 1-1T | 2-[4-(4-{2-[2-(6-Chloro-pyridin-3-yl)-2(R)-hydroxy-ethylamino]-ethoxy}-phenyl)-oxazol-2-yl]-N-ethyl-N-(2,2,2-trifluoro-ethyl)-acetamide | 423.4 |
| 1-1U | 2-[4-(4-{2-[2-(6-Chloro-pyridin-3-yl)-2(R)-hydroxy-ethylamino]-ethoxy}-phenyl)-oxazol-2-y]-N,N-diisopropyl-acetamide | 453.5 |
| 1-1V | N-Ethyl-2-(4-{4-[2-(2(R)-hydroxy-2-pyridin-3-yl-ethylamino)-ethoxy]-phenyl}-oxazol-2-yl)-N-(2,2,2-trifluoro-ethyl)-acetamide hydrochloride salt | 439.4 |
| 1-1W | 2-(4-{4-[2-(2(R)-Hydroxy-2-pyridin-3-yl-ethylamino)-ethoxy]-phenyl}-oxazol-2-yl)-N,N-diisopropyl-acetamide hydrochloride salt | 527.4 |
| 1-1X | 2-(4-{4-[2-(2(R)-Hydroxy-2-pyridin-3-yl-ethylamino)-ethoxy]-phenyl}-oxazol-2-yl)-N-methyl-N-(2,2,2-trifluoro-ethyl)-acetamide hydrochloride salt | 501.5 |
| 1-1Y | 2-[4-(4-{2-[2-(6-Chloro-pyridin-3-yl)-2( R)-hydroxy-ethylamino]-ethoxy}-phenyl)-oxazol-2-yl]-N,N-diisopropyl-propionamide | 493.2 |
| 1-1Z | 2-(4-{4-[2-(2(R)-Hydroxy-2-pyridin-3-yl-ethylamino)-ethoxy]-phenyl}-oxazol-2-yl)-N,N-diisopropyl-propionamide | 467.5 |
| 1-2A | 2-[4-(4-{2-[2-(6-Chloro-pyridin-3-yl)-2(R)-hydroxy-ethylamino]-ethoxy}-phenyl)-oxazol-2-yl]-N-methyl-N-(2 ,2,2-trifluoro-ethyl)-acetamide | 479.3 |
| 1-2B | 2-[4-(4-{2-[2-(6-Chloro-pyridin-3-yl)-2( R)-hydroxy-ethylamino]-ethoxy}-phenyl)-oxazol-2-yl]-N-ethyl-N-(2,2,2-trifluoro-ethyl)-propionamide | 515.4 |
| 1-2C | N-Ethyl-2-[4-(4-{2-[2( R)-hydroxy-2-(6-methoxy-pyridin-3-yl)-ethylamino]-ethoxy}-phenyl)-oxazol-2-yl]-N-(2,2,2-trifluoro-ethyl)-acetamide hydrochloride salt | 481.5 |
| 1-2D | N-Ethyl-2-(4-{4-[2-(2(R)-hydroxy-2-pyridin-3-yl-ethylamino)-ethoxy]-phenyl}-oxazol-2-yl)-N-(2,2,2-trilluoro-ethyl)-propionamide | 513.3 |
| 1-2E | N-Ethyl-2-(4-{4-[2-(2(R)-hydroxy-2-pyridin-3-yl-ethylamino)-ethoxy]-phenyl}-oxazol-2-yl)-N-(2,2,2-tritluoro-ethyl)-propionamide hydrochloride salt | 541.3 |
| 1-2F | N-Ethyl-2-(4-{4-[2-(2( R)-hydroxy-2-pyridin-3-yl-ethylamino)-ethoxy]-phenyl}-oxazol-2-yl)-N-(2,2,2-trifluoro-ethyl )-propionamide hydrochloride salt | 523.3 |
| 1-2G | N-Ethyl-2-(4-{4-[2-(2(R)-hydroxy-2-pyridin-3-yl-ethylamino)-ethoxyj-phenyl}-oxazol-2-yl)-N-(2,2,2-trifluoro-ethyl)-acetamide tosylate salt | 507.3 |
| 1-2H | 2-[4-(4-{2-[2-(6-Chloro-pyridin-3-yl)-2(R)-hydroxy-ethylamino]-ethoxy}-phenyl)-oxazol-2-yl]-N,N-dimethyl-butyramide hydrochloride salt | 507.3 |
| 1-2I | 2-[4-(4-{2-[2-(6-Chloro-pyridin-3-yl)-2(R)-hydroxy-ethylamino]-ethoxy}-phenyl)-oxazol-2-yl]-pentanoic acid dimethylamide hydrochloride salt | 507.3 |
| 1-2J | 2-[4-(4-{2-[2-(6-Chloro-pyridin-3-yl)-2(R)-hydroxy-ethylamino]-ethoxy}-phenyl)-oxazol-2-yl]-hexanoic acid dimethylamide hydrochloride salt | 493.2 |

TABLE 1-continued

| Example No. | Compound Name | LRMS [M + H]+ |
|---|---|---|
| 1-2K | 2-[4-(4-{2-[2-(6-Chloro-pyridin-3-yl)-2(R)-hydroxy-ethylamino]-ethoxy}-phenyl)-oxazol-2-yl]-4-methyl-pentanoic acid dimethylamide hydrochloride salt | 473.1 |
| 1-2L | 2-[4-(4-{2-[2-(6-Chloro-pyridin-3-yl)-2(R)-hydroxy-ethylamino]-ethoxy}-phenyl)-oxazol-2-yl]-N,N-dimethyl-propionamide hydrochloride salt | 487.1 |
| 1-2M | 2-(4-{4-[2-(2(R)-Hydroxy-2-pyridin-3-yl-ethylamino)-ethoxy]-phenyl}-oxazol-2-yl)-N,N-dimethyl-butyramide hydrochloride salt | 501.2 |
| 1-2N | 2-(4-{4-[2-(2(R)-Hydroxy-2-pyridin-3-yl-ethylamino)-ethoxy]-phenyl}-oxazol-2-yl)-pentanoic acid dimethylamide hydrochloride salt | 501.2 |
| 1-2O | 2-(4-{4-[2-(2(R)-Hydroxy-2-pyridin-3-yl-ethylamino)-ethoxy]-phenyl}-oxazol-2-yl)-hexanoic acid dimethylamide hydrochloride salt | 549.2 |
| 1-2P | 2-(4-{4-[2-(2(R)-Hydroxy-2-pyridin-3-yl-ethylamino)-ethoxy]-phenyl}-oxazol-2-yl)-4-methyl-pentanoic acid dimethylamide hydrochloride salt | 439.2 |
| 1-2Q | 2-(4-{4-[2-(2(R)-Hydroxy-2-pyridin-3-yl-ethylamino)-ethoxy]-phenyl}-oxazol-2-yl)-N,N-dimethyl-propionamide hydrochloride salt | 453.2 |
| 1-2R | 2-[4-(4-{2-[2-(6-Chloro-pyridin-3-yl )-2(R)-hydroxy-ethylamino]-ethoxy}-phenyl)-oxazol-2-yl]-N,N-dimethyl-isobutyramide | 467.3 |
| 1-2S | 2-(4-{4-[2-(2(R)-Hydroxy-2-pyridin-3-yl-ethylamino)-ethoxy]-phenyl}-oxazol-2-yl)-N,N-dimethyl-isobutyramide hydrochloride salt | 467.2 |
| 1-2T | 2-[4-(4-{2-[2-(6-Chloro-pyridin-3-yl)-2(R)-hydroxy-ethylamino]-ethoxy}-phenyl)-oxazol-2-yl]-N-ethyl-N-(2,2,2-trifluoro-ethyl)-isobutyramide | 425.2 |
| 1-2U | N-Ethyl-2-(4-{4-[2-(2(R)-hydroxy-2-pyridin-3-yl-ethylamino)-ethoxyl-phenyl}-oxazol-2-yl)-N-(2,2,2-trifluoro-ethyl)-isobutyramide hydrochloride salt | 473.1 |
| 1-2V | 2-(4-{4-[2-(2(R)-Hydroxy-2-pyridin-3-yl-ethylamino)-ethoxy]-phenyl}-oxazol-2-yl)-N,N-dimethyl-butyramide | 439.2 |
| 1-2W | 2-(4-{4-[2-(2(R)-Hydroxy-2-pyridin-3-yl-ethylamino)-ethoxy]-phenyl}-oxazol-2-yl)-pentanoic acid dimethylamide | 555.2 |
| 1-2X | 2-(4-{4-[2-(2(R)-Hydroxy-2-pyridin-3-yl-ethylamino)-ethoxy]-phenyl}-oxazol-2-yl )-hexanoic acid dimethylamide | 521.3 |
| 1-2Y | 2-(4-{4-[2-(2(R)-Hydroxy-2-pyridin-3-yl-ethylamino)-ethoxy]-phenyl}-oxazol-2-yl)-4-methyl-pentanoic acid dimethylamide | 439.2 |
| 1-2Z | 2-(4-{4-[2-(2(R)-Hydroxy-2-pyridin-3-yl-ethylamino)-ethoxy]-phenyl}-oxazol-2-yl)-N,N-dimethyl-propionamide | 453.2 |
| 1-3A | 2-(4-{4-[2-(2(R)-Hydroxy-2-pyridin-3-yl-ethylamino)-ethoxy]-phenyl}-oxazol-2-yl)-N,N-dimethyl-butyramide hydrochloride salt | 467.3 |
| 1-3B | 2-(4-{4-[2-(2( R)-Hydroxy-2-pyridin-3-yl-ethylamino)-ethoxyll-phenyl}-oxazol-2-yl)-pentanoic acid dimethylamide hydrochloride salt | 467.2 |
| 1-3C | 2-(4-{4-[2-(2(R)-Hydroxy-2-pyridin-3-yl-ethylamino)-ethoxy]-phenyl}-oxazol-2-yl)-hexanoic acid dimethylamide hydrochloride salt | 425.2 |
| 1-3D | 2-(4-{4-[2-(2(R)-Hydroxy-2-pyridin-3-yl-ethylamino)-ethoxy]-phenyl}-oxazol-2-yl)-4-methyl-pentanoic acid dimethylamide hydrochloride salt | 439.2 |
| 1-3E | 2-(4-{4-[2-(2( R)-Hydroxy-2-pyridin-3-yl-ethylamino)-ethoxy]-phenyl}-oxazol-2-yl )-N,N-dimethyl-propionamide hydrochloride salt | 453.2 |
| 1-3F | 2-[4-(4-{2-[2( R)-Hydroxy-2-(5-methyl-pyridin-3-yl)-ethylamino]-ethoxy}-phenyl )-oxazol-2-yl]-N,N-dimethyl-propionamide hydrochloride salt | 467.2 |
| 1-3G | 2-[4-(4-{2-[2( R)-Hydroxy-2-(6-methyl-pyridin-3-yl)-ethylamino]-ethoxy}-phenyl)-oxazol-2-yl]-N,N-dimethyl-propionamide hydrochloride salt | 467.2 |
| 1-3H | 2-[4-(4-{2-[2( R)-Hydroxy-2-(6-methyl-pyridin-3-yl)-ethylamino]-ethoxy}-phenyl)-oxazol-2-yl]-N,N-dimethyl-butyramide hydrochloride salt | 425.1 |
| 1-3I | 2-[4-(4-{2-[2( R)-Hydroxy-2-(5-methyl-pyridin-3-yl)-ethylamino]-ethoxy)-phenyl)-oxazol-2-yl]-N,N-dimethyl-butyramide hydrochloride salt | 439.0 |

TABLE 1-continued

| Example No. | Compound Name | LRMS [M + H]+ |
|---|---|---|
| 1-3J | 2-[4-(4-{2-[2(R)-Hydroxy-2-(5-methyl-pyridin-3-yl)-ethylamino]-ethoxy}-phenyl)-oxazol-2-yl]-N,N-dimethyl-isobutyramide hydrochloride salt | 439.0 |
| 1-3K | 2-[4-(4-{2-[2( R)-Hydroxy-2-(6-methyl-pyridin-3-yl)-ethylamino]-ethoxy}-phenyl)-oxazol-2-yl]-N,N-dimethyl-isobutyramide hydrochloride salt | — |
| 1-3L | N-Ethyl-2-(4-{4-[2-(2( R)-hydroxy-2-pyridin-3-yl-ethylamino)-ethoxy]-phenyl}-oxazol-2-yl)-N-(2,2,2-trifluoro-ethyl)-acetamide | 453.0 |
| 1-3M | 2,2-Difluoro-2-[4-(4-{2-[2(R)-hydroxy-2-(6-methyl-pyridin-3-yl)-ethylaminoj-ethoxy}-phenyl)-oxazol-2-yl]-N,N-dimethyl-acetamide | 453.3 |
| 1-3N | 2-[4-(4-{2-[2(R)-Hyd roxy-2-(6-methyl-pyrid in-3-yl)-ethylamino]-ethoxy}-phenyl)-oxazol-2-yl]-N,N-dimethyl-propionamide | 453.3 |
| 1-3O | 2-[4-(4-{2-[2(R)-Hyd roxy-2-(6-methyl-pyridin-3-yl)-ethylamino]-ethoxy}-phenyl)-oxazol-2-yl]-N,dimethyl-butyramide | 493.2 |
| 1-3P | 2-(4-{4-[2-(2(R)-Hydroxy-2-pyridin-3-yl-ethylamino)-ethoxy]-phenyl}-oxazol-2-yl)-N,N-dimethyl-acetamide | 461.4 |
| 1-3Q | 2-[4-(4-{2-[2( R)-Hyd roxy-2-(6-methyl-pyridin-3-yl)-ethylamino]-ethoxy}-phenyl)-oxazol-2-yl]-N,N-dimethyl-acetamide hydrochloride salt | 439.3 |
| 1-3R | 2-[4-(4-{2-[2( R)-Hyd roxy-2-(6-methyl-pyrid in-3-yl)-ethylamino]-ethoxy}-phenyl)-oxazol-2-yl]-N,N-dimethyl-acetamide tosylate salt | 453.3 |
| 1-3S | 2-[4-(4-{2-[2(R)-Hyd roxy-2-(6-methyl-pyrid in-3-yl)-ethylamino]-ethoxy}-phenyl)-oxazol-2-yl]-N , N-dimethyl-acetamide mesylate salt | 411.2 |
| 1-3T | 2-[4-(4-{2-[2(R)-Hyd roxy-2-(6-methyl-pyrid in-3-yl)-ethylamino]-ethoxy}-phenyl)-oxazol-2-yl]-N-methyl-acetamide | 425.0 |

Example 2 illustrates the preparation of compounds of the present invention where Ar is a phenyl group.

Example 2
Preparation for N-{5-[2-(2-{4-[2-(2-Azetidin-1-yl-2-oxo-ethyl)-oxazol-4-yl]-phenoxy}-ethylamino)-1(R)-hydroxy-ethyl]-2-chloro-phenyl}-methanesulfonamide hydrochloride salt (2-1A)

In a round-bottomed flask, (R)-N-(2-chloro-5-oxiranyl-phenyl)-methanesulfonamide (18 mg, 0.073 mmol) and 2-{4-[4-(2-amino-ethoxy)-phenyl]-oxazol-2-yl}-1-azetidin-1-yl-ethanone (33 mg, 0.11 mmol) were dissolved in 0.7 mL of ethanol, and the mixture was heated to 80° C. for 12 hours. The solution was then concentrated in vacuo to an oil, and the crude material was purified by column chromatography (2% methanol/dichloromethane to 7% methanol/dichloromethane) to afford 16 mg (40% yield) of the coupled product as a white solid. This material was dissolved in dichloromethane and ethyl acetate (1:1), and 0.06 mL of 1 N HCl in ether was added to the solution to afford the HCl salt. This solution was concentrated to give the title compound as a yellow solid. LRMS ([M+H]+): 349.1. ¹H NMR: (400 MHz, CD₃OD): δ2.33 (m, 2H), 2.98 (s, 3H), 3.19 (m, 1H), 3.28 (s, 2H), 3.33 (m, 1H), 3.54 (m, 2H), 4.04 (m, 2H),

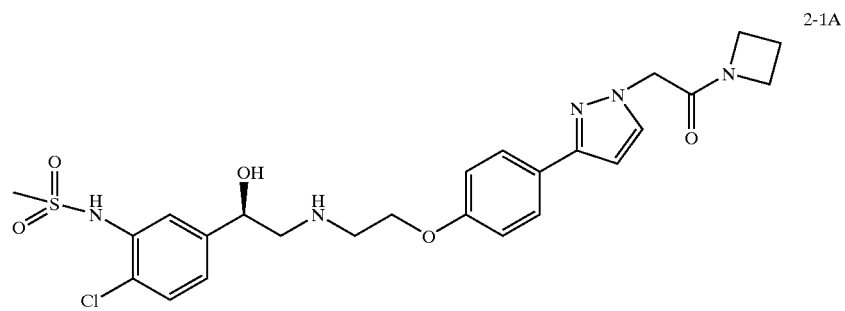

2-1A 4.33 (m, 4H), 5.02 (m, 1H), 7.05 (d, 2H, J=8.8 Hz), 7.31 (m, 1H), 7.50 (d, 1H, J=8.4 Hz), 7.64 (d, 1H, J=1.6 Hz), 7.69 (d, 2H, J=8.4 Hz), 8.13 (s, 1H).

Table II below lists compounds having the following general structure that were prepared using the general procedures described above for the preparation of compound 2-1A with the appropriate starting materials.

TABLE II

| Example No. | Compound Name | LRMS [M + H]+ |
|---|---|---|
| 2-1A | N-{5-[2-(2-{4-[2-(2-Azetidin-1-yl-2-oxo-ethyl)-oxazol-4-yl]-phenoxy}-ethylamino)-1(R)-hydroxy-ethyll-2-chloro-phenyl}-methanesulfonamide hydrochloride salt | 549.1 |
| 2-1B | 2-[4-(4-{2-[2-(3-Chloro-phenyl)-2(R)-hydroxy-ethylamino]-ethoxy}-phenyl )-oxazol-2-yl]-N-isopropyl-N-methyl-acetamide | 472.4 |
| 2-1C | 2-[4-(4-{2-[2-(3-Chloro-phenyl)-2(R)-hydroxy-ethylaminol-ethoxy}-phenyl)-oxazol-2-yl]-N-ethyl-N-isopropyl-aceta m ide | 486.2 |
| 2-1D | 2-[4-(4-{2-[2-(3-Chloro-phenyl)-2(R)-hydroxy-ethylamino]-ethoxy}-phenyl)-oxazol-2-yl]-N,N-diethyl-acetamide | 472.0 |
| 2-1E | 2-[4-(4-{2-[2-(4-Chloro-3-methanesulfonylamino-phenyl)-2(R)-hyd roxy-ethylamino]-ethoxy}-phenyl)-oxazol-2-yl]-N-ethyl-N-isopropyl-acetamide | 581.5 |
| 2-1F | 2-[4-(4-{2-[2-(4-Chloro-3-methanesulfonylamino-phenyl)-2(R)-hyd roxy-ethylamino]-ethoxy}-phenyl)-oxazol-2-yl]-N-isopropyl-N-methyl-acetamide hydrochloride salt | 565.5 |
| 2-1G | 2-[4-(4-{2-[2-(3-Chloro-phenyl)-2(R)-hydroxy-ethylamino]-ethoxy}-phenyl)-oxazol-2-yl]-N-ethyl-N-(2,2,2-trifluoro-ethyl)-acetamide hydrochloride salt | 526.4 |
| 2-1H | 2-[4-(4-{2-[2-(3-Chloro-phenyl )-2(R)-hydroxy-ethylamino]-ethoxy}-phenyl)-oxazol-2-yl]-N,N-diisopropyl-acetamide hydrochloride slat | 500.4 |
| 2-1I | 2-[4-(4-{2-[2-(4-Benzyloxy-3-di(methanesulfonyl)amino-phenyl)-2(R)-hydroxy-ethylamino]-ethoxy}-phenyl)-oxazol-2-yl]-N,N-diethyl-acetamide | 715.7 |
| 2-1J | 2-[4-(4-{2-[2-(4-Benzyloxy-3-methanesulfonylamino-phenyl)-2(R)-hydroxy-ethylamino]-ethoxy}-phenyl)-oxazol-2-yl]-N , N-diethyl-acetamide | 637.6 |
| 2-1K | N,N-Diethyl-2-[4-(4-{2-[2(R)-hydroxy-2-(4-hydroxy-3-methanesulfonylamino-phenyl)-ethylaminoj-ethoxy}-phenyl)-oxazol-2-yl]-acetamide hydrochloride salt | 547.5 |
| 2-1L | 2-[4-(4-{2-[2-(3-Chloro-phenyl)-2(R)-hydroxy-ethylamino]-ethoxy}-phenyl)-oxazol-2-yl]-N,N-dimethyl-acetamide | 444.2 |
| 2-1M | N-Ethyl-2-[4-(4-{2-[2(R)-hydroxy-2-(3-methanesulfonylamino-phenyl)-ethylamino]-ethoxy}-phenyl)-oxazol-2-yl]-N-isopropyl-acetamide | 545.6 |
| 2-1N | N-Ethyl-2-[4-(4-{2-[2(R)-hydroxy-2-(4-hyd roxy-3-methanesulfonylamino-phenyl )-ethylamino]-ethoxy}-phenyl)-oxazol-2-yi]-N-isopropyl-acetamide hydrochloride salt | 561.2 |
| 2-1O | 2-[4-(4-{2-[2-(3-Chloro-phenyl)-2(R)-hydroxy-ethylamino]-ethoxy}-phenyl)-oxazol-2-yI]-N-methyl-N-(2 ,2 ,2-trifluoro-ethyl)-acetamide hydrochloride salt | 512.2 |
| 2-1P | 2-[4-(4-{2-[2-(4-Benzyloxy-3-di(methanesulfonyl)amino-phenyl)-2(R)-hyd roxy-ethylamino]-ethoxy}-phenyl)-oxazol-2-yI]-N-ethyl-N-isopropyl-acetamide | 729.3 |
| 2-1Q | 2-[4-(4-{2-[2-(4-Benzyloxy-3-methanesulfonylamino-phenyl)-2(R)-hydroxy-ethylamino]-ethoxy}-phenyl)-oxazol-2-yl]-N-ethyl-N-isopropyl-acetamide | 651.3 |
| 2-1R | 2-[4-(4-{2-[2(R)-Hydroxy-2-(3-trifluoromethyl-phenyl)-ethylamino]-ethoxy}-phenyl)-oxazol-2-yI]-4-methyl-pentanoic acid d imethylamide hydrochloride salt | 5343 |

Example 3 illustrates the preparation of compounds of the present invention where HET is a pyrazole.

Example 3

Preparation for 2-[3-(4-{2-[2-(6-Chloro-pyridin-3-yl)-2(R)-hydroxy-ethylamino]-ethoxy}-phenyl)-pyrazol-1-yl]-1-pyrrolidin-1-yl-ethanone (3-1A)

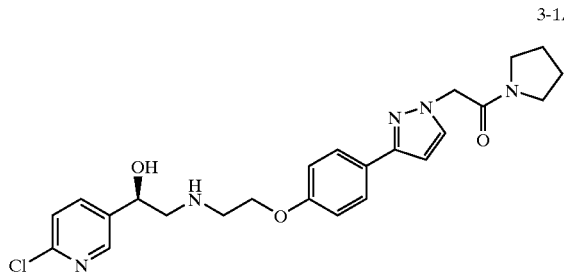

In a round-bottomed flask, (R)-2-chloro-5-oxiranyl-pyridine (23 mg, 0.15 mmol) and 2-{4-[1-(2-amino-ethoxy)-phenyl]-pyrazol-1-yl}-1-pyrrolidin-1-yl-ethanone I-4f (71 mg, 0.23 mmol) were dissolved in 1.5 mL of ethanol, and the mixture was heated to 80° C. for about 16 hours. The solution was then concentrated in vacuo to an oil, and the crude material was purified by column chromatography (dichloromethane to 11% methanol/dichloromethane) to afford 45 mg (63% yield) of the title product as a white solid. LRMS ([M+H]$^+$): 470.0.

$^1$H NMR: (400 MHz, CD$_3$OD): δ1.91 (m, 2H), 2.03 (m, 2H), 2.88 (m, 2H), 3.05 (m, 2H), 3.46 (t, 2H, J=6.8 Hz), 3.59 (t, 2H, J=6.7 Hz), 4.12 (m, 2H), 4.86 (m, 1H), 5.04 (s, 2H), 6.59 (d, 1H, J=4.5 Hz), 6.96 (d, 2H, J=8.0 Hz), 7.43 (d, 1H, J=8.4 Hz), 7.62 (d, 1H, J=2.8 Hz), 7.69 (d, 2H, J=8.0 Hz), 7.85 (dd, 1H, J=2.5, 8.3 Hz), 8.35 (d, 1H, J=2.2 Hz).

Table III below lists compounds that were prepared using the general procedures described above for the preparation of compounds 3-1A with the appropriate starting materials.

TABLE III

| Example No. | Compound Name | LRMS [M + H]$^+$ |
|---|---|---|
| 3-1A | 2-[3-(4-{2-[2-(6-Chloro-pyridin-3-yl)-2(R)-hydroxy ethylamino]-ethoxy}-phenyl)-pyrazol-1-yl]-1-pyrrolidin-1-yl-ethanone | 470.0 |
| 3-1B | 2-[3-(4-{2-[2-(6-Chloro-pyridin-3-yl)-2(R)-hydroxy-ethylamino]-ethoxy}-phenyl)-pyrazol-1-yl]-1-morpholin-4-yl-ethanone | 486.0 |
| 3-1C | 2-(3-{4-[2-(2(R)-Hydroxy-2-pyridin-3-yl-ethylamino)-ethoxy]-phenyl}-pyrazol-1-yl)-1-pyrrolidin-1-yl-ethanone hydrochloride salt | 436.3 |
| 3-1D | 2-(3-{4-[2-(2 (R)-Hydroxy-2-pyridin-3-yl-ethylamino)-ethoxyl-phenyl}-pyrazol-1-yl)-1-morpholin-4-yl-ethanone hydrochloride salt | 452.3 |
| 3-1E | 2-[3-(4-{2-[2-(6-Chforo-pyridin-3-yl)-2(R)-hydroxy-ethyiamino]-ethoxy}-phenyl)-pyrazol-1yl]-1-piperidin-1-yl-ethanone | 484.2 |
| 3-1F | 2-[3-(4-{2-[2-(6-Ch loro-pyridin-3-yl )-2(R)-hydroxy-ethylamino]-ethoxy}-phenyl)-pyrazol-1-yl]-N-cyclopentyl-acetamide | 484.2 |
| 3-1G | 2-[3-(4-{2-[2-(6-Chloro-pyridin-3-yl )-2(R)-hydroxy-ethylamino]-ethoxy}-phenyl)-pyrazol-1-yl]-N-ethyl-N-methyl-acetamide | 458.2 |
| 3-1H | N-Cyclopentyl-2-(3-{4-[2-(2(R)-hydroxy-2-pyridin-3-yl-ethylamino)-ethoxy]-phenyl}-pyrazol-1-yl)-acetamide hydrochloride salt | 450.4 |
| 3-1I | N-Ethyl-2-(3-{4-[2-(2(R)-hydroxy-2-pyridin-3-yl-ethylamino)-ethoxy]-phenyl}-pyrazol-1-yl)-N-methyl-acetamide hydrochloride salt | 424.4 |
| 3-1J | 2-[3-(4-{2-[2-(6-Chloro-pyridin-3-yl)-2(R)-hydroxy-ethylamino]-ethoxy}-phenyl )-pyrazol-1-yl]-N,N-dimethyl-acetamide | 444.2 |
| 3-1K | 2-(3-{4-[2-(2(R)-Hydroxy-2-pyridin-3-yl-ethylamino)-ethoxy]-phenyl}-pyrazol-1-yl)-N,N-dimethyl-acetamide hydrochloride salt | 410.4 |

Biological Assays

The utility of the compounds of the present invention, in the practice of the methods of the instant invention, can be evidenced by activity in at least one of the protocols described in detail below.

Assay 1

$\beta_3$ Receptor Selectivity Over $\beta_1$ and $\beta_2$ Adrenergic Receptors In vitro $\beta_3$ receptor agonist activity and selectivity over $\beta_1$ and $\beta_2$ adrenergic receptors may be determined by measurement of cyclic adenosine monophosphate (cAMP) accumulation in Chinese hamster ovary cells.

Chinese hamster ovary cells uniquely transfected with the cDNA for the human $\beta_1$, $\beta_2$, or $\beta_3$ adrenergic receptor are grown to confluence in Ham's F12 media (Gibco BRL, Life Technologies, Inc., Grand Island, N.Y.) containing 10% fetal bovine serum, 500 mg/ml geneticin, 100 U/ml penicillin, 100 mg/ml streptomycin, and 250 ng/ml fungizone according to the procedure described in American Type Culture Catalog of Cell Lines and Hybridomas, Seventh Edition, 1992, p. 36, ATCC CCL 61 CHO-K1. Compounds are prepared as 25 mM stock solutions in DMSO (0.1% DMSO final concentration), diluted in Ham's F12 media and added to the cells at $10^{-10}$ to $10^{-5}$ M along with $10^{-5}$ M isobutylmethylxanthine to inhibit phosphodiesterase activity. The media and cells are then incubated for sixty minutes at 37° C. At the end of the incubation period, the media is aspirated and the cells lysed in 0.01 N HCl. The cellular content of cAMP is then determined by radioimmunoassay (RIA) using a kit from New England Nuclear (Burlington, Mass.). There is a direct correlation between the cellular content of cAMP and the agonism of the $\beta_1$, $\beta_2$, or $\beta_3$ adrenergic receptor. The non-selective, full $\beta$-adrenergic agonist isoproterenol is included as a positive control at $10^{-5}$ M.

A range of $EC_{50}$ values from 13 µM to 155 µM were observed for the compounds listed in Examples 1, 2 and 3 (Example 1-1A through Example 3-1K). As a specific example, the compound of Example 3-1H had an $EC_{50}$ of 88 µM. Example 3-1H was chosen for illustrative purposes only and does not imply that the compound of Example 3-1H is a preferred compound.

Assay 2

Many G protein-coupled receptors (GPCRs) exhibit at least two agonist affinity states. High affinity agonist binding to GPCRs requires the association or coupling of the receptor with the GDP-bound heterotrimeric G protein complex. In general, the low affinity agonist binding site is indicative of the uncoupled receptor state. The high affinity agonist binding site can be converted to the low affinity site by addition of GTP or its analogs. In the absence of agonist, G proteins display high affinity for GDP. In the presence of agonist, G proteins display high affinity for GTP. Thus, when agonist and GTP are added to the receptor/G protein complex, GTP displaces GDP and uncouples the receptor from the G protein. Two affinity states for agonists can be detected in radioligand competetion binding assays. A two-site fit is generally observed for agonists for many GPCRs and can be calculated using commercially available software. The high affinity site ($K_{iH}$) corresponds to the G protein-coupled state and, in the case of $\beta_3$-adrenergic receptors correlates well with the functional $ED_{50}$ for stimulation of cAMP accumulation.

In order to identify compounds that attenuate the binding of [$^{125}$I]cyanopindolol (ICYP) to $\beta_3$ adrenergic receptors, the following radioligand binding assay can be used.

Radioligand Binding Assays

ICYP $\beta_3$ Adrenergic Receptor Competition Binding Assay

The specific activity of [$^{125}$I]ICYP is 2000 Ci/mmole. ICYP undergoes catastrophic decay upon radiolysis. Therefore, the specific activity always remains at 2000 Ci/mmole, but the concentration will decrease over time. The final concentration of ICYP is 250 pM. Therefore, a 2.5 nM (10×) stock needs to be made. [$^{125}$I]CYP can be obtained from New England Nuclear, Boston, Mass.

Competitors

Up to four compounds can be tested in thirteen competition curves in a 96 well format. An example for a single compound is outlined below.
[Comp 1]
A 1,2 −10
B 1,2 −9.3
C 1,2 −9
D 1,2 −8.3
E 1,2 −8
F 1,2 −7.3
G 1,2 −7
H 1,2 −6.3
A 3,4 −6
B 3,4 −5
C 3,4 −4
D 1,3 pindolol
E 3,4 TOTAL The next compound would begin in F 3,4. Two pairs of totals and non-specific binding are added to the plates. Wells E 3,4 and G 7,8 are for total cpm bound. Wells D 3,4 and H 7,8 are for 100 µM pindolol to determine non-specific binding.

To each well in order add: 20 µl buffer to "total" wells; 20 µl 1 mM pindolol to pindolol wells; 20 µl of each concentration of compound to the appropriate wells; 20 µl of 2.5 nM ICYP to all wells; and 160 µl membranes diluted to 15 µg/160 µl.

Procedure

1. Set up assay for Packard 96 well Unifilter with GF/C filters (Packard; Meriden, Conn.) using a 96 well microtiter plate.

2. Incubate 90–120 minutes with shaking at room temperature

3. Using Packard cell harvester (Packard; Meriden, Conn.), aspirate samples into processing head. Use a pre-soaked (0.3% PEI) filter.

4. Wash four times with cold wash buffer.

5. Dry plate, and add 25 µl Microscint (ICN Manufacturers; Costa Mesa, Calif.) to each well.

6. Count samples in Wallac beta plate reader (Wallac; Turku, Finland).

Binding Buffer: 50 mM Hepes/10 mM $MgCl_2$, pH 7.4 (prepared from 10× stock solution) and 0.2% BSA (fraction V)

Protease inhibitors (prepared as 100× stock solution): 100 µg/ml bacitracin; 100 µg/ml benzamidine; 5 µg/ml aprotin; and 5 µg/ml leupeptin.

Wash Buffer: 50 nM Hepes/10 mM $MgCl_2$, pH 7.4, ice cold (prepared from 10× stock solution)

Assay 3

Oxygen Consumption

As will be well known to one of ordinary skill in the art, during increased energy expenditure, animals generally consume increased amounts of oxygen. In addition, metabolic fuels such as, for example, glucose and fatty acids, are oxidized to $CO_2$ and $H_2O$ with the concomitant evolution of heat, an effect commonly referred to in the art as thermogenesis. Accordingly, the measurement of oxygen consumption in animals, including humans and companion animals, is an indirect measure of thermogenesis, and indirect calorimetry may be commonly used in animals, e.g., humans, by one of ordinary skill in the art, to measure such energy expenditures.

The ability of the compounds of Formula (I), the stereoisomers and prodrugs thereof, and the pharmaceutically acceptable salts of the compounds, stereoisomers, and prodrugs, to generate a thermogenic response may be demonstrated according to the following protocol using male Sprague-Dawley rats (Charles River, Wilmington, Mass.).

Whole animal oxygen consumption may be measured using an open circuit, indirect calorimeter (Oxymax™, Columbus Instruments, Columbus, Ohio). The gas sensors are calibrated with nitrogen gas and gas mixture (0.5% carbon dioxide, 20.5% oxygen, 79% nitrogen; Abco Industrial Supplies, Waterford, Conn.) before each experiment. Male Sprague-Dawley rats (300–380 g body weight) are placed in sealed chambers (43×43×10 cm) of the calorimeter and the chambers placed in activity monitors. Air flow rate through the chambers is set at 1.6–1.7 l/min. The calorimeter software calculates the oxygen consumption (ml/kg/hour) based on the flow rate of air through the chambers and the difference in oxygen content at inlet and outlet ports. The activity monitors have fifteen infrared light beams spaced one inch apart on each axis; ambulatory activity is recorded when two consecutive beams are broken (repeated interruptions of the same beam are not registered) and the results are recorded as counts. Basal oxygen consumption and ambulatory activity are measured every ten minutes for two and one-half to three hours. At the end of the basal period, the chambers are opened and the test compound (0.01–20 mg/kg, prepared in water, 0.5% methyl cellulose, or other suitable vehicle) or an equivalent amount of vehicle is administered by oral gavage. Oxygen consumption and ambulatory activity are measured every ten minutes for an additional two to six hours post-dosing. Percent change in oxygen consumption is calculated by averaging the post-dosing values and dividing by basal oxygen consumption (average of the pre-dosing values except the first hour). Oxygen consumption values obtained during time periods where ambulatory activity exceeds 100 counts are excluded from the calculation. Thus, the values represent % change in resting oxygen consumption.

Assay 4

Hypoglycemic Activity

The compounds of the present invention may be tested for hypoglycemic activity accoprding to the following procedure, and as an aid in determining dosages when compared to other test compounds and standards.

Five to eight-week old C57 BL/6J-ob/ob mice (Jackson Laboratory, Bar Harbor, Me.) are housed five animals per cage at an ambient temperature of 66° C. under standard animal care practices. After a one week acclimation period, the animals are weighed and 25 microliters of blood is collected via an occular bleed prior to any treatment. The blood sample is immediately diluted 1:5 with saline containing 2% sodium heparin, in tubes held on ice. Blood samples are centrifuged for two minutes to remove red blood cells and the supernatant is analyzed for glucose concentration using a clinical autoanalyzer (Abbott Spectrum® CCx; Abbott Laboratories, Abbott Park, Ill.). Animals are then regrouped, in groups of five animals per cage, such that the mean glucose values of the groups are similar. The mice are then dosed once or twice daily for five days with test compound (0.01–20 mg/kg), with a positive control such as englitazone or ciglitazone (50 mg/kg p.o.) (U.S. Pat. No. 4,467,902; Sohda et al., Chem. Pharm. Bull., 32, 4460–4465, (1984)), or with vehicle. All compounds are administered by oral gavage in a vehicle consisting of 0.5% w/v methyl cellulose, or with other suitable vehicle. On Day 5, the animals are weighed again and bled (via the occular route) for blood glucose levels as described hereinabove.

Plasma glucose is then calculated by the equation:

Plasma Glucose (mg/dl)=Sample Value×5×1.67=8.35× Sample Value, where 5 is the dilution factor and 1.67 is the plasma hematocrit adjustment (assuming the hematocrit is 40%).

The animals dosed with vehicle maintain substantially unchanged hyperglycemic glucose levels (e.g. 300 mg/dl), while positive control animals have depressed glucose levels (e.g. 130 mg/dl). The glucose lowering activity of test compounds is expressed in terms of % glucose normalization. For example, a glucose level which is the same as the positive control is expressed as 100%.

Assay 5

$\beta_1$ and $\beta_2$ Receptor Selectivity

In vivo selectivity for $\beta_1$ and $\beta_2$ receptors may be determined by measurements of heart rate, blood pressure, and plasma potassium concentration gathered on conscious catheterized rats (male, Sprague-Dawley, 300–400 g body weight). To implant catheters, rats are anesthetized with pentobarbital (50–60 mg/kg i.p.) and the left carotid artery is cannulated with PE50 tubing. The catheter is tunneled subcutaneously, exteriorized at the back of the neck, filled with a solution of polyvinylpyrrolidone in heparinzied saline, flame sealed, and taped. Experiments are performed seven days after surgery. On the day of the experiment, the catheters are untaped and flushed with saline. After at least thirty minutes, basal values for heart rate and blood pressure are measured by attaching the catheter to a pressure transducer, the results recorded on a Grass Model 7 polygraph (Grass Medical Instruments, Quincy, Mass.), and a basal blood sample (0.5 ml) is obtained from the arterial catheter. After obtaining basal values, the test compound or vehicle is administered by oral gavage and blood pressure (measure of $\beta_2$ activity) and heart rate (measure of $\beta_1$ activity) measurements are taken at 15, 30, 45, and 60 minutes, and blood samples for potassium determination ($\beta_2$) are obtained at 30 and 60 minutes. Isoproterenol, a non-selective $\beta$-agonist, can be tested as a positive control at doses ranging from 0.001 to 1 mg/kg (injected s.c. in saline vehicle). Plasma potassium is determined by flame spectrophotometry. To determine changes, basal values are subtracted from the average of the post-dosing values.

Assay 6

Reducing Intestinal Motility

The compounds of Formula (I) have the effect of reducing intestinal motility and thus have utility in aiding in the treatment of various gastrointestinal disorders such as irritable bowel syndrome, peptic ulceration, esophagitis, gastritis, duodenitis (including that induced by *Helicobacter pylori*), intestinal ulcerations (including inflammatory bowel disease, ulcerative colitis, Crohn's Disease and proctitis), and gastrointestinal ulcerations. It has been proposed that the motility of non-sphincteric smooth muscle contraction is mediated by activity at $\beta_3$ adrenergic receptors. The availability of a $\beta_3$ specific agonist, with little activity at $\beta_1$ and $\beta_2$ receptors, will assist in the pharmacologic control of intestinal motility without concurrent cardiovascular effects.

In vivo activity of the compounds of Formula (I) for the treatment or prevention of intestinal motility disorders can be determined according to the following procedures. Eighteen-hour fasted male Sprague-Dawley derived (CD) rats (175–225 g) are dosed with 0.01–20 mg/kg p.o. of test compound or vehicle (distilled water). Thirty minutes after administration of test compound, the rats are orally dosed with 0.25 ml of a solution of sodium chromate in 0.9% saline containing about 20,000 cpm of $^{51}$Cr (specific activity 350 mCi/mg Cr). Twenty minutes later, the rats are sacrificed, the gastroesophageal, pyloric, and ileocecal junctions are then ligated, and the stomachs and small intestines are removed. The small intestines are then divided into ten equal lengths, and the stomach and each length of intestine assayed for radioactivity with a gamma counter. Gastric emptying rate may then be determined for each rat by comparing the amount of radioactivity in the intestine relative to the total in the intestine plus stomach. In addition, the geometric center of the distribution of the radioactive marker is then used as a measure of the overall transit rate through the stomach and intestine. The geometric center is calculated by summing the products of the fractions of $^{51}$Cr in each segment times the segments number: geometric center=S ((fraction of $^{51}$Cr per segment)×(segment number)). For these calculations, the stomach is considered segment number 0, and and the ten intestinal segments as numbers 1 to 10. Thus, a geometric center of 0.0 indicates that the entire load of $^{51}$Cr remains in the stomach. Data from the two experiments are pooled, and statistical evaluations are made using Dunnett's multiple comparison test.

Alternatively, in groups of eight, overnight-fasted male Sprague-Dawley (CD) rats (175–225 g) may be anesthetized with methoxyflurane. A small abdominal incision is then made, and the pylorus ligated. Immediately after the ligation, a solution of the test compound or vehicle (distilled water) is injected into the proximal duodenum. The doses of test compound used should be 0.01–20 mg/kg body weight. The incisions are then closed and the rats allowed to recover from the anesthesia. Two hours after the ligation, the rats are sacrificed and the gastric fluid collected and cleared by centrifugation. Total volume of secretion is determined by weight, and acidity is determined by titration to pH 7.0 with 0.1 N sodium hydroxide using an automatic titrator. The data from two experiments are then pooled. A group of rats treated with 10 mg/kg of of the anti-secretory histamine $H_2$-receptor antagonist cimetidine may be included as a positive control. Statistical evaluations can be made using Student's t-test.

In vitro activity for relaxation of contracted ileum from isolated guinea pig ileum is determined according to the following procedures. Fresh, isolated segmerits of guinea pig ileum (about 1.5 cm in length) are mounted in tissue baths containing Tyrode's physiological salt solution at about 30° C. and aerated continuously with oxygen:carbon dioxide (95%:5%). Tissues are then equilibrated for 60–90 minutes under 4.0 gm tension in order to achieve stable baselines. Histamine is then added to the baths and in a cumulative fashion in concentrations ranging from 1 nM to 10 mM. The maximum tension generated after each addition of histamine is recorded on a Grass Physiograph (Grass Medical Instruments, Quincy, Mass.). The tissues are then washed with several changes of Tyrode's solution, basal tension is readjusted to 4.0 gm, and a stable baseline is then again obtained. Each tissue is then exposed to a single concentration of a test compound (1 nM–10 mM) or vehicle and, after a thirty minute equilibration period, the histamine dose response curve is then repeated. Results from multiple experiments are standardized (0–100%) to the maximum response of the control tissues and plotted as percent maximum tension vs. the log of the histamine concentration in the absence and presence of the test compound.

Assay 7

Protection Against Gastric Ulceration

Food (but not water) is withheld from female Sprague-Dawley rats (Charles River, Wilmington, Mass.) weighing 70–120 g. Access is then permitted to food for ninety minutes. A single dose of test compound is then administered p.o. (0.01–20 mg/kg in a dosing volume of 1 ml/100 g), and indomethacin (Sigma Chemical Co., St. Louis, Mo.) (60 mg/kg, 1 ml/100 g body weight) is then injected subcutaneously. Control rats receive the subcutaneous injection of indomethacin and oral administration of vehicle (0.5% methyl cellulose in distilled water) for the β-adrenoceptor agonist. The animals are then allowed continued access to food but water is withdrawn. The animals are then sacrificed by cervical dislocation six hours after dosing with indomethacin. The stomach are then removed, opened along the greater curvature and washed in 0.9% saline. An assessment of gastric damage is carried out by an observer who is unaware of the dosing regimen. A transparent plastic grid divided into 1 mm$^2$ sections is placed over the antrum and the area of macroscopic damage assessed as the total area of visible lesions in mm$^2$. This value is then expressed as a percentage of the total antral area.

Assay 8

Anti-Depressant Activity

Male CD1 mice weighing between 20 and 25 g, and Sprague-Dawley rats weighing between 200 and 250 g are obtained from Charles River, Wilmington, Mass. Test compounds of Formula (I) are dissolved in water. The compounds are administered to mice in a volume of 10 ml/kg, and to rats in a volume of 2 ml/kg. Control animals receive the vehicle. Positive test results for the following parameters indicate anti-depressant activity.

(1) Antagonism of Hypothermia Induced by Reserpine

Mice are administered reserpine (2.5 mg/kg i.p. dissolved in 1% citric acid). Their rectal temperatures are measured three and one-half hours later. The mice are then divided into different groups so as to obtain the same mean rectal temperature in each group. One-half hour later, (i.e., four hours after reserpine administration), the mice are given the vehicle or test compound. Rectal temperature is measured again ninety minutes later (i.e., five hours and thirty minutes after reserpine administration) (Bourin, et al., The Value of the Reserpine Test in Psychopharmacology, Arzneim. Forsch., 33, 1173, (1983)).

(2) Antagonism of Hypothermia Induced by Apomorphine

One-half hour after the mice are placed in individual cages, their rectal temperatures are recorded. The animals are allocated so as to obtain the same mean rectal temperature in each group. Apomorphine (16 mg/kg s.c.) is given thirty minutes after the test compound or vehicle. Rectal temperature is then measured again thirty minutes after the apomorphine treatment (Puech, et al., Antagonism of Hypothermia and Behavioral Response to Apomorphine; A Simple, Rapid, and Discriminating Test for Screening Anti-Depressants and Neuroleptics, Psychopharmacology, 75, 84, (1981)).

(3) Effect on Learned Helplessness Behavior

This test is performed essentially as described by Giral, et al., Reversal of Helpless Behavior in Rats by Putative 5-$HT_{1A}$ Agonists, Biol. Psychiat., 23, 237 (1988). Electric footshocks are delivered to male albino Sprague-Dawley rats placed in chambers (20×10×10) with Plexiglass® walls and covers. The floors are made of stainless-steel grids (1.5 cm mesh). A constant-current shock is delivered as sixty scrambled, randomized inescapable shocks (15 sec. duration, 0.8 mA, every 60+15 sec.) to the grid floor. Control rats are then placed in identical chambers, but no shock is administered. All preconditioning trials are performed on Day 1 between 9 and 11 a.m. Avoidance training is initiated 48 hours (Day 3) after inescapable shock in automated two-way shuttle boxes (60×21×30 cm) with Plexiglass® walls and a floor consisting of stainless-steel rods spaced 1.0 cm apart in order to evaluate escape deficits. Each shuttle box is divided into two chambers of equal size by a stainless-steel partition with a gate providing access to the adjacent compartment through a 7×7 cm space. Shuttle box sessions are performed for three consecutive days (Days 3, 4, and 5). The animals are placed individually in the shuttle box and allowed to habituate to the environment for five minutes (for the first session only) and then subjected to thirty trials. The intertrial interval should be thirty seconds. A light signal, used as a conditioned stimulus, is presented during the first three seconds of each trial. Crossing the gate into the other compartment of the box during this "conditioned stimulus only" period (referred to as avoidance response) allows rats to avoid shocks. A period with conditioned stimulus plus foot-shock (0.8 mA) may be presented if an avoidance response does not occur. Crossing the gate into the other compartment during this conditioned stimulus plus shock period is referred to as an escape response. Absence of escape response during the three-second duration conditioned stimulus plus shock is considered to be an escape failure.

The rats (n=10 per group) are treated randomly according to one of the following protocols: the control sample, which receives no shock, and is given only vehicle, or experimental animals with inescapable shock are treated daily with vehicle or test compound. Animals are treated orally over five consecutive days, i.e. six hours after shock pretreatment on Day 1, and then twice per day, a half dose in the morning (30 minutes before shuttle box session) and half a dose in the afternoon (except on day 5). Statistical analysis is performed on the mean number of escape failures using a two-way analysis of variance (subjects×sessions) followed by Dunnett's test.

Assay 9

Bronchial Relaxation and Ciliary Motility

In vitro activity of the compounds of Formula (I) for the treatment of airway inflammatory disorders, such as asthma and obstructive lung disease, may be determined by measurement of guinea pig bronchial ring relaxation according to the following procedure.

Guniea pig bronchial rings are obtained from tricolored guinea pigs of either sex (250–350 g), anesthized with urethane (1.25 g/kg) and suspended under an initial tension of 2.0 g in Krebs solution at 37° C. gassed with 95% oxygen:5% carbon dioxide. After about one hour of equilibration, the guinea pig bronchial rings are contracted with acetylcholine ($10^{-3}$ M), relaxed to maximal relaxation with theophylline ($10^{-3}$ M), and then allowed to equilibrate for a further sixty minutes while they are washed with Krebs solution every fifteen minutes.

Changes in tension are measured isometrically with strain guages and amplifiers and displayed on a recorder. The composition of the Krebs solution is (mM):NaCl 118.0, FCl 5.4, $CaCl_2$, 2.5, $KHPO_4$ 1.2, $MgSO_4$ 1.2, $NaHCO_3$ 25.0, and glucose 11.7.

To test effects of test compounds on resting tension, cumulative concentration-response curves are obtained by addition of the test compounds ($10^{-9}$–$10^{-6}$ M) every ten to twenty minutes until a plateau is reached. The relaxant effects of the test compounds are expresed as percentages of the maximal relaxations induced bytheophylline ($3\times10^{-3}$ M).

Assay 10

Prostate Disease

Ventral prostates of male Sprague-Dawley rats (300–400 g) anesthetized with diethyl ether are quickly excised and placed in oxygenated Krebs solution. While maintained at room temperature in this buffer, adherent fatty and connective tissues are removed. The prostates are then suspended in 10 ml organ baths containing Krebs solution warmed to 37° C. and aerated with a mixture of 95% oxygen and 5% carbon dioxide. The composition of the Krebs solution is 118.4 mM NaCl, 4.7 mM KCl, 1.2 mM $MgSO_4$, 2.5 mM $CaCl_2$, 11.1 mM dextrose, 25.0 mM $NaHCO_3$ and 1.2 mM $KH_2PO_4$, dissolved in distilled and demineralized water. The tissues are attached to isometric force-displacement transducers and isometric contraction is recorded under a loading tension of 0.5 g. Equilibration is undertaken for one or two hours before the addition of test compounds. Submaximal contractions are first elicited by repeated concentrations of $1\times10^{-6}$M phenylephrine until constant responses are obtained. The control and test compound-treated experiments are performed in different preparations. A concentration-response curve to cumulate concentrations of phenylephrine or acetylcholine ($10^{-9}$ to $10^{-4}$M) is determined. For testing compounds, a concentration response curve to phenylephrine or acetylcholine is determined in the presence of the compounds.

In vitro activity of compounds of Formula (I) can also be determined for specific efficacy in human prostate as follows.

Prostatic tissue specimens are obtained from patients with symptomatic BPH, who are undergoing open prostatectomy. Isolated human prostatic tissue is cut into five to eight strips (3 mm wide, 3 mm thick and 15 mm long in each strip). The strips are mounted vertically in organ baths containing 20 ml Krebs-Henseleit solution of the following composition (mM): NaCl 112, KCl 5.9, $MgCl_2$ 1.2, $CaCl_2$ 2, $NaHCO_3$ 25, $NaHPO_4$ 1.2, glucose 11.5. The medium is maintained at 37° C. and at pH 7.4, and is equilibrated with a gas mixture consisting of 95% oxygen and 5% carbon dioxide. A resting tension of 0.5 g is applied and the responses are recorded isometrically through a force-displacement transducer. The preparations are equilibrated for ninety minutes before starting the experiments.

Concentration-response curves for phenylephrine or acetylcholine ($10^{-9}$ to $10^{-4}$M) are determined by adding the compound directly to the bathing media in a cumulative fashion. For testing compounds, the prostate strips are incubated in the presence of compound (1 or 10 $\mu$M) for thirty minutes before and then phenylephrine or acetylcholine are added to the medium in a cumulative fashion to obtain to the concentration-response curve in the presence of the compound.

Assay 11

Effect on Trigylceride Levels and Dyslipidemia

Compounds of the Formula (I) lower triglyceride levels and cholesterol levels and raise high density lipoprotein levels and are therefore of use in combating medical conditions wherein such lowering (and raising) is thought to be beneficial. Thus, the compounds of Formula (I) can be used in the treatment of hypertriglyceridaemia, hypercholesterolemia, and conditions of low HDL (high density lipoprotein) levels in addition to the treatment of atherosclerotic disease such as of coronary, cerebrovascular and peripheral arteries, cardiovascular disease and related conditions.

Activity of compounds of Formula (I) for dyslipidemia can be determined according to the following procedure. C57BL/6J ob/ob mice (male, 30–40 g body weight, Jackson Lab, Bar Harbor, Me.), housed 5 mice per cage in an environmentally controlled room, are dosed once or twice daily for three weeks with test compound (0.01–20 mg/kg, n=15 per group) or vehicle (0.5% w/v methyl cellulose/ distilled water, water, or other suitable vehicle) by oral gavage. At the end of the study, twenty-four hours after giving the final dose of compound, the mice are sacrificed by decapitation and blood collected. Plasma concentrations of free fatty acids and triglyceride are determined using a clinical autoanalyzer (Abbott Spectrum® CCx; Abbott Laboratories, Abbott Park, Ill.).

Assay 12

Decrease in Body Fat

Activity of compounds of the present invention for decrease in body fat can be determined according to the following procedure. C57BL/6J ob/ob mice (male, 30–40 g body weight, Jackson Lab, Bar Harbor, Me.) are housed five mice per cage in an environmentally controlled room with food (pelleted rodent chow) and water available ad libitum. The compound or vehicle (0.5% w/v methyl cellulose/ distilled water, water, or other suitable vehicle) is dosed once or twice daily for) three weeks (0.01–20 mg/kg, n=15 per group) by oral gavage. Body weight of each mouse is measured daily and food intake per cage determined by weighing the amount of food left in the trough. At the end of the study, twenty-four hours after giving the final dose of compound, the mice are weighed and then sacrificed by cervical dislocation. The epididymal fat pads from each mouse are excised and weighed. The fat versus body weight ratio is determined for each mouse using the absolute body weights and the fat pad weights. A reduction in fat pad weight is indicative of a reduction in total body fat.

What is claimed is:

1. A compound of Formula (I)

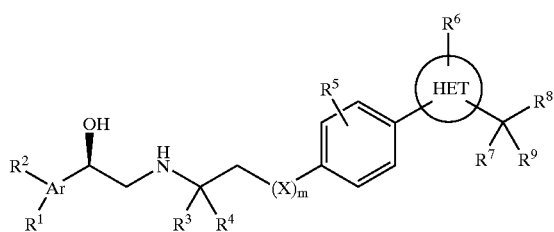

(I)

wherein

Ar is pyridyl;

$R^1$ and $R^2$ are each independently hydrogen, hydroxy, halogen, cyano, nitro, —$NR^{1a}R^{2a}$, —$NR^{1a}SO_2R^{2a}$, —$OR^{1a}$, —$SO_2R^{2a}$, —$CF_3$, $(C_3–C_8)$cycloalkyl, phenyl, —$NR^{1a}COR^{2a}$, —$COR^{2a}$, or $(C_1–C_6)$alkyl optionally substituted with one or more substituents selected from the group consisting of hydroxy, nitro, halogen, and cyano, where $R^{1a}$ and $R^{2a}$ are each independently hydrogen, $(C_3–C_8)$cycloalkyl, phenyl optionally substituted with 1 to 3 substituents selected from the group consisting of halo, $(C_1–C_6)$alkyl, and $(C_1–C_6)$alkoxy, or $(C_1–C_6)$alkyl optionally substituted with 1 to 3 substituents selected from the group consisting of hydroxy, fluoro, —$CO_2H$, phenyl, and —$NR^{1b}R^{2b}$, where $R^{1b}$ and $R^{2b}$ are each independently hydrogen, amino, amino$(C_1–C_6)$alkyl, aminoaryl, $(C_1–C_6)$alkyl optionally substituted with one or more substituents selected from the group consisting of hydroxy, $(C_1–C_6)$alkoxy, fluoro, amino, $(C_1–C_6)$ alkylamino, and acyl, or $(C_3–C_8)$cycloalkyl optionally substituted with one or more substituents selected from the group consisting of fluoro, alkyl, $(C_1–C_6)$alkoxy, hydroxy, amino, aminoalkyl-, acyl, and amido;

$R^3$ and $R^4$ are each, independently, hydrogen, or $(C_1–C_6)$ alkyl optionally substituted with 1 to 3 substituents selected from the group consisting of hydroxy, $(C_1–C_6)$ alkoxy, and fluoro;

$R^5$ is hydrogen, $(C_1–C_6)$alkyl optionally substituted with 1 to 3 substituents selected from the group consisting of hydroxy, $(C_1–C_6)$alkoxy, and fluoro;

$R^6$ and $R^7$ are each independently hydrogen, halogen, or $(C_1–C_6)$alkyl optionally substituted with one or more substituents selected from the group consisting of hydroxy, $(C_1–C_6)$alkoxy, or fluoro;

$R^8$ is —$CONR^{1b}R^{2b}$, —$SOR^{1b}$, —$SO_2R^{1b}$, —$SO_2NR^{1b}R^{2b}$, —$NR^{1b}SO_2R^{2b}$, or —$CO_2R^{1b}$;

$R^9$ is hydrogen, halogen, $(C_1–C_6)$alkoxy, or $(C_1–C_6)$alkyl optionally substituted with one or more substituents selected from the group consisting of fluoro, hydroxy, and $(C_1–C_6)$alkoxy;

X is —O;

m is 1; and

HET is oxazole;

a pharmaceutically acceptable salt thereof, a prodrug of said compound or said salt, or a solvate or hydrate of said compound, said salt or said prodrug.

2. The compound of claim 1 wherein $R^5$ and $R^6$ are both hydrogen;

a pharmaceutically acceptable salt thereof, a prodrug of said compound or said salt, or a solvate or hydrate of said compound, said salt or said prodrug.

3. The compound of claim 1 wherein $R^8$ is —$CONR^{1b}R^{2b}$, and $R^7$ and $R^9$ are each independently hydrogen, fluoro, or $(C_1–C_6)$alkyl;

a pharmaceutically acceptable salt thereof, a prodrug of said compound or said salt, or a solvate or hydrate of said compound, said salt or said prodrug.

4. The compound of claim 3 where $R^5$ and $R^6$ are both hydrogen;

a pharmaceutically acceptable salt thereof, a prodrug of said compound or said salt, or a solvate or hydrate of said compound, said salt or said prodrug.

5. The compound of claim 4 wherein $R^3$ and $R^4$ are both hydrogen;

a pharmaceutically acceptable salt thereof, a prodrug of said compound or said salt, or a solvate or hydrate of said compound, said salt or said prodrug.

6. The compound of claim 4 wherein $R^{1b}$ and $R^{2b}$ are each independently selected from hydrogen, $(C_3–C_6)$cycloalkyl, or an $(C_1–C_6)$alkyl optionally substituted with one or more fluoro, a pharmaceutically acceptable salt thereof, a prodrug of said compound or said salt, or a solvate or hydrate of said compound, said salt or said prodrug.

7. The compound of claim 6 wherein $R^3$ and $R^4$ are both hydrogen;

a pharmaceutically acceptable salt thereof, a prodrug of said compound or said salt, or a solvate or hydrate of said compound, said salt or said prodrug.

8. The compound of claim 1 where Ar is pyridyl; $R^1$ is hydrogen, halo, or methoxy; $R^2$, $R^3$, $R^4$, $R^5$, $R^6$, $R^7$ and $R^9$ are all hydrogen; X is —O—; m is 1; and $R^8$ is —CONR$^{1b}$R$^{2b}$, where $R^{1b}$ and $R^{2b}$ are each independently hydrogen or methyl;

a pharmaceutically acceptable salt thereof, a prodrug of said compound or said salt, or a solvate or hydrate of said compound, said salt or said prodrug.

9. The compound of claim 8 wherein Ar is 3-pyridyl;

a pharmaceutically acceptable salt thereof, a prodrug of said compound or said salt, or a solvate or hydrate of said compound, said salt or said prodrug.

10. The compound of claim 1 having the Formula (IA)

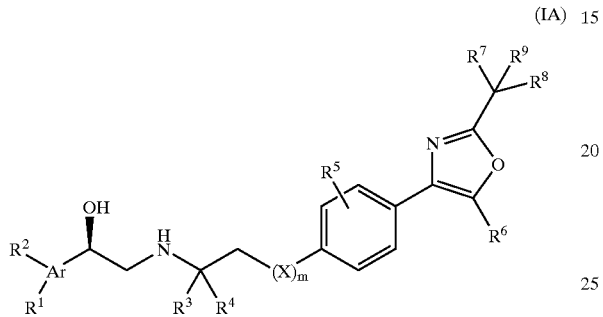

(IA)

wherein

Ar is pyridyl;

$R^1$ and $R^2$ are each independently hydrogen, hydroxy, halogen, cyano, nitro, —NR$^{1a}$R$^{2a}$, —NR$^{1a}$SO$_2$R$^{2a}$, —OR$^{1a}$, —SO$_2$R$^{2a}$, —CF$_3$, (C$_3$–C$_8$)cycloalkyl, phenyl, —NR$^{1a}$COR$^{2a}$, —COR$^{2a}$, or an (C$_1$–C$_6$)alkyl optionally substituted with one or more substituents selected from the group consisting of hydroxy, nitro, halogen, and cyano, where $R^{1a}$ and $R^{2a}$ are each independently hydrogen, (C$_3$–C$_8$)cycloalkyl, phenyl optionally substituted with 1 to 3 substituents selected from the group consisting of halo, (C$_1$–C$_6$)alkyl, and (C$_1$–C$_6$)alkoxy, or (C$_1$–C$_6$)alkyl optionally substituted with 1 to 3 substituents selected from the group consisting of hydroxy, fluoro, —CO$_2$H, phenyl, and —NR$^{1b}$R$^{2b}$, where $R^{1b}$ and $R^{2b}$ are each independently hydrogen, amino, amino(C$_1$–C$_6$)alkyl, aminoaryl, (C$_1$–C$_6$)alkyl optionally substituted with one or more substituents selected from the group consisting of hydroxy, (C$_1$–C$_6$)alkoxy, fluoro, amino, (C$_1$–C$_6$) alkylamino, and acyl, or(C$_3$–C$_8$)cycloalkyl optionally substituted with one or more substituents selected from the group consisting of fluoro, alkyl, (C$_1$–C$_6$)alkoxy, hydroxy, amino, aminoalkyl-, acyl and amido, $R^3$ and $R^4$ are each, independently, hydrogen, or (C$_1$–C$_6$) alkyl optionally substituted with 1 to 3 substituents selected from the group consisting of hydroxy, (C$_1$–C$_6$) alkoxy, and fluoro;

$R^5$ is hydrogen, (C$_1$–C$_6$)alkyl optionally substituted with 1 to 3 substituents selected from the group consisting of hydroxy, (C$_1$–C$_6$)alkoxy, and fluoro;

$R^6$ and $R^7$ are each independently hydrogen, halogen, or (C$_1$–C$_6$)alkyl optionally substituted with one or more substituents selected from the group consisting of hydroxy, (C$_1$–C$_6$)alkoxy, or fluoro;

$R^8$ is —CONR$^{1b}$R$^{2b}$, —SOR$^{1b}$, —SO$_2$R$^{1b}$, —SO$_2$NR$^{1b}$R$^{2b}$, —NR$^{1b}$SO$_2$R$^{2b}$, or —CO$_2$R$^{1b}$;

$R^9$ is hydrogen, halogen, (C$_1$–C$_6$)alkoxy, or (C$_1$–C$_6$)alkyl optionally substituted with one or more substituents selected from the group consisting of fluoro, hydroxy, and (C$_1$–C$_6$)alkoxy;

X is —O; and m is 1;

a pharmaceutically acceptable salt thereof, a prodrug of said compound or said salt, or a solvate or hydrate of said compound, said salt or said prodrug.

11. The compound of claim 10 wherein $R^5$ and $R^6$ are both hydrogen;

a pharmaceutically acceptable salt thereof, a prodrug of said compound or said salt, or a solvate or hydrate of said compound, said salt or said prodrug.

12. The compound of claim 10 wherein $R^8$ is —CONR$^{1b}$R$^{2b}$, and $R^7$ and $R^9$ are each independently hydrogen, fluoro, or (C$_1$–C$_6$)alkyl;

a pharmaceutically acceptable salt thereof, a prodrug of said compound or said salt, or a solvate or hydrate of said compound, said salt or said prodrug.

13. The compound of claim 12 where $R^5$ and $R^6$ are both hydrogen;

a pharmaceutically acceptable salt thereof, a prodrug of said compound or said salt, or a solvate or hydrate of said compound, said salt or said prodrug.

14. The compound of claim 13 wherein $R^3$ and $R^4$ are both hydrogen;

a pharmaceutically acceptable salt thereof, a prodrug of said compound or said salt, or a solvate or hydrate of said compound, said salt or said prodrug.

15. The compound of claim 13 wherein $R^{1b}$ and $R^{2b}$ are each independently selected from hydrogen, (C$_3$–C$_6$) cycloalkyl or (C$_1$–C$_6$)alkyl optionally substituted with one or more fluoro, a pharmaceutically acceptable salt thereof, a prodrug of said compound or said salt, or a solvate or hydrate of said compound, said salt or said prodrug.

16. The compound of claim 15 wherein $R^3$ and $R^4$ are both hydrogen;

a pharmaceutically acceptable salt thereof, a prodrug of said compound or said salt, or a solvate or hydrate of said compound, said salt or said prodrug.

17. The compound of claim 10 where Ar is pyridyl; $R^1$ is hydrogen, halo, methyl, or methoxy; $R^2$, $R^3$, $R^4$, $R^5$, $R^6$, $R^7$ and $R^9$ are all hydrogen;

X is —O—; m is 1; and $R^8$ is —CONR$^{1b}$R$^{2b}$, where $R^{1b}$ and $R^{2b}$ are each independently hydrogen or methyl;

a pharmaceutically acceptable salt thereof, a prodrug of said compound or said salt, or a solvate or hydrate of said compound, said salt or said prodrug.

18. The compound of claim 17 wherein Ar is 3-pyridyl;

a pharmaceutically acceptable salt thereof, a prodrug of said compound or said salt, or a solvate or hydrate of said compound, said salt or said prodrug.

19. The compound of claim 18 where $R^1$ is methyl;

a pharmaceutically acceptable salt thereof, a prodrug of said compound or said salt, or a solvate or hydrate of said compound, said salt or said prodrug.

20. The compound of claim 10 selected from the group consisting of

2-[4-(4-{2-[2(R)-hydroxy-2-(6-methyl-pyridin-3-yl)-ethylamino]-ethoxy}-phenyl)-oxazol-2-yl]-N,N-dimethyl-acetamide;

2-(4-{4-[2-(2(R)-hydroxy-2-pyridin-3-yl-ethylamino)-ethoxy]-phenyl}-oxazol-2-yl)-N,N-dimethyl-acetamide;

N,N-diethyl-2-(4-{4-[2-(2(R)-hydroxy-2-pyridin-3-yl-ethylamino)-ethoxy]-phenyl}-oxazol-2-yl)-acetamide;

2-[4-(4-{2-[2-(6-chloro-pyridin-3-yl)-2(R)-hydroxy-ethylamino]-ethoxy}-phenyl)-oxazol-2-yl]-N-ethyl-N-(2,2,2-trifluoro-ethyl)-acetamide;

2-[4-(4-{2-[2-(6-chloro-pyridin-3-yl)-2(R)-hydroxy-ethylamino]-ethoxy}-phenyl)-oxazol-2-yl]-N,N-diisopropyl-acetamide;

2-[4-(4-{2-[2-(6-chloro-pyridin-3-yl)-2(R)-hydroxy-ethylamino]-ethoxy}-phenyl)-oxazol-2-yl]-N,N-dimethyl-isobutyramide;

2-(4-{4-[2-(2(R)-hydroxy-2-pyridin-3-yl-ethylamino)-ethoxy]-phenyl}-oxazol-2-yl)-N,N-dimethyl-isobutyramide;

2-(4-{4-[2-(2(R)-hydroxy-2-pyridin-3-yl-ethylamino)-ethoxy]-phenyl}-oxazol-2-yl)-N,N-dimethyl-butyramide;

2-[4-(4-{2-[2(R)-hydroxy-2-(6-methyl-pyridin-3-yl)-ethylamino]-ethoxy}-phenyl)-oxazol-2-yl]-N,N-dimethyl-propionamide;

2-[4-(4-{2-[2(R)-hydroxy-2-(6-methyl-pyridin-3-yl)-ethylamino]-ethoxy}-phenyl)-oxazol-2-yl]-N,N-dimethyl-butyramide; and 2-[4-(4-{2-[2(R)-hydroxy-2-(6-methyl-pyridin-3-yl)-ethylamino]-ethoxy}-phenyl)-oxazol-2-yl]-N,N-dimethyl-isobutyramide;

a pharmaceutically acceptable salt thereof, or a solvate or hydrate of said compound or said salt.

21. The compound of claim 10 selected from the group consisting of

2-[4-(4-{2-[2(R)-hydroxy-2-(6-methyl-pyridin-3-yl)-ethylamino]-ethoxy}-phenyl)-oxazol-2-yl]-N,N-dimethyl-acetamide;

2-(4-{4-[2-(2(R)-hydroxy-2-pyridin-3-yl-ethylamino)-ethoxyl-phenyl}-oxazol-2-yl)-N,N-dimethyl-acetamide;

N,N-diethyl-2-(4-{4-[2-(2(R)-hydroxy-2-pyridin-3-yl-ethylamino)-ethoxy]-phenyl}-oxazol-2-yl)-acetamide;

2-[4-(4-{2-[2(R)-hydroxy-2-(6-methyl-pyridin-3-yl)-ethylamino]-ethoxy}-phenyl)-oxazol-2-yl]-N,N-dimethyl-propionamide;

2-[4-(4-{2-[2(R)-hydroxy-2-(6-methyl-pyridin-3-yl)-ethylamino]-ethoxy}-phenyl)-oxazol-2-yl]-N,N-dimethyl-butyramide; and 2-[4-(4-{2-[2(R)-hydroxy-2-(6-methyl-pyridin-3-yl)-ethylamino]-ethoxy}-phenyl)-oxazol-2-yl]-N,N-dimethyl-isobutyramide;

a pharmaceutically acceptable salt thereof, or a solvate or hydrate of said compound or said salt.

22. The compound of claim 10 having the Formula (IA-1)

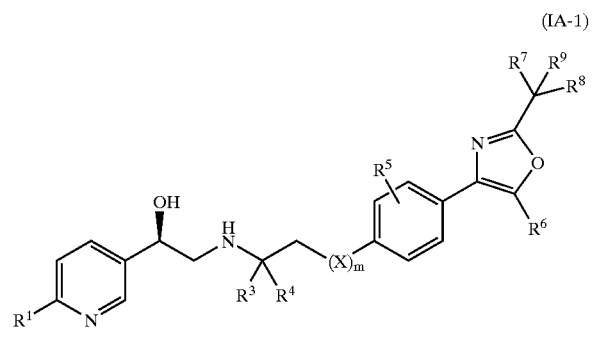

(IA-1)

wherein $R^1$ is hydrogen, hydroxy, halogen, $(C_1-C_6)$alkyl, or $(C_1-C_6)$alkoxy;

$R^3$ and $R^4$ are hydrogen;

$R^5$, $R^6$, $R^7$ and $R^9$ are each independently hydrogen or $(C_1-C_6)$alkyl optionally substituted with one or more fluoro substituents;

$R^8$ is —$CONR^{1b}R^{2b}$, where $R^{1b}$ and $R^{2b}$ are each independently selected from hydrogen, $(C_3-C_6)$cycloalkyl, or an $(C_1-C_6)$alkyl optionally substituted with one or more fluoro, X is —O—; and m is 1;

a pharmaceutically acceptable salt thereof, a prodrug of said compound or said salt, or a solvate or hydrate of said compound, said salt or said prodrug.

23. The compound of claim 22 wherein $R^1$ is hydrogen, halogen, or $(C_1-C_6)$alkyl;

$R^3$, $R^4$, $R^5$, $R^6$, $R^7$ and $R^9$ are hydrogen;

$R^8$ is —$CONR^{1b}R^{2b}$, where $R^{1b}$ and $R^{2b}$ are each independently selected from hydrogen, or $(C_1-C_6)$alkyl, X is —O—; and m is 1;

a pharmaceutically acceptable salt thereof, a prodrug of said compound or said salt, or a solvate or hydrate of said compound, said salt or said prodrug.

24. The compound of claim 23 wherein $R^1$ is methyl;

a pharmaceutically acceptable salt thereof, a prodrug of said compound or said salt, or a solvate or hydrate of said compound, said salt or said prodrug.

25. The compound of claim 24 which is

2-[4-(4-{2-[2(R)-hydroxy-2-(6-methyl-pyridin-3-yl)-ethylamino]-ethoxy}-phenyl)-oxazol-2-yl]-N,N-dimethyl-acetamide; or a pharmaceutically acceptable salt thereof, or a solvate or hydrate of said compound or said salt.

26. The compound of claim 24 which is

2-[4-(4-{2-[2(R)-hydroxy-2-(6-methyl-pyridin-3-yl)-ethylamino]-ethoxy}-phenyl)-oxazol-2-yl]-N-methyl-acetamide; or a pharmaceutically acceptable salt thereof, or a solvate or hydrate of said compound or said salt.

27. A pharmaceutical composition comprising (1) a compound of claim 1, a pharmaceutically acceptable salt thereof or a hydrate or solvate of said compound or said salt; and (2) a pharmaceutically acceptable excipient, diluent, or carrier.

* * * * *